United States Patent
Cook et al.

[19]

[11] Patent Number: 6,121,433
[45] Date of Patent: *Sep. 19, 2000

[54] OLIGOMERIC COMPOUNDS HAVING NITROGEN-CONTAINING LINKAGES

[75] Inventors: Phillip Dan Cook, Vista; Yogesh S. Sanghvi, San Marcos; Pei Pei Kung, Carlsbad, all of Calif.

[73] Assignee: ISIS Pharmaceuticals, Inc., Carlsbad, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/669,300

[22] PCT Filed: Jan. 11, 1995

[86] PCT No.: PCT/US95/00350

§ 371 Date: Aug. 8, 1996

§ 102(e) Date: Aug. 8, 1996

[87] PCT Pub. No.: WO95/18623

PCT Pub. Date: Jul. 13, 1995

Related U.S. Application Data

[63] Continuation-in-part of application No. 08/180,124, Jan. 11, 1994, Pat. No. 5,783,682, and a continuation-in-part of application No. 08/039,979, Mar. 30, 1993, abandoned, and a continuation-in-part of application No. 08/039,846, Mar. 30, 1993, abandoned, and a continuation-in-part of application No. 08/040,933, Mar. 31, 1993, abandoned, and a continuation-in-part of application No. 08/040,903, Mar. 31, 1993, Pat. No. 5,386,023, and a continuation-in-part of application No. 08/040,526, Mar. 31, 1993, Pat. No. 5,489,677, which is a continuation-in-part of application No. PCT/US92/04294, May 21, 1992, and a continuation-in-part of application No. 07/903,160, Jun. 24, 1992, abandoned, which is a continuation-in-part of application No. 07/703,619, May 21, 1991, Pat. No. 5,378,825, which is a continuation-in-part of application No. 07/566,836, Aug. 13, 1990, Pat. No. 5,223,618, and a continuation-in-part of application No. 07/558,663, Jul. 27, 1990, Pat. No. 5,138,045.

[51] Int. Cl.[7] ............ C07H 19/00; C07H 21/02; C07H 21/04; A01N 43/04

[52] U.S. Cl. ............ 536/22.1; 536/18.7; 536/24.3; 536/24.31; 536/24.32; 536/24.5; 514/44; 585/500

[58] Field of Search ............ 514/44; 536/24.3, 536/24.31, 24.32, 24.5, 22.1, 18.7; 585/500

[56] References Cited

U.S. PATENT DOCUMENTS 5,264,562  11/1993  Matteucci ............... 536/23.1

FOREIGN PATENT DOCUMENTS

| 86/05518 | 9/1986 | WIPO. |
| WO 91/19735 | 12/1991 | WIPO. |
| WO 92/05186 | 4/1992 | WIPO. |
| WO 92/20822 | 11/1992 | WIPO. |
| WO 93/04204 | 3/1993 | WIPO. |
| WO 94/22454 | 10/1994 | WIPO. |

OTHER PUBLICATIONS

Augustyns, et al., "Influence of the incorporation of (S)–9–(3,4–dihydroxy–butyl) adenine on the enzymatic stability and base–pairing properties of oligodeoxynucleotides", *Nucl. Acids Res.*, 1991, 19(10), 2587–2593.

(List continued on next page.)

*Primary Examiner*—Ardin H. Marschel
*Assistant Examiner*—Jezia Riley
*Attorney, Agent, or Firm*—Woodcock Washburn Kurtz Mackiewicz & Norris LLP

[57] ABSTRACT

Novel compounds and libraries of compounds based on nitrogen atoms that are joined together with spanner groups include "letters" i.e., functional groups, that are attached to the nitrogen atoms, to the spanner groups or to both the nitrogen atoms and the spanner groups to render the compounds and libraries of such compounds with diverse properties.

13 Claims, 14 Drawing Sheets

OTHER PUBLICATIONS

Cho et al., "An Unnatural Biopolymer", *Science,* 1993, 261, 1303–1305.

Cormier et al., "Synthesis of hexanucleotide analogues containing diisopropylsilyl internucleotide linkages", *Nucl. Acids Res.,* 1988, 16(10), 4583–4594.

Crooke and Lebleu (Eds.), *Antisense Research and Applications,* CRC Press, Inc., Boca Raton, FL, 1993.

Debart et al., "Intermolecular Radical C–C Bond Formation: Synthesis of a Novel Dinucleoside Linker for Non–anionic Antisense Oligonucleosides", *Tetra. Lett.,* 1992, 33(19), 2645–2648.

Giannis et al., "Fragmentation and Witting Olefination of Glucosamine Derivatives—A Simple Route to Open Chain Amino Sugars and Chiral Glycerols", *Tetra. Lett.,* 1988, 44(23), 7177–7180.

Goodchild, "Conjugates of Oligonucleotides and Modified Oligonucleotides: A Review of their Synthesis and Properties", *Bioconj. Chem.,* 1990, 1(3), 165–187.

Greene and Wuts (Eds.), "Protection for the Carbonyl Group", *Protection Groups in Organic Synthesis,* John Wiley & Sons, Inc., 1991, 175–223.

Hanvey, et al., "Antisense and Antigene Properties of Peptide Nucleic Acids", *Science,* 1992, 258, 1481–1485.

Hart et al., "Bis(trimethylstannyl)Benzopinacolate–Mediated Intermolecular Fee–Radical Carbon–Carbon Bond–Forming Reactions: A New One–Carbon Homologation", *J. Am. Chem. Soc.,* 1988, 110, 1631–1633.

Hendra and Loader, "Synthetic Analogues of Polynucleotides", *Nature,* 1968, 217, 638–640.

Hillgartner et al., "Bis(trimethylzinn)benzpinakolat, seine reversible Radikalische Dissoziation und Reaktionen", *Liebigs Ann. Chem.,* 1975, 586–599.

Hyrup et al., "Modification of the Binding Affinity of Peptide Nucleic Acids (PNA). PNA with Extended Backbones Consisting of 2–Aminoethyl–β–alanine or 3–Aminopropylglycine Units",*J. Chem. Soc., Chem. Commun.,* 1993, 518–519.

Inouye et al., "Selective Coloration of Spiro Pyridopyrans for Guanosine Derivatives", *J. Am. Chem. Soc.,* 1992, 114(2), 778–780.

Lin et al., "Synthesis and Biological Activity of Several Amino Analogues of Thymidine", *J. Med. Chem.,* 1978, 21(1), 109–112.

Loke et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis", *Top. Microbiol. Immunol.,* 1988, 141, 282–289.

Ma et al., "Design and synthesis of RNA miniduplexes via a synthetic linker approach. 2. Generation of covalently closed, double–stranded cyclic HIV–1 TAR RNA analogs with high Tat–binding affinity", *Nucl. Acids. Res.,* 1993, 21(11), 2585–2589.

March, J. (Ed)., *Advanced Organic Chemistry, Ractions, Mechanisms and Structure,* J. Wiley & Sons, New York, 1992, 352.

Marcus–Sekura et al., "Comparative inhibition of chloramphenicol acetyltransferase gene expression by antisense oligonucleotide analogues having alkyl phosphotriester, methylphosphonate and phosphorothiate linkages", *Nucl. Acids. Res.,* 1987, 15(14), 5749–5763.

Matteucci, "Deoxyoligonucleotide Analogs Based on Formacetal Linkages", *Tetra. Lett.,* 1990, 31(17), 2385–2388.

Mazur et al., "Isosteres of Natural Phosphates. 11. Synthesis of a Phosphonic Acid Analogue of an Oligonucleotide", *Tetrahedron,* 1984, 40(20), 3949–3956.

Miller et al., "Effects of a Trinucleotide Ethyl Phosphotriester, $G^M$p(Et)$G^m$p(Et)U, on Mammalian Cells in Culture", *Biochem.,* 1977, 16(9), 1988–1996.

Nair et al., "Regiospecific 5'–Silylation of Nucleosides", *Organic Prep. Proc. Int.,* 1990, 22(1), 57–61.

Niitsu et al., "Syntheses of a Series of Linear Pentaamines with Three and Four Methylene Chain Intervals", *Chem. Pharm. Bull.,* 1986, 34, 1032–1038.

Pauling, "Molecular Architecture and Biological Reactions", *Chem. Engin. News,* 1946, 24(10), 1375–1377.

Perkins et al., "Accelerated Displacement of Duplex DNA Strands by a Synthetic Circular Oligodeoxynucleotide", *J. Chem. Soc., Chem. Commun.,* 1993, 215–216.

Pitha, "Physiological Activities of Synthetic Analogs of Polynucleotides", *Adv. in Polymer Sci.,* 1983, 50, 2–16.

Pon, "Solid–phase Supports in Oligonucleotide Synthesis", *Oligonucleotide Synthesis Protocols,* S. Agrawal (Ed.), Humana Press, 1993.

Prakash et al., "Molecular Recognition by Circular Oligonucleotides. Strong Binding of Single–stranded DNA and RNA", *J. Chem. Soc., Chem. Commun.,* 1991, 1161–1163.

Rebek, "Molecular Recognition and Biophysical Organic Chemistry", *Acc. of Chem. Res.,* 1990, 23(12), 399–404.

Rentzeperis et al., "Contribution of Loops and Nicks to the Formation of DNA Dubbells: Melting Behavior and Ligand Binding", *Biochem.,* 1993, 32–(10), 2564–2571.

Trapani et al., "N–1–Alkenyl–N, S–Diacyl–2–Aminobenzenethiols (Enamides) by Ring–Opening of 2,3–Dihydro–1,3–benzothiazoles with Aliphatic Carboxylic Anhydrides", *Synthesis,* 1988, 84–87.

Trost, B.M. and Fleming I. (Eds.), *Comprehensive Organic Synthesis,* Pergamon Press, Oxford, 1991, 4, 758–776.

Tuladhar et al., "A Synthetic Route to Poly–N,N'–Dimethylethylenediamines", *Tetra. Lett.,* 1992, 33(16), 2203–2206.

Wilson, "Cellular Transport Mechanisms", *Ann. Rev. Biochem.,* 1978, 47, 933–965.

Yamamoto et al., "One–step Synthesis of 5'Azido–nucleosides", *J. Chem. Soc. Perkin I,* 1980, 306–310.

Zuckermann et al., "Efficient Method for the Preparation of Peptoids [Oligo(N–substituted glycines)] by Submonomer Solid–Phase Synthesis", *J. Am. Chem. Soc.,* 1992, 114, 10646–10647.

Erwin et al., *Biochem. J.,* 1986, 238, 581–587.

Hart et al., *J. Am. Chem. Soc.,* 1988, 110, 1631–1633.

Hyrup et al., *J. Am. Chem. Soc.,* 1994, 116, 7964–7970.

Kang et al., *Biopolymers,* 1992, 32(10), 1351–1363 (abstract).

McGraw et al., *Biotechniques,* 1990, 8(6), 674–678.

Westermann et al., *Biomed. Biochim Acta,* 1989, 48(1), 85–93.

Achari et al., "Facing up to Membranes: Structure/Function Relationships in Phospholipases", *Cold Spring Harbor Symp. Quant. Biol.,* 1987, 52, 441–452.

Alul et al., "Oxalyl–CPG: a labile support for synthesis of sensitive oligonucleotide derivatives", *Nucl. Acids. Res.,* 1991, 19(7), 1527–1532.

Beaucage et al., "Advances in the Synthesis of Oligonucleotides by the Phosphoramidite Approach", *Tetra.,* 1992, 48(12), 2223–2311.

Bomalaski et al., "Human Extracellular Recombinant Phospholipase $A_2$ Induces an Inflammatory Response in Rabbit Joints", *J. Immunol.,* 1991, 146(11), 3904–3910.

Burack et al., "Role of Lateral Phase Separation in the Modulation of Phospholipase $A_2$ Activity", *Biochem.,* 1993, 32, 583–589.

Campbell et al., "Inhibition of Phospholipase A2; a Molecular Recognition Study", *J. Chem. Soc., Chem. Commun.,* 1988, 1560–1562.

Cho et al., "The Chemical Basis for Interfacial Activation of Monomeric Phospholipases $A_2$", *J. Biol., Chem.,* 1988, 263(23), 11237–11241.

Dennis, E.A., *The Enzymes,* Boyer, P.D., ed., Academic Press, New York, 1983, vol. 16, Ch. 9, 307–353.

Davidson et al., "Inhibition of Phospholipase $A_2$ by "Lipocortins" and Calpactins", *J. Biol. Chem.,* 1987, 262(4), 1698–1705.

Davidson et al., "1–Stearyl,2–Stearoylaminodeoxy Phosphatidylcholine, A Potent Reversible Inhibitor of Phospholipase $A_2$", *Biochem. Biophys. Res. Commun.,* 1986, 137(2), 587–592.

Ecker et al., "Rational screening of oligonucleotide combinatorial libraries of drug discovery", *Nucl. Acids Res.,* 1993, 21(8), 1853–1856.

Englisch et al., "Chemically Modified Oligonuceotides as Probes and Inhibitors", *Angew. Chem. Int. Ed. Engl.,* 1991, 30, 613–629.

Franson et al., "Phospholipid metabolism by phagocytic cells. Phospholipases $A_2$ associated with rabbit polymorphonuclear leukocyte granules", *J. Lipid Res.,* 1974, 15, 380–388.

Geysen et al., "Strategies for epitope analysis using peptide synthesis", *J. Immunol. Methods,* 1987, 102, 259–274.

Glaser et al., "Phospholipase $A_2$ enzymes: regulation and inhibition", *TiPS,* 1993, 14, 92–98.

Grainger et al., "An enzyme caught in action: direct imaging of hydrolytic function and domain formation of phospholipase $A_2$ in phosphatidylcholine monolayers", *FEBS Lett.,* 1989, 252(1,2), 73–82.

Halford et al., "Synthetic Analogues of Polynucleotides" *Nature,* 1968, 217, 638–640.

Houghton et al., "Generation and use of synthetic peptide combinatorial libraries for basic research and drug discovery", *Nature,* 1991, 354, 84–86.

Kroschwitz, J.I. (ed.), *Concise Encyclopedia of Polymer Science and Engineering,* John Wiley & Sons, 1990, 858–859.

Lombardo et al., "Cobra Venom Phospholipase $A_2$ Inhibition by Manoalide", *J. Biol. Chem.,* 1985, 260(12), 7234–7240.

Märki et al., "Differential inhibition of human secretory and cytosolic phospholipase $A_2$", *Agents Action,* 1993, 38, 202–211.

Mellor, D.P., "The Chelation of Heavy Metals", *Chemistry of Chelation and Chelating Agents in International Encyclopedia of Pharmacology and Therapueutics,* Levine, W.G., (ed.), Pergamon Press, Elmford, NY, Section 70, 1979.

Miyake et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A Competitive Inhibitor of Group II Phospholipase $A_2$", *J. Pharm. Exp. Therap.,* 1992, 263(3), 1302–1307.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.,* 1990, 112, 3704–3706.

Ohlmeyer et al., "Complex synthetic chemical libraries indexed with molecular tags", *Proc. Natl. Acad. Sci. USA,* 1993, 90, 10922–10926.

Oinuma et al., "Synthesis and Biological Evaluation of Substituted Benzenesulfonamides as Novel Potent Membrane–Bound Phospholipase $A_2$ Inhibitors", *J. Med. Chem.,* 1991, 34, 2260–2267.

Owens et al., "The Rapid Identification of HIV Protease Inhibitors Through the Synthesis and Screening of Defined Peptide Mixtures", *Biochem. Biophys. Res. Commun.,* 1991, 181(1), 402–408.

Pruzanski et al., "Enzymatic Activity and Immunoreactivity of Extracellular Phospholipase $A_2$ in Inflammatory Synovial Fluids", *Inflamm.,* 1992, 16(5), 451–457.

Scott et al., "Interfacial Catalysis: The Mechanisms of Phospholipase A2", *Science,* 1990, 250, 1541–1546.

Simon et al., "Peptoids: A modular approach to drug discovery", *Proc. Natl. Acad. Sci. USA,* 1992, 89, 9367–9371.

Tanaka et al., "A Novel Type of Phospholipase $A_2$ Inhibitor, Thielocin A1β, and Mechanism of Action", *J. Antibiotics,* 1992, 45(7), 1071–1078.

Vishwanath et al., "Edema–Inducing Activity of Phospholipase A2 Purified From Human Synovial Fluid and Inhibition by Aristolochic Acid", *Inflamm.,* 1988, 12(6), 549–561.

Washburn et al., "Suicide–inhibitory Bifunctionally Linked Substrates (SIBLINKS) as Phospholipase $A_2$ Inhibitors", *J. Biol. Chem.,* 1991, 266(8), 5042–5048.

Wery et al., "Structure of recombinant human rehumatoid arthritic synovial fluid phospholipase $A_2$ at 2.2 Åresolution", *Nature,* 1991, 352, 79–82.

Wright et al., "Large Scale and Synthesis of Oligonucleotides via Phosphoramidite Nucleosides and a High–loaded Polystyrene Support", *Tetra. Lett.,* 1993, 34(21), 3373–3376.

Wyatt et al., "Combinatorially selected guanosine–quartet structure is a potent inhibitor of human immunodeficiency virus envelope–mediated cell fusion", *Proc. Natl. Acad. Sci. USA,* 1994, 91, 1356–1360.

Yang et al., "Studies on the status of lysine residues in phospholipase $A_2$ from *Naja naja atra* (Taiwan cobra) snake venom", *Biochem. J.,* 1989, 262, 855–860.

Yuan et al., "Synthesis and Evaluation of Phospholipid Analogues as Inhibitors of Cobra Venom Phospholipase $A_2$", *J. Am. Chem. Soc.,* 1987, 109, 8071–8081.

Saab, N.H. et al., "Synthesis&Evaluation of Unsymmetrically Substituted Polyamine Analogues as Modulators of Human Spermidine/Spermine–$N^1$–Acetyltransferase (SSAT)&As Potential Antitumor Agents", *J.Med.Chem.,* 1993, 36, 2998–3004.

Nielsen et al. "Sequence–selective recognition of DNA by strand displacement with thymine–substituted polyamide" Science vol. 254, pp. 1497–1500, 1991.

Abdel–Magid et al. "Reductive amination of aldehydes and ketones by using sodium triacetoxyborohydride" Tetrahedron Letters, vol. 31, pp. 5595–5598, 1990.

Zuckermann et al. "Efficient method for the preparation of peptoids [Oligo(N–substituted glycines)] by submonomer solid–phase synthesis" J. Am. Chem. Soc., vol. 114, pp. 10646–10647, 1992.

Wolfe et al. "five–membered rings. II. Inter and intramolecular reactions of simple amines with N–substituted phthalimides. Methylamine as a reagent for removal of a phthaloyl group from nitrogen", Canadian Journal of chemistry, vol. 48, pp. 3572–3679, 1970.

Egholm et al. "Peptide Nucleic Acid (PNA). Oligonucleotide Analogues with Achiral PeptideBacbone", J. Am. Chem. Soc., vol. 114, pp. 1895–1897, 1992.

Morrison & Boyd, Organic Chemistry, 3rd Edition, Allyn and Bacon, Inc. Boston, pp. 738–740, 1973.

Metzler, Biochemistry, Academic Press, Inc. (NY, NY), p. 820, 1977.

Sereny, B., "Breakdown of Amino Acids by Enterobacteriaceae", *Acta Microbiol. Acad. Sci. Hung.,* 1966, 13, 167–169.

BG-NH-(CH$_2$)$_2$-NH-(CH$_2$)$_3$O-NPhth (109)

(A) ↓ separate/react

→ BG-NH-(CH$_2$)$_2$-NL$_1$-(CH$_2$)$_3$O-NPhth (114a)

→ BG-NH-(CH$_2$)$_2$-NL$_2$-(CH$_2$)$_3$O-NPhth (114b)

→ BG-NH-(CH$_2$)$_2$-NL$_3$-(CH$_2$)$_3$O-NPhth (114c)

→ BG-NH-(CH$_2$)$_2$-NL$_4$-(CH$_2$)$_3$O-NPhth (114d)

mix (B)

BG-NH-(CH$_2$)$_2$-NL$_{1-4}$-(CH$_2$)$_3$O-NPhth (115)

(C) ↓ NH$_2$NHMe

BG-NH-(CH$_2$)$_2$-NL$_{1-4}$-(CH$_2$)$_3$O-NH$_2$ (116)

(D) ↓ 1) OCH(CH$_2$)$_2$O-NPhth (105)
2) NaCNBH$_3$

BG-NH-(CH$_2$)$_2$-NL$_{1-4}$-(CH$_2$)$_3$O-NH-(CH$_2$)$_3$O-NPhth (117)

(E) ↓ sep/react/mix

BG-NH-(CH$_2$)$_2$-NL$_{1-4}$-(CH$_2$)$_3$O-NL$_{1-4}$-(CH$_2$)$_3$O-NPhth (118)

Figure 9a      BG = t-Boc

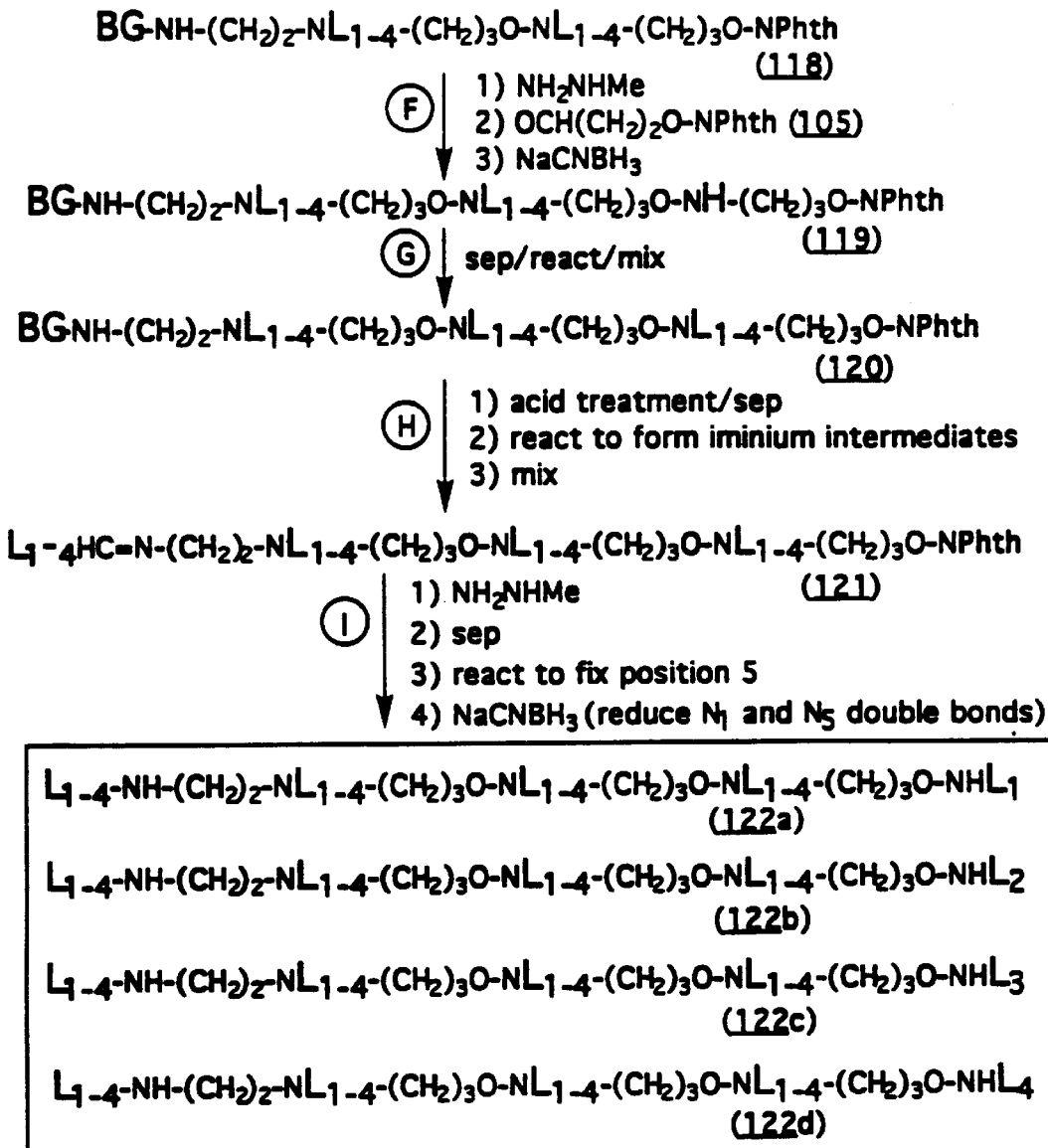
First Round Library (position 5 fixed)
four sets, 256 compounds/set
1024 total compounds
Figure 9b     BG = t-Boc BG-NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NPhth (120)

Ⓙ  1) NH$_2$NHMe
   2) react to fix position 5 with active letter from first round
   3) NaCNBH$_3$ BG-NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NL$_1$ (123)

Ⓚ  1) acid treatment/sep
   2) react

L$_1$NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NL$_x$ (124a)

L$_2$NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NL$_x$ (123b)

L$_3$NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NL$_x$ (123c)

L$_4$NH-(CH$_2$)$_2$-NL$_{1-4}$-(CH$_2$)$_3$O-NL$_{1-4}$-(CH$_2$)$_3$O-NL$_{1-4}$-(CH$_2$)$_3$O-NL$_x$ (123d)

Second Round Library (first position fixed)
four sets, 64 compounds/set
256 total compounds BG = t-Boc

Figure 10

Third Round Library (fourth position fixed)
four sets, 16 compounds/set
64 total compounds BG = t-Boc Fourth Round Library (third position fixed)
four sets, 4 compounds/set
16 total compounds

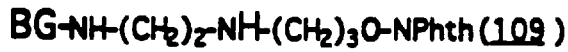
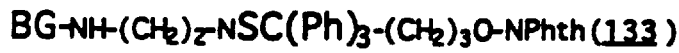
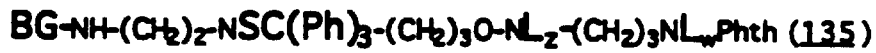
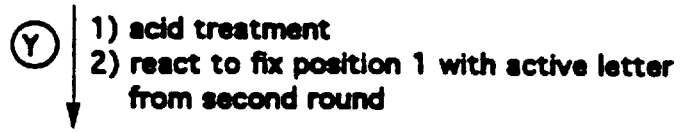
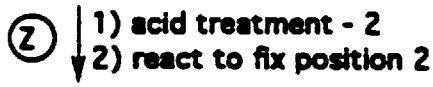
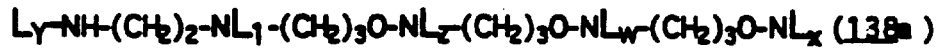
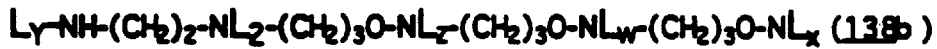
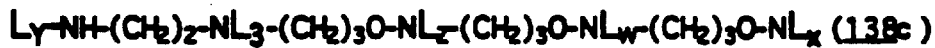
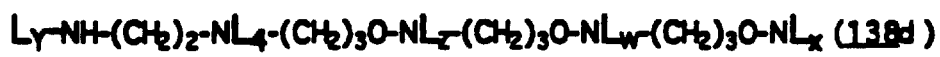
Fifth Round Library (fix second position fixed)
four sets, 1 compound/set
4 total compounds
BG = t-Boc
Figure 13

OLIGOMERIC COMPOUNDS HAVING NITROGEN-CONTAINING LINKAGES

CROSS REFERENCE TO RELATED APPLICATIONS

This application is a continuation-in-part of the following U.S. applications Ser. No. 08/180,124, filed Jan. 11, 1994 now U.S. Pat. No. 5,783,682; Ser. No. 08/039,979, filed Mar. 30, 1993 now abandoned; Ser. No. 08/039,846, filed Mar. 30, 1993 now abandoned; Ser. No. 08/040,933, filed Mar. 31, 1993 now abandoned; Ser. No. 08/040,903, filed Mar. 31, 1993 now U.S. Pat. No. 5,386,023; and Ser. No. 08/040,526, filed Mar. 31, 1993 now U.S. Pat. No. 5,489,677. Each of the foregoing are continuations-in-part of PCT/US92/04294, filed May 21, 1992, and of U.S. Ser. No. 07/903,160, filed Jun. 24, 1992 now abandoned, which are continuations-in-part of U.S. Ser. No. 07/703,619, filed May 21, 1991 now U.S. Pat. No. 5,378,825, which is a continuation-in-part of U.S. Ser. No. 07/566,836, filed Aug. 13, 1990 now U.S. Pat. No. 5,223,618, and U.S Ser. No. 07/558,663, filed Jul. 27, 1990 now U.S. Pat. No. 5,138,045. Each of these patent applications are assigned to the assignee of this application and are incorporated by reference herein.

FIELD OF THE INVENTION

This invention relates to the design, synthesis and application of oligomeric compounds containing monomeric units that each include a nitrogen atom plus a. "spanner," i.e. a group of atoms that spans between and connects adjacent nitrogen atoms. The monomeric units are connected together in linear or cyclic arrays. The monomeric units are substituted, via substitution on the nitrogen atom and/or substitution on the spanner with a tethered or untethered functional group. The oligomers are synthesized having either a random or a predefined sequences of units. Randomization can be effected independently at the functional functional group. The oligomers are synthesized having either a random or a predefined sequences of units. Randomization can be effected independently at the functional group or at the spanners. The functional group on each of the monomeric units provides for binding of the oligomeric structures to proteins, nucleic acids, lipids and other biological targets. In preferred embodiments, the compounds of the invention act as inhibitors of enzymes such as phospholipase $A_2$: as inhibitors of pathogens such as virus, mycobacterium, bacteria (gram negative and gram positive), protozoa and parasites; as inhibitors of ligand-receptor interactions such as PDGF (platelet derived growth factor), LTB4 (leukotriene B4), IL-6 and complement $C5_A$; as inhibitors of protein/protein interactions including transcription factors such as p50 ($NF_{kappa}B$ protein) and fos/jun; and for the inhibition of cell-based interactions including ICAM induction (using inducers such as IL1-β, TNF and LPS). In other preferred embodiments, the compounds of the invention are used as diagnostic reagents, including diagnostic reagents in the tests for each of the above noted systems, and as reagents in assays and as probes.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de novo design of active compounds based on the high resolution structures of enzymes has not been successful.

In order to maximize the advantages of each classical approach, new strategies for combinatorial unrandomization have been developed independently by several groups. Selection techniques have been used with libraries of peptides (see Geysen, H. M., Rodda, S. J., Mason, T. J., Tribbick, G. & Schoofs, P. G., *J. Immun. Meth.* 1987, 102, 259–274; Houghten, R. A., Pinilla, C., Blondelle, S. E., Appel, J. R., Dooley, C. T. & Cuervo, J. H., *Nature*, 1991, 354, 84–86; Owens, R. A., Gesellchen, P. D., Houchins, B. J. & DiMarchi, R. D., *Biochem. Biophys. Res. Commun.*, 1991, 181, 402–408), nucleic acids (see Wyatt, J. R., et al., *Proc. Natl. Acad. Sci. USA*, 1994, 91, 1356–1360; Ecker, D. J., Vickers, T. A., Hanecak, R., Driver, V. & Anderson, K., *Nucleic Acids Res.*, 1993, 21, 1853–1856) and nonpeptides (see Simon, R. J., et al., *Proc. Natl. Acad. Sci. USA*, 1992, 89, 9367–9371; Zuckermann, R. N., et al., *J. Amer. Chem. Soc.*, 1992, 114, 10646–10647; Bartlett, Santi, Simon, PCT WO91/19735; and Ohlmeyer, M. H., et al., *Proc. Natl. Acad. Sci. USA*, 1993, 90, 10922–10926). The techniques involve iterative synthesis and screening of increasingly simplified subsets of oligomers. Monomers or sub-monomers that have been utilized include amino acids and nucleotides both of which are bi-functional. Utilizing these techniques, libraries have been assayed for activity in either cell-based assays, or for binding or inhibition of purified protein targets.

A technique, called SURF (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified. The SURF technique is described in Ecker, D. J., Vickers, T. A., Hanecak, R., Driver, V. & Anderson, K., *Nucleic Acids Res.*, 1993, 21, 1853–1856. The SURF method is further described in PCT patent application WO 93/04204, the entire disclosure of which is herein incorporated by reference.

The combinatorial chemical approach that has been most utilized to date, utilizes an oligomerization from a solid support using monomeric units and a defined connecting chemistry, i.e. a solid support monomer approach. This approach has been utilized in the synthesis of libraries of peptides, peptoids, carbamates and vinylogous peptides connected by amide or carbamate linkages or nucleic acids connected by phosphate linkages as exemplified by the citations in previous paragraphs above. The mixture of oligomers (pool or library) is obtained from the addition of a mixture of activated monomers during the coupling step or from the coupling of individual monomers with a portion of the support (bead splitting) followed by remixing of the support and subsequent splitting for the next coupling. In this monomeric approach, each monomeric unit would carry a tethered letter, i.e., a functional group for interaction with the target. A further coupling chemistry that allows for the insertion of a tethered letter, at a chemically activated intermediate stage is referred to as the sub-monomer approach.

The diversity of the oligomeric pool is represented by the inherent physical properties of each monomer, the number of different monomers mixed at each coupling, the physical properties of the chemical bonds arising from the connecting chemistry (the backbone), the number of couplings (length of oligomer), and the interactions of the backbone and monomer chemistries. Taken together these interactions provide a global shape for each individual molecule.

There remains a need in the art for molecules which have fixed preorganized geometry that matches that of a target such as proteins and enzymes, nucleic acids and lipids. The backbone of such molecules should be rigid with some flexibility and easy to construct in solution or via automated synthesis on solid support. We have developed certain nitrogen coupled chemistries that we utilized to prepare a class of compounds we refer to as "oligonucleosides." We have described these compounds in previous patent applications including published PCT applications WO 92/20822 (PCT US92/04294) and WO 94/22454 (PCT US94/03313). These chemistries included amine linkages, hydroxylamine linkages, hydrazino linkages and other nitrogen based linkages. We have now found that these same linkages can be utilized to prepare linear and cyclized oligomeric compounds that carry functional groups thereon that are capable of interacting with a variety of target structures including proteins and enzymes, nucleic acids, lipids and other target molecules.

OBJECTS OF THE INVENTION

It is an object of the invention to provide oligomeric compounds for diagnostic, research, and therapeutic use.

It is a further object of the invention to provide oligomeric compounds wherein functional groups are coupled to at least some of the monomeric units of the oligomeric compounds via nitrogen atoms in the monomeric unit.

It is yet another object of the invention to provide methods for combinatorial synthesis of libraries of oligomeric compounds.

It is yet another object of the invention to provide libraries of combinatorized compounds.

These and other objects will become apparent to persons of ordinary skill in the art from a review of the present specification and the appended claims.

SUMMARY OF THE INVENTION

The present invention provides novel compounds that mimic, modulate or otherwise interact with various target molecules including proteins and enzymes, nucleic acids and lipids. In certain embodiments, the compounds contain one or more selected functional groups for interactions with the target molecule. At least a portion of the compounds of the invention has structure I:

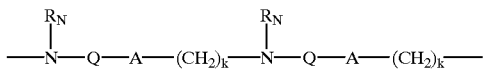

wherein:

each $R_N$ is, independently, H, —T—L, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, a polyalkyl glycol, or $C_7$–$C_{14}$ aralkyl or substituted aralkyl; a nitrogen, sulfur or oxygen containing heterocycle; and where the substitutents groups are selected from hydroxyl, alkoxy, alcohol, benzyl, phenyl, nitro, thiol,n thioalkoxy, halogen, or alkyl, aryl, alkenyl, or alkynyl groups;

each Q is, independently, N—$R_N$, O, S, SO, $SO_2$ or $(CH_2)_m$ where m is 1–5;

k is zero or 1;

each A is, independently, $R_S$—X(T—L)—$R_S$; N—$R_N$; C(O); a single bond; $(CH_2)_m$ where m is 1–5; or $CR^1R_N$;

each $R_S$ is, independently, a single bond or alkyl having 1 to about 12 carbon atoms;

each T is, independently, a single bond, a methylene group or a group having structure II:

where:

D is C(O), C(S), C(Se), $C(R^1)(NR^3R^4)$, $CH_2R^1$, $CHR^1R^2$, or $NR^3R^4$;

B is a single bond, CH=CH, C≡C, O, S or $NR^4$;

each $R^1$ and $R^2$ is independently selected from the group consisting of hydrogen, alkyl or alkenyl having 1 to about 12 carbon atoms, hydroxy- or alkoxy- or alkylthio-substituted alkyl or alkenyl having 1 to about 12 carbon atoms, hydroxy, alkoxy, alkylthio, amino and halogen;

$R^3$ and $R^4$, independently, are H, —T—L, alkyl having 1 to about 10 carbon atoms; alkenyl having 2 to about 10 carbon atoms; alkynyl having 2 to about 10 carbon atoms; aryl having 7 to about 14 carbon atoms; heterocyclic; a conjugate molecule; or $R^3$ and $R^4$, together, are cycloalkyl having 3 to about 10 carbon atoms or cycloalkenyl having 4 to about 10 carbon atoms;

n and o, independently, are zero to 5;

q is zero or 1;

p is zero to about 10;

each L is, independently, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl or $C_7$–$C_{14}$ aralkyl or sustututed aralkyl, and where the substitutents groups are selected from hydroxyl, alkoxy, alcohol, benzyl, phenyl, nitro, thiol, thioalkoxy, halogen, or alkyl, aryl, alkenyl, or alkynyl groups; an ether having 2 to 10 carbon atoms and 1 to 4 oxygen or sulfur atoms; a polyalkyl glycol; a nitrogen, sulfur or oxygen containing heterocycle; a metal coordination group; a conjugate group; halogen; hydroxyl (OH); thiol (SH); keto (C=O); carboxyl (COOH); amide (CONR); ethers; thioethers; amidine (C(=NH)

NRR); guanidine (NHC(=NH)NRR); glutamyl CH(NRR)(C(=O)OR); nitrate (ONO$_2$); nitro (NO$_2$); nitrile (CN); trifluoromethyl (CF$_3$); trifluoromethoxy (OCF$_3$); O-alkyl; S-alkyl; NH-alkyl; N-dialkyl; O-aralkyl; S-aralkyl; NH-aralkyl; amino (NH$_2$); azido (N$_3$); hydrazino (NHNH$_2$); hydroxylamino (ONH$_2$); sulfoxide (SO); sulfone (SO$_2$); sulfide (S—); disulfide (S—S); silyl; a nucleosidic base; an amino acid side chain; a carbohydrate; a drug; or group capable of hydrogen bonding;

each X is, independently, N or CH, or

X and T, together, form an aromatic moiety.

Preferred nitrogen blocking groups of the invention include tert-butoxycarbonyl, sulfenyltriphenyl and phthaloyl nitrogen protecting group.

The compounds of the invention generally are prepared by coupling preselected bifunctional synthons under conditions effective to form the above-noted structures. In certain embodiments, the compounds of the invention are prepared by intermolecular reductive coupling of, for example, a hydrazine moiety on a first synthon with an aldehyde moiety on a second synthon. In other embodiments, the compounds of the invention are prepared by coupling a carbocentric radical on a first synthon with, for example, a radical acceptor moiety on a second synthon. In further embodiments, the compounds are prepared through a nucleophilic alkylation wherein a nucleophilic moiety on a first synthon displaces a leaving group on a second synthon.

The present invention is further directed to libraries of compounds. Preferable libraries include combinatorialized of compounds wherein the individual members of libraries comprise compounds of the structure:

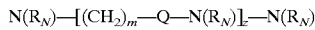

wherein

Q is N, O or (CH$_2$)$_m$;

each R$_N$ is a member of a group of letters;

m is 1 to 5; and z is 2 to 100.

In a more preferred size range of the members of the libraries, z above is 2 to 25. In still other embodiments of the invention z is 2 to 10. An even more preferred range is wherein z is 2 to 5.

A first preferred group of letters, i.e. the variable R$_N$ above, include aryl or substituted aryl letters. A further preferred group of letters include amino acid side chain letters. A further preferred group of letters include aliphatic, substituted aliphatic, aromatic or substituted aromatic letters.

In certain preferred libraries of compounds the invention, the individual members of the libraries are formed from linked units derived from intermediates of the structure:

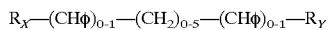

wherein:

φ is a letter, a tethered letter or H, and provided that in those compounds having a single φ, then φ is a letter or a tethered letter; and in those compounds having multiple φs, then at least one φ is a letter or a tethered letter and the remaining are either H, a letter or tethered letter;

R$_X$ is aldehyde, ketone, halide, acid or acid halide;

R$_Y$ is N$_3$, NO$_2$, N-bg, ON-bg, NφN-bg or SO$_2$N-bg; and bg is a nitrogen blocking group or a solid phase support.

In further preferred libraries of compounds the invention, the individual members of the libraries are formed from linked units derived from intermediates of the structure:

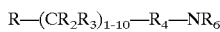

wherein:

R is aldehyde, ketone, halide, acid or acid halide;

R$_2$ and R$_3$ are H, alkyl, substituted alkyl, aryl, substituted aryl, aralkyl, substituted aralkyl, heterocycle, moiety as found in α-position of amino acids, halogen, amine, substituted amine, hydroxy, alkoxyl, substituted alkoxyl, SH, or substituted thioalkoxyl;

R$_4$ is O, CH$_2$, CR$_2$R$_3$, NH, NR$_5$ or SO$_2$

R$_5$ is alkyl, substituted alkyl, aryl or substituted aryl; and

R6 is phthaloyl, H$_2$, N$_2$, O$_2$, H Acetyl, diAcetyl, methyleneamino, or an amino protecting group.

BRIEF DESCRIPTION OF THE DRAWINGS

The numerous objects and advantages of the present invention may be better understood by those skilled in the art by reference to the accompanying figures, in which:

FIGS. 9a and 9b shows solid phase and solution processes for a first round of synthesis for preparing libraries of compounds according to the invention;

FIG. 10 shows solid phase and solution processes for a second round of synthesis for preparing libraries of compounds according to the invention;

FIG. 13 shows solid phase and solution processes for a fifth round of synthesis for preparing libraries of compounds according to the invention.

DETAILED DESCRIPTION OF THE INVENTION

Figure 1:
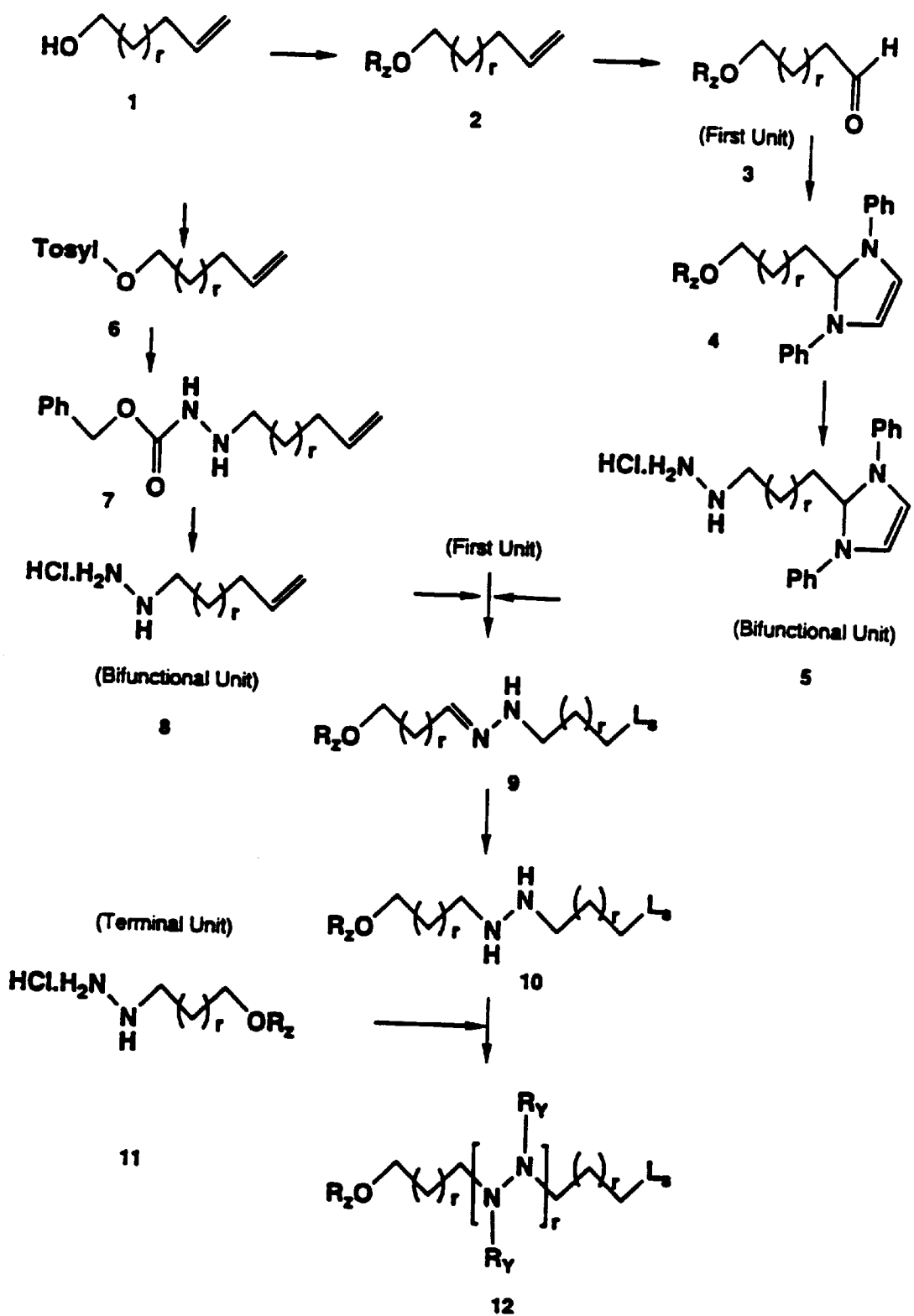
FIG. 1 shows solid phase and solution phase processes for synthesis of hydrazino-linked compounds according to the invention.

Compounds of the invention are shown by Structure I above. In Structure I, two repeating unit or monomeric unit are illustrated. Higher polymeric compounds of the invention would, of course, include additional monomeric unit of the same structure. Each of the monomeric units includes at least one nitrogen atom therein. This nitrogen atom can be one of various moieties that include a nitrogen atom as an integral part of the moiety. Preferred as such nitrogen based moiety are amine, hydroxylamine, hydrazine and sulfonamide moieties. A functional group, i.e. a "letter," can be covalent bonded to the nitrogen atom of the nitrogen moiety to introduce a point of functionality at the particular monomeric unit. When so functionalized, the nitrogen atom of the monomeric unit would be a tertiary nitrogen. Alternately a particular monomeric unit might include a "null" in place of the functional group. In one instance, this is accomplished by having the nitrogen atom as a secondary nitrogen, i.e. $R_N$ is H in the above Structure I.

Each monomeric unit can also be viewed as including a "spanner" moiety that connects between adjacent nitrogen atoms. Together, the spanner portions and the nitrogen atoms are covalently bonded into an oligomeric backbone. Thus, the spanner groups are, in essences, bi-functional in nature and alternate with the nitrogen atoms to form a backbone that includes one or more functional groups projecting there from. The backbone can be linear or it can cyclized back on itself to form a cyclic polymeric compound. It is understood that in speaking of a "nitrogen atom" and a "spanner group" in one context and of nitrogen containing moieties in a further context, certain atoms, e.g. the oxygen atom of a hydroxylamino group or the second nitrogen of a hydrazino group, of the nitrogen based moieties may for the sake of description be in a first instance part of the nitrogen based moieties and in a second instance be part of the spanner group.

The nitrogen atoms of the backbone, besides being linked together by the spanner groups, serve also as the primary site for connecting the functional groups that impart "functional" properties to the oligomeric compounds of the invention. By varying these functional groups—diversity is incorporated into the compounds of the invention. Except when they are located on the ends of the oligomeric compounds of the invention or they carry a "null" group thereon, the nitrogen atoms are trivalent in nature—that is they are connected to at least two spanner groups (one on either side) and to one functional group. In some preferred embodiments of compounds of the invention there will be from 2 to about 100 such spanner groups. In still other preferred compounds of the invention, there will be from 2 to 25 such spanner groups. A more preferred range is from 2 to 10 such groups. An even more preferred range is from 2 to 5 such groups.

In addition to linking the nitrogen atoms of the backbone together in an oligomeric structure, a particular spanner group can also carry a functional group thereon. Thus the functional groups can be located either on the nitrogen atoms of the backbone, on the spanner groups or on both the nitrogen atoms and the spanner groups. The functional groups are attached to the nitrogen atoms of the backbone or to the spanner groups with or without intervening tethers.

The functional groups appended to these oligomeric compounds of the invention can be of various structures that impart particular interactive properties to the oligomeric compounds. These functional groups can effect interactions of at least the following types: hydrogen-bond donors and acceptors, ionic, polar, hydrophobic, aromatic, electron donors and acceptors, pi bond stacking or metal binding.

The functional groups are also referenced as "letters." The use of such terminology reflects the fact that the different functional groups on the monomeric units of the compounds of the invention are positioned in sequences (either predetermined or by random selection) much like letters of the alphabet—thus the term "letter." These letters can be "reactive" or "non-reactive." By reactive, it is meant that they will interact with a target molecule in some manner (that need not but can be predefined). By non-reactive, it is meant that they are not designed to primarily interact with a target molecule, and in fact while they may interact with the target molecule, the primary purpose of the non-reactive moieties are to impart other properties to the molecule such as, but not necessary limited to, effecting up-take, distribution, metabolism or identification.

A first preferred group of functional groups according to the invention include but are not limited to aromatic moieties and substituted aromatic moieties, halogen (Cl, Br, F, I), hydroxyl (OH), thiol (SH), keto (C=O), carboxyl (COOH), amide (CONR), ethers, thioethers, amidine (C(=NH)NRR), guanidine (NHC(=NH)NRR), glutamyl CH(NRR)(C(=O)OR), nitrate ($ONO_2$), nitro ($NO_2$), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), sulfoxide (SO), sulfone ($SO_2$), sulfide (S—), disulfide (S—S), silyl, heterocyclic, alicyclic, carbocyclic, conjugate groups and metal coordination groups. Preferred substituents include substituted and unsubstituted aryl and aralkyl having from 6 to 20 carbons atoms, halogens, alcohols and ethers (OR), thiols and thioethers (SR), amines (NRR), amidines [C(=NH)NRR], guanidines [NHC(=NH)NRR], aldehydes (CH=O), acids [C(=O)OH], esters [C(=O)OR], amides [C(=O)NRR], glycine [CH($NH_2$)(C(=O) OH)], purine and pyrimidine heterocycles.

In further preferred embodiments of the invention, the reactive functionalities used as letters, suitable for use in the practice of this invention include, but are not limited to, substituted or unsubstituted heterocyclic compounds, such as substituted or unsubstituted heterocycloalkyls; amino containing groups, such as heterocycloalkylamines, polyalkylamines, imidazoles, imidazole amides, alkylimidazoles; substituted or unsubstituted aldehydes; substituted or unsubstituted acids; substituted or unsubstituted amides; substituted or unsubstituted ketones; substituted or unsubstituted ethers; substituted or unsubstituted esters; substituted or unsubstituted aralkylamino having from about 6 to about 20 carbon atoms, aminoaralkylamino having from about 6 to about 20 carbon atoms, alkyloxyaryl compounds, or allyloxyaryl compounds.

The functional groups or letters are attached to the nitrogen atoms of the backbone or to the spanner groups with or without intervening tethers. Tethers as used in the context of this invention are bivalent groups that have a first end for covalently bonding to the nitrogen atoms of the backbone or to the spanner group and a second end capable of binding a letter. Such tethers can be used to position "letters" in space with respect to the backbone or to link letters to the nitrogen atoms of the backbone wherein the letter itself does not include an active moiety capable of covalently bonding to a nitrogen of the backbone. A particularly preferred group of compound useful as tethers include, but are not limited to, $C_2$–$C_{10}$ alkyl, $C_2$–$C_{10}$ alkenyl, $C_2$–$C_{10}$ alkynyl, $C_4$–$C_7$ carbocylo alkyl or alkenyl, heterocycles, an ether having 2 to 10 carbon atoms and 1 to 4 oxygen or sulfur atoms, polyalkyl glycols and $C_7$–$C_4$ aralkyl groups.

Amine functional groups of the invention can include amines of all of the above alkyl, alkenyl and aryl groups including primary and secondary amines and "masked amines" such as phthalimide. Amines of this invention are also meant to include polyalkylamino compounds and aminoalkylamines such as aminopropylamines and further heterocycloalkylamines, such as imidazol-1, 2, or 4-yl-propylamine.

Other reactive functionalities suitable for practicing the invention include, without limitation, compounds having thiol (SH), aldehyde (C=O), or alcohol (OH) functionalities.

Heterocycles, including nitrogen heterocycles, suitable for use as functional groups include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Imidazole groups are especially preferred.

Further preferred heterocycles include the purines and pyrimidines. Purines and pyrimidines suitable for use as functional groups include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

For the purposes of this specification, in the context of the invention and in reference to the above Structure I, alkyl, alkenyl, and alkynyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl, which has further straight or branched chains attached to the carbon atoms of the straight chain. A cyclic compound, as used herein, refers to closed chain compounds—that is, a ring of carbon atoms, such as a cyclic aliphatic or aromatic compound. The straight, branched, or cyclic compounds may be internally interrupted (i.e., alkylalkoxy or heterocyclic compounds). In the context of this invention, internally interrupted means that the carbon chains may be interrupted with heteroatoms such as O, N, or S; however, if desired, the carbon chain may have no heteroatoms.

For the purposes of this specification, in the context of the invention and in reference to the above Structure I, aryl groups include but are not limited to substituted and unsubstituted aromatic hydrocarbyl groups. Aralkyl groups include but are not limited to groups having both aryl and alkyl functionality, such as benzyl and xylyl groups. Preferred aryl and aralkyl groups include, but are not, limited to, phenyl, benzyl, xylyl, naphthyl, tolyl, pyrenyl, anthracyl, azulyl, phenethyl, cinnamyl, benzhydryl, and mesityl. These can be substituted or unsubstituted. It is particularly preferred that if substituted, the substitution be meta to the point of attachment of the substitution aryl or aralkyl compound to the backbone or tether connecting to the backbone since such meta substitution isolates electronic effects of the substituent from the reactive functionality used to attached the aromatic moiety to the backbone or tether.

Such compounds as noted above may be substituted or unsubstituted. In the context of this invention, substituted or unsubstituted, means that the compounds may have any one of a variety of substituents, in replacement, for example, of one or more hydrogen atoms in the compound, or may have no substituents. Typical substituents for substitution include for example, but are not limited to, substituted with hydroxyl, alkoxy, alcohol, benzyl, phenyl, nitro, thiol, thioalkoxy, halogen, or alkyl, aryl, alkenyl, or alkynyl groups.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are known, as for example see Mellor, D. P., *Chemistry of Chelation and Chelating Agents in International Encyclopedia of Pharmacology and Therapeutics,* Section 70, The Chelation of Heavy Metals, Levine, W. G. Ed., Pergamon Press, Elmford, N.Y., 1979.

Non-reactive functionalities used as letters, such as groups that enhance pharmacodynamic properties, include groups that improve uptake, enhance resistance to enzymatic or chemical degradation, and/or strengthen sequence-specific interaction with a target molecule. Non-reactive functionalities may also enhance pharmacokinetic properties, in the context of this invention, such groups improve uptake, distribution, metabolism or excretion. Non-reactive functionalities include, but are not limited to, alkyl chains, polyamines, ethylene glycols, steroids, polyamides, aminoalkyl chains, amphipathic moieties, points for reporter group attachment, and intercalators attached to any of the preferred sites for attachment, as described above.

Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include PEG groups, cholesterols, phospholipids, biotin, phenanthroline, phenazine, phenanthridine, anthraquinone, acridine, fluoresceins, rhodamines, coumarins, and dyes.

A number of functional groups can be introduced into compounds of the invention in a blocked form and subsequently de-blocked to form a final, desired compound. In general, blocking groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. For example, amino groups can be blocked as phthalimido groups or as 9-fluorenylmethoxycarbonyl (FMOC) groups and carboxyl groups can be protected as acetyl groups. Representative hydroxyl protecting groups are described by Beaucage, et al., Tetrahedron 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX).

Solid supports according to the invention include controlled pore glass (CPG), oxalyl-controlled pore glass (see, e.g., Alul, et al., Nucleic Acids Research 1991, 19, 1527), TentaGel Support—an aminopolyethyleneglycol derivatized support (see, e.g., Wright, et al., Tetrahedron Letters 1993, 34, 3373) or Poros—a copolymer of polystyrene/divinylbenzene.

Oligomeric compounds of the invention can be synthesized with the sequence of letters predetermined or random. Thus in certain preferred embodiments, the sequence of letters is a predetermined sequence. In further preferred embodiments, the sequence of letters is random. In even further preferred embodiments, the sequence is modulated between fixed and random. This is especially useful, as for example, in certain combinatorial'strategies such as the above referenced SURF strategy.

A further advantage of this invention is the ability to synthesize oligomeric compounds that, in addition to or in place of variability in the sequences of the letters, have an asymmetric sequence of spanner units. Stated otherwise, the spanner units can also vary within an oligomeric structure. This is easily accomplished by using different compounds that eventually become incorporated as spanner units.

One preferred method of synthesizing the compounds of the invention is via a solution phase synthesis. A further preferred method of synthesizing the compounds of the invention is a solid phase synthesis.

The letters are attached to their respective monomeric units, either to the nitrogen atom of the backbone of the monomeric unit or to the spanner group of the monomeric unit. These functional groups thus provide diverse properties ("diversity") to the resulting oligomeric compounds. Such diversity properties include hydrogen-bond donors and acceptors, ionic moieties, polar moieties, hydrophobic moieties, aromatic centers, electron-donors and acceptors, pi bond stacking and metal binding. Together, the properties of the individual repeating units contribute to the uniqueness of the oligomer in which they are found. Thus, a library of such oligomers would have a myriad of properties, i.e., "diversity." Collectively, the properties of the repeating units that form an oligomer contribute to the uniqueness of such an oligomer and impart certain characteristics thereto for interaction with protein, lipid, cellular, enzymatic or nucleic acid target sites.

The oligomeric compounds of the invention can be prepared having either preselected sequences or sequences determined via combinatorial strategies. One useful combinatorial strategy is the above-noted SURF strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

Illustrative of the SURF strategy is a 2'-O-methyl oligonucleotide library (see, Ecker et. al., ibid.) shown in Table I, below. Table I describes the selection of a 2'-O-methyl oligonucleotide for binding to an RNA hairpin. The $K_D$'s, i.e., the binding constants, were determined by gel shift. "X" is used to indicate the position being varied and underlining is used to indicate positions that become fixed during successive iterations of the SURF strategy.

TABLE I

| Subsets | $K_D$ (mM) | | | |
| --- | --- | --- | --- | --- |
| | X = A | X = C | X = G | X = T |
| Round 1 | | | | |
| NNNNXNNNN | 22 | 10 | >100 | >100 |
| Round 2 | | | | |
| NNNNCNXNN | >10 | 4 | >10 | >10 |
| Round 3 | | | | |
| NNXNCNCNN | >10 | 0.5 | >10 | >10 |
| Round 4 | | | | |
| NNCXCNCNN | >10 | 0.15 | >10 | >10 |
| Round 5 | | | | |
| NNCCCXCNN | 0.08 | >1 | 0.4 | >1 |
| Round 6 | | | | |
| NNCCCACXN | 0.05 | >0.5 | 0.08 | >0.5 |
| Round 7 | | | | |
| NXCCCACAN | >0.1 | >0.1 | 0.03 | >0.1 |
| Round 8 | | | | |
| NGCCCACAX | 0.05 | 0.02 | 0.05 | 0.04 |
| Round 9 | | | | |
| XGCCCACAC | 0.03 | 0.05 | 0.02 | 0.01 |

This SURF strategy has not been previously used for libraries except those that employ naturally-occurring nucleotides as phosphodiesters or phosphorothioates as monomeric units. Other combinatorial strategies have only been previously used for libraries that employ amino acids as monomeric units.

One advantage of the present invention is that the simple design of repeating units enables combining rational drug design with screening mechanisms for thousands of compounds. This is achieved by using the compounds of the invention in a combinatorial techniques such as the SURF strategies.

The oligomeric compounds of the invention can be used in diagnostics, therapeutics and as research reagents and kits. They can be used in pharmaceutical compositions by including a suitable pharmaceutically acceptable diluent or carrier. In preferred embodiments, the compounds of the invention act as inhibitors of enzymes such as phospholipase $A_2$; as inhibitors of pathogens such as virus, mycobacterium, bacteria (gram negative and gram positive), protozoa and parasites; as inhibitors of ligand-receptor interactions such as PDGF (platelet derived growth factor), LTB4 (leukotriene B4), IL-6 and complement $C5_A$; as inhibitors of protein/protein interactions including transcription factors such as p50 ($NF_{kappa}B$ protein) and fos/jun; and for the inhibition of cell-based interactions including ICAM induction (using inducers such as IL1-β, TNF and LPS). In other preferred embodiments, the compounds of the invention are used as diagnostic reagents for each of the above noted biological entities, and as reagents in assays and as probes.

The compounds of the invention generally are prepared by coupling preselected bifunctional synthons under conditions effective to form compounds having structure I. In certain embodiments, compounds of the invention are prepared by intermolecular reductive coupling. In other embodiments, compounds of the invention are prepared by intermolecular radical addition reactions. In further embodiments, compounds are prepared by nucleophilic displacement. In each of these embodiments, free amino groups in the resulting linkage can be further functionalized. For example, the nucleophilic amino group can be reacted with a group having structure $R_L$—T—L, thereby displacing the $R_L$ leaving group and forming a covalent —N—T—L linkage.

In the reductive coupling methods, compounds having structure I are formed by coupling synthons having structures III and IV:

$$R_{N2}\text{—}\underset{\underset{R_{N1}}{|}}{N}\text{—Q—A—C(O)H} \quad \text{III}$$

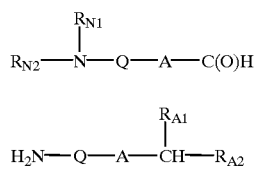

IV wherein:

$R_{N1}$ and $R_{N2}$ are, independently, amine protecting groups, or a group comprising: [N($R_N$)—Q—A—CH$_2$—]$_r$ where r is 1–100, or $R_{N1}$ and $R_{N2}$ together, form an amine protecting group; and $R_{A1}$ and $R_{A2}$ are, independently, carbonyl protecting groups, or a group comprising: [N($R_N$)—Q—A—CH$_2$—]$_r$ where r is 1–100, or $R_{A1}$ and $R_{A2}$, together, form a carbonyl protecting group.

Each $R_N$ is independently, H, —T—L, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocyclo alkyl or alkenyl, an ether having 2 to 10 carbon atoms and 1 to 4 oxygen or sulfur atoms, a polyalkyl glycol, or $C_7$–$C_{14}$ aralkyl or substituted aralkyl; a nitrogen, sulfur or oxygen containing heterocycle; and where the substitutents groups are selected from hydroxyl, alkoxy, alcohol, benzyl, phenyl, nitro, thiol,n thioalkoxy, halogen, or alkyl, aryl, alkenyl, or alkynyl groups.

The radical addition reactions can be divided into two steps. The first step involves generation of an initial radical, which undergoes the desired reaction. The second step involves removal of the radical from the reaction before the occurrence of an intervening, undesired reaction such as cross coupling.

In certain embodiments, the compounds of the invention are prepared by providing a donor synthon having structure V and an acceptor synthon having structure VI where $R_B$ is a radical generating group, generating a carbocentric radical at the —CH$_2$—$R_B$ position, and then forming an intermolecular linkage by reacting radical-bearing donor synthon V with acceptor synthon VI. Radical generating groups according to the invention include I, OC(S)O—$C_6H_5$, Se—$C_6H_5$, OC(S)O—$C_6F_5$, OC(S)O—$C_6Cl_5$, OC(S)O—(2,4,6—$C_6Cl_3$), Br, NO$_2$, Cl, OC(S) S—Me, OC(S)O—(p-CH$_4$F), bis-dimethylglyoximatopyridine cobalt, OC(S) $C_6H_5$, OC(S)SCH$_3$, OC(S)-imidazole, and OC(O)O-pyridin-2-thione.

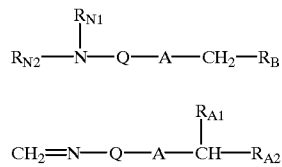

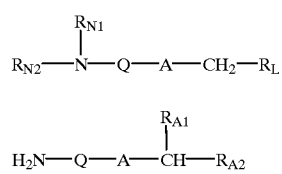

The nucleophilic displacement (alkylation) reactions involve reacting a first synthon VII bearing a leaving group, $R_L$, with a second synthon VIII bearing a nucleophilic nitrogen moiety under conditions effective to displace the leaving group and form the above-identified linkages.

Leaving groups according to the invention include chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups.

The linkages of the invention can be formed by selecting a formyl-derivatized compound (e.g., structure III) as an upstream synthon and an amino-derivatized compound (e.g., structure IV) as a downstream synthon.

Formyl-terminated compounds such as structure III can be formed via several synthetic pathways. One preferred method utilizes a radical reaction of the corresponding xanthate-terminated compound. The xanthate compound is treated with 2,2'-azobisisobutrylonitrile (AIBN), and tributyltin styrene in toluene. Subsequently, the styrene derivative is hydroxylated and cleaved to furnish a formyl group. Alternately, formyl-terminated compounds can be synthesized from a cyano-terminated compound by techniques well known in the art. Terminal formyl groups can be blocked in a facile manner, for example, utilizing O-methylaminobenzenthiol as a blocking group. The formyl blocking group can be deblocked with silver nitrate oxidation.

An alternate method of preparing formyl-terminated compounds employs tosylation of a terminal hydroxyl group, which on iodination followed by cyanation with KCN in DMSO will furnish a nitrile. Reduction with DIBAL-H gives the desired formyl-terminated compound. In yet another method, a terminal C=C bond is oxidized with OsO$_4$ and cleavage of the resulting diol with NaIO$_4$ gives the desired formyl functionality.

Hydroxylamino terminated compounds such as those having structure IV (Q=O) can be prepared by treating the corresponding hydroxyl compound with N-hydroxyphthalimide, triphenylphosphine and diethylazodicarboxylate under Mitsunobu conditions to provide an O-phthalimido derivative. The free hydroxylamino compound can be generated in quantitative yield by hydrazinolysis of the O-phthalimido derivative.

Hydrazino-terminated compounds such as those having structure IV (Q=NH) can be prepared by treating hydroxyl-terminated compounds with tosyl chloride in pyridine to give an O-tosylate derivative. Treatment of benzylcabazide with O-tosylate will furnish a benzylcarbazide derivative, which on hydrogenation provides the free hydrazino moiety for reductive coupling.

Amino-terminated compounds such as those having structure IV (Q=CH$_2$) can be synthesized by treating the corresponding hydroxyl-terminated compound with Ph$_3$P, CBr$_4$ and LiN$_3$ according to the procedure of Hata, et al., *J. Chem. Soc. Perkin* 1 1980, 306, to furnish a terminal azide. Reduction of the azido group with tributyltin hydride provides the desired amino functionality.

Coupling of structures III and IV then is effected to furnish a dimeric unit having an imine or oxime linkage. This linkage then is reduced in situ with NaCNBH$_3$ to furnish a —C—N— linked unit.

Oligomers containing a uniform backbone linkage can be synthesized using CPG-solid support and standard synthesizing machines such as Perkin Elmer Applied Biosystems Inc. 380B and 394 and Milligen/Biosearch 7500 and 8800s. The initial monomer is attached, via an appropriate linker, to a solid support such as controlled pore glass or polystyrene beads. In sequence specific order, each new monomer (e.g., structure III or IV) is attached either by manual manipulation or by the automated synthesizer system. In the case of a methylenehydrazine linkage (Q=N), the repeating nucleoside unit can be of two general types: a linear structure with a protected aldehydic function at one end and a C-hydrazinomethyl group at the opposite end, or a structure bearing a terminal hydrazino group and a protected C-formyl group. In each case, the conditions that are repeated for each cycle to add the subsequent base include: acid washing to remove the terminal aldehydo protecting group; addition of the next molecule with a methylenehydrazino group to form the respective hydrazone connection; and reduction with any of a variety of agents to afford the desired methylene-hydrazine linked CPG- or polystyrene-bound structure. One such useful reducing agent is sodium cyanoborohydride.

A preferred method is shown in FIG. 1. This method utilizes a solid support to which a linear molecule having a protected aldehyde or an aldehyde precursor at its terminal end is attached. The terminal aldehyde can be suitably protected with various groups, such as described by Greene and Wuts in *Protective Groups in Organic Synthesis*, John Wiley & Sons, Inc., 1991, pp 175–223. In one preferred method, the aldehyde group is protected with N,N'-diphenyl imidazolidine, which can be cleaved with aqueous HCl as described by Giannis, et al. *Tetrahedron* 1988, 44, 7177. 2,3-Dihydro-1,3-benzo-thiazole is yet another preferred protecting group for aldehyde functionality and is cleaved by AgNO$_3$ at neutral pH (see, e.g., Trapani, et. al., *Synthesis* 1988, 84). More preferably, a terminal vinyl group is oxidized with OsO$_4$ and cleaved with NaIO$_4$ to yield a free aldehydo group.

A bifunctional synthon having a protected aldehydo group at one end (the masked coupling end) and a hydrazino group at the opposite end (the reactive coupling end) can be coupled under acidic conditions with a linear aldehyde attached to the solid support. The intermediate hydrazone then is reduced with NaBH$_3$CN to furnish a hydrazino linkage attached to the solid support.

Subsequently, bisalkylation of the hydrazino moiety via an appropriate halide or aldehyde provides a N,N-substituted hydrazine linked to the solid support. Thereafter, the cycle can be repeated by the addition of bifunctional synthon under acidic conditions, reduction, and alkylation of hydrazine moiety to create a polymeric molecule of a desired sequence connected by one or more substituted hydrazino linkages. In some preferred embodiments of this invention, the final unit utilized for coupling can bear an ionic linkage to provide water solubility for such molecules.

One preferred process employs an aldehyde-protected synthon attached to the solid support. Attachments can be effected via standard procedures as described by R. T. Pon in Protocols For Oligonucleotides And Analogs, Chapter 24, Agrawal, S., ed., Humana Press, Totowa, N.J., 1993.

As an alternative, a solution phase synthesis of substituted hydrazino linked linear molecules can be accomplished via hydroxyl protected synthons, such as shown in FIG. 1 (R$_Z$=hydroxyl protecting group or solid support) utilizing a t-butyl diphenylsilyl group.

Figure 4:
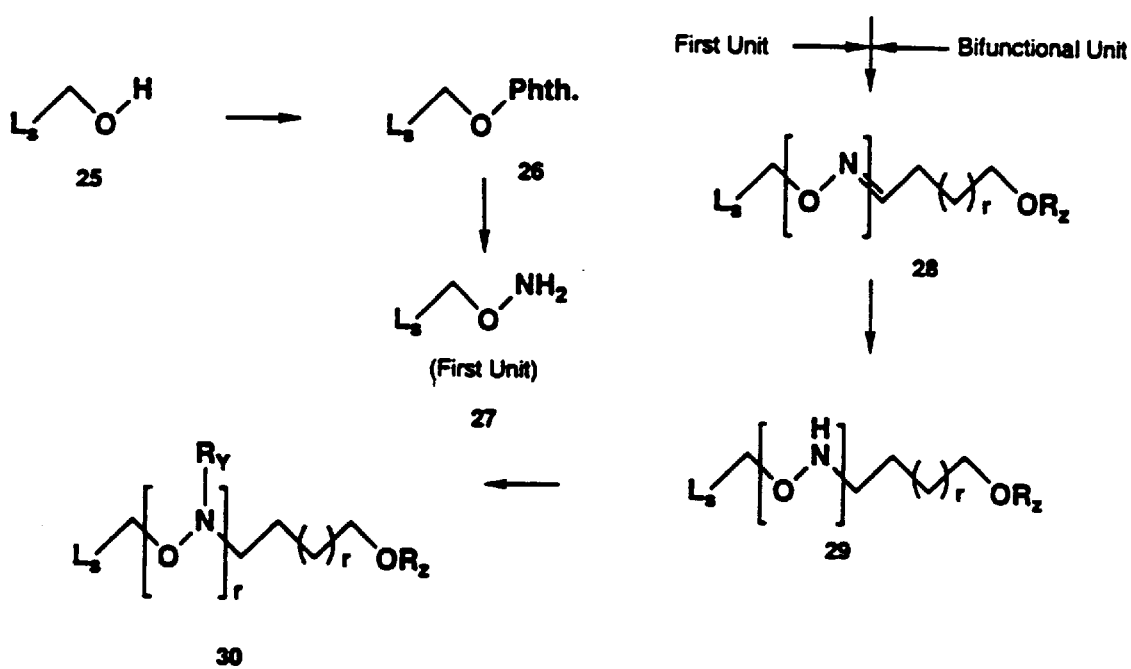
FIG. 4 shows solid phase and solution processes for synthesis of hydroxylamino-linked compounds according to the invention.

A further method of synthesizing N-substituted hydroxylamine linked linear molecules is depicted in FIG. 4 (L$_S$=a linker attached to solid support, or a protecting group, such as t-butyldiphenylsilyl). This method also employs a solid support to which a linear molecule having an O-phthalimido group at its terminal end is attached. A further bifunctional unit that has an aldehyde functionality at the coupling end and an O-phthalimido group at the growing end is utilized as the middle block via repeating cycles. The synthesis of polymeric structures can be stopped by use of a terminating unit that bears a hydroxyl protecting group rather than a phthalimido group. A wide variety of hydroxyl protecting groups can be employed in the methods of the invention. In general, protecting groups render chemical functionality inert to specific reaction conditions, and can be appended to and removed from such functionality in a molecule without substantially damaging the remainder of the molecule. Representative protecting groups are described by Beaucage, et al., *Tetrahedron* 1992, 48, 2223.

The O-phthalimido group attached to the support is hydrazinolyzed with methylhydrazine to generate a reactive O-amino group. Acid catalyzed coupling of the resulting bifunctional unit provides an oxime linked support. The oxime linkage can be reduced with NaBH$_3$CN/acetic acid to yield a hydroxyl amino linkage, which is then alkylated with appropriate functionality. Alternately, the coupled unit can be treated with methyl hydrazine and the coupling with bifunctional unit repeated until an oligomer of desired length is obtained. The multiple oxime linkages thus created can be reduced in one step utilizing NaBH$_3$CN/AcOH to create free O-amino groups, which can be further substituted uniformly with appropriate functionality.

In a similar manner, a solution phase synthesis of such polymeric molecules connected via substituted hydroxylamino linkages utilizes the coupling/reduction/alkylation hydrazinolysis steps in a sequential order, starting with a hydroxyl protected molecule.

The radical-based methods of the invention generally involve "nonchain" processes. In nonchain processes, radicals are generated by stoichiometric bond homolysis and quenched by selective radical-radical coupling. It has been found that bis(trimethylstannyl)benzopinacolate and bis(tributylstannyl)benzopinacolate (see, e.g., *Comprehensive Organic Synthesis*: Ed. by B. M. Trost & J. Fleming, Vol. 4, pp 760)—persistent radicals—can be used to enhance the radical-radical coupling and reduce cross-coupling. It will be recognized that a persistent radical is one that does not react with itself at a diffusion-controlled rate. Hillgartner, et al., *Liebigs. Ann. Chem.* 1975, 586, disclosed that on thermolysis (about 80° C.) pinacolate undergoes homolytic cleavage to give the suspected persistent radical (Ph$_2$C˙OSnMe$_3$), which stays in equilibrium with benzophenone and the trimethylstannyl radical (Me$_3$Sn$^•$) It is believed that the Me$_3$Sn$^•$ radical abstracts iodine from radical precursors such as iodo-terminated compounds having structure V to give radical-terminated intermediates. The radicals then add to immino acceptors such as structure VI to yield a —C—C—N— linkage.

At high concentrations the initial radical can be trapped by coupling prior to addition, and at low concentrations the adduct radical can begin to telomerize. It is believed that a three molar equivalent excess of pinacolate provides satisfactory results for such couplings. The efficiency of radical reactions is highly dependent on the concentration of the reagents in an appropriate solvent. Preferably, the reaction mixture contains benzene, dichlorobenzene, t-butylbenzene, t-butyl alcohol, water, acetic acid, chloroform, dichloromethane, carbon tetrachloride, or mixtures thereof. The solvent should contain a combined concentration of about 0.1 to about 0.4 moles/liter of radical precursor and acceptor, preferably about 0.1 to about 0.2 moles/liter. It has been found that best results are obtained using benzene solutions containing about 0.2 moles/liter of radical precursor and acceptor.

Figure 5:
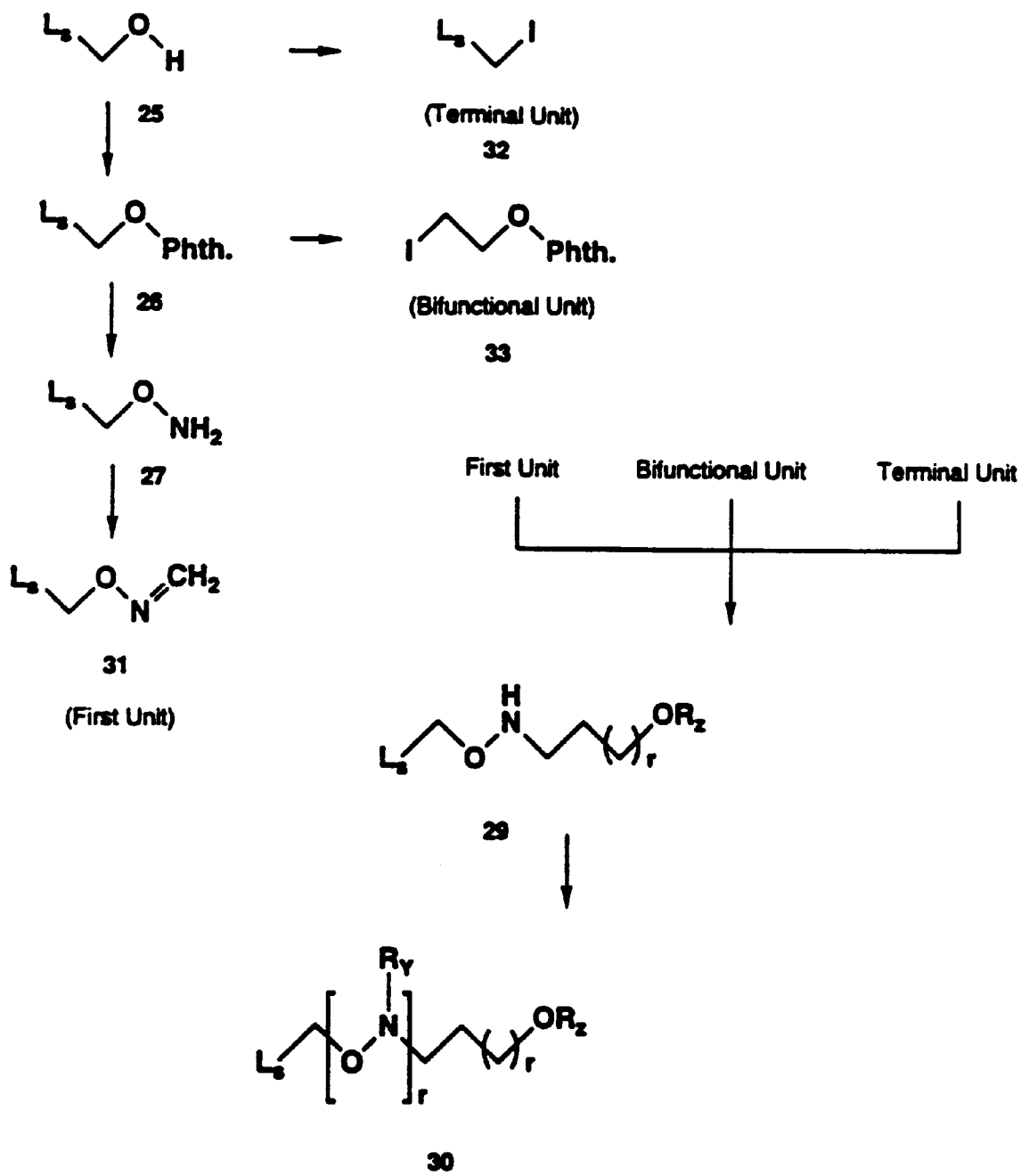
FIG. 5 shows a synthetic scheme for synthesis of hydroxylamino-linked compounds according to the invention by radical coupling methodology.

As exemplified in FIG. 5, the radical coupling of an oxime ether 31 as an acceptor with radical precursor 33 occurs in the presence of bis(trimethylstannyl)benzopinacolate in refluxing benzene. The reaction is carried out under argon and a 35–50% isolated yield of the product is obtained after purification. The hydroxylamino linkages thus obtained can be alkylated with an appropriate functionality. Subsequently, the hydroxyl group is deblocked and treated with N-hydroxyphthalimide under Mitsunobu conditions to yield an O-phthalimido derivative. Hydrazinolysis and formylation of the latter compound gives an oxime ether functionality at the reactive end of the molecule. Therefore, a radical coupling cycle can be repeated with high chemoselectivity to yield an oligomer or polymeric unit linked via one or more substituted hydroxylamino linkages. The chain elongation can be terminated at any point during the described method by avoiding the Mitsunobu reaction at the hydroxyl function.

The desired method essentially can be transferred from solution to solid phase systems by utilizing an oxime unit linked to a support via a linker.

The radical coupling methodology also can employ a bifunctional unit, as depicted in FIG. 5. Thus, coupling between an oxime linked to a support and the bifunctional unit under the described conditions will provide a hydroxylamino linked molecule. This compound can be alkylated in a standard manner to yield a N-substituted molecule. Subsequently, deblocking of the phthalimido group with methyl hydrazine liberates a free O-amino group, which on treatment with formaldehyde gives a terminal oxime. The oxime can be used in another round of coupling with an iodo derivative. In this manner the synthesis is more convenient, due to the Mitsunobu reaction prior to coupling. Radical coupling cycles can be repeated as often as needed until a polymer of desired length is obtained. The elongation usually is terminated by using a last unit, as shown in FIG. 5, that bears a protected hydroxyl group. The foregoing procedure is highly adaptable to solution phase chemistry in a similar manner.

The synthesis of libraries of oligomeric compounds of the invention is illustrated in FIGS. 8–13. The individual compound species in these libraries are generated via combinatorial methodologies. Illustrated in these figures is the preparation of intermediates used for the synthesis of libraries of compounds of the invention and combinatorial methodologies for synthesizing such libraries utilizing these intermediates.

The libraries are prepared by general procedures that results in nitrogen based combinatorial libraries. The active species of the libraries are determined using a SURF deconvolution procedure. Both solution phase and solid phase synthesis are used to create the libraries. Example 8 of this specification illustrates the general combinatorial synthesis and deconvolution procedures used to create the libraries. Example 9 illustrates the synthesis of intermediates used in both solution phase and solid phase synthesis of libraries. Creation of a full library of compounds and determination of such active species via a SURF deconvolution is illustrated in Example 10. Example 11 illustrates the activation of solid phase support intermediates for attachment to controlled pore glass supports, i.e. CPG. Example 12 illustrates the attachment of the activated intermediates on to CPG solid support for use in solid phase possesses that parallel the solution phase processes illustrated in Example 10. The solid phase synthesis is effected in the same manner as the solution phase synthesis with the exception that bead splitting is substituted for the solution splitting of the solution phase synthesis. Example 13 illustrates loading of solid phase intermediates onto organic resins.

Example 10 illustrates the preparation of libraries via Schiff's base alkylation whereas Example 14 illustrates the preparation of libraries via alkylation reaction using halide intermediates. Example 15 illustrates a further method for preparing the libraries via acylation using acid halides intermediates. Example 16 illustrates alternate methods for the preparation of "extenders," (that form the spanners or portions thereof). Examples 17 and 18 illustrate further "extenders." These are amino acid types and oxyamine acid types, respectively.

In FIGS. 8–13, the synthesis and combinatorialization of 1,4,9,14,19-pentaaza-8,12,18-trioxanonadecane with nitrogens 1,4,9,14,19 combinatorialized with four letters is illustrated. A total of 1024 compounds are prepared in four sets of 256 compounds each. Four sets of linear polyamine/oxyamines, compounds 122a–d, are formed in round 1. Each set has positions 1 through 5 (positions 1 and 5 are primary nitrogens where as positions 2, 3 and 4 are secondary oxyamine nitrogens) substituted in a combinatorial manner, i.e. combinatorialized, with equal amounts of the letters. The following structures identify the position numbers and the nomenclature numbering used in the FIGS. 8–13 and their accompanying examples.

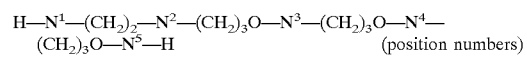
(position numbers)

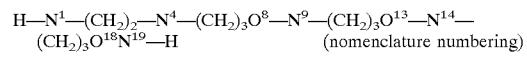
(nomenclature numbering)

For illustrative purposes aromatic letters, specifically benzyl, m-methylbenzyl, m-nitrobenzyl, and m-methoxybenzyl moieties, are used as letters. The precursors compounds for these letters as well as for multitudes of other such letters are commercially available from various commercial sources. Other letters, for example alkyl, alkenyl, alkynyl, amino acid side chains, nucleobases and the like, are utilized in the same manner. As illustrated in the Figures, at the completion of synthesis of the library, each set has position 5 (a primary oxyamine nitrogen) substituted exclusively with a known one of the four letters. For illustrative purposes, as shown in the Figures, the letter selected to be fixed is placed in the molecule last. This was selected as position 5 for fixing in the first round synthesis of the libraries. For the illustrative compounds that have five combinatorial sites with one site fixed, the iterative deconvolution process (SURF) requires four subsequent rounds of synthesis to be performed to identify the most active molecules. Each round of synthesis is performed to allow the position selected to be fixed as the last fixed position. Other position selection approaches can be taken, e.g. the first selected position can be fixed. For illustrative purposes, to fix a position last in rounds 3–6, the acid labile sulfenyl triphenyl methyl moiety is utilized to protect the designated nitrogen atom until combinatorilization of other positions and fixing of known positions is completed. Other protective groups can also be utilized.

The linear polyamine/oxyamines are prepared by two sets of sequential reactions: submonomer addition of a letter to a secondary nitrogen and extension (elongation) of the chain via an extender to provide another secondary nitrogen for combinatorialization via submonomer chemistry (first step). The purpose of repeating these sequential sets of reactions is to liberate/provide a reactive secondary amine (the next position to be combinatorialized) in the growing chain in the absence of other reactive centers and to extend the molecular length (and thus the number of combinatorial positions) in the polyamine/oxyamine chain.

The key starting material for this particular combinatorial chemistry library is 1-(tert-butoxycarbonyl)-9-phthaloyl-1, 4,9-triaza-8-oxa-decane, i.e. t-Boc—NH—$(CH_2)_2$—NH—$(CH_2)_3$—O—N-phthaloyl, 106. This same compound can also be used as a key starting material for preforming the combinatorial synthesis on a solid support. This is illustrate where BG=solid support, e.g. 1-(BG)-9-phthaloyl-1,4,9-triaza-8-oxa-decane, i.e. BG—NH—$(CH_2)_2$—NH—$(CH_2)_3$—O—N-phthaloyl, 109.

For the solution phase synthesis, the material 106 is protected at one end (position 1) with the acid labile tert-butoxycarbonyl group (t-Boc) and the terminal oxyamine (position 3) is protected by a base labile phthaloyl group (acid dephthalyation can also be used if desired). The internal secondary oxyamine (position 2) is unprotected and available for submonomer chemistry as shown in compound 106. In addition, 106 with its internal secondary amine protected with a sulfenyltriphenyl protecting group is employed in preparations of latter rounds of deconvolution.

The basic chemistry employs three types of tertiary nitrogens, a primary amine, a primary oxyamine and a secondary oxyamine, each of which is protected with a suitable protecting group. For illustrative purposes, the protective groups selected for protecting these nitrogens are tert-butoxycarbonyl, a sufenyltriphenyl and a phthaloyl. The tert-butoxycarbonyl (t-Boc) and the sulfenyltriphenyl [S(Ph)$_3$] moieties are remove by various differential acid conditions and the phthaloyl moiety is typically removed with hydrazines (basic conditions) and with certain acid conditions. For addition of letters, the monomer and the submonomer approaches are utilized. The submonomer approach requires the addition of a letter intermediate to one of the tertiary nitrogens. This can be accomplished by several chemistries including, but not limited to, "Schiff's base reductive alkylation," alkylation, e.g., with alkyl-halides, and amide bond formation with acid, acid halides, esters, etc.

The Schiff's base reductive alkylation is described in Examples 9 and 10. Aralkyl halide chemistry is described in Example 14 and acylation chemistry is described in Example 15. Moieties required for submonomer letter addition are aldehydes, ketones, primary and secondary alkyl halides, sulfonates, triflates, diazonium salts, acids, acid halides, esters, etc. These same reactive moieties are employed to extend the chain when attached to an alkyloxyphalimide or a substituted alkyloxyphalimide (both in monomer and submonomer approaches). Starting materials for these reaction are commercial chemical reagents available from various commercial chemical supply houses. They can be used as purchased without further modification.

The illustrative oligomeric compound having five site for combinatorialization and four letters, is treated via submonomer chemistry to combinatorializes position 2 with four letters by a split solution procedure. Each letter is reacted separately with 106. After purification, if needed, an equal molar amount of each pure compound bearing a different letter is mixed together to provide a mixture of four compounds with position 2 combinatorialized with four letters.

Position 3 is deprotected (dephthaloylation with methylhydrazine), followed by reductive alkylation (Schiff's base formation and reduction of imino intermediate with NaCNBH$_3$) with a selected extender. As illustrated in the figures, the selected extender is N-(3-hydroxypropionaldehyde)phthalimide, 105, i.e. OHC(CH$_2$)$_2$O-NPhth. A variety of other extenders can be employed including aldehydes, ketones, halides, acid halides and the like. Preferred representative extenders include:

| | | |
|---|---|---|
| OHCCH$\phi$-N$_3$ | BrCH$\phi$CH$\phi$-N$_3$ | ClCOCH$\phi$-N$_3$ |
| OHCCH$\phi$-NO$_2$ | BrCH$\phi$CH$\phi$-NO$_2$ | ClCOCH$\phi$-NO$_2$ |
| OHCCH$\phi$-NPhth | BrCH$\phi$CH$\phi$-NPhth | ClCOCH$\phi$-NPhth |
| OHCCH$\phi$O—NPhth | BrCH$\phi$CH$\phi$O—NPhth | ClCOCH$\phi$O—NPhth |
| OHCCH$\phi$N$\phi$-NPhth | BrCH$\phi$CH$\phi$N$\phi$-NPhth | ClCOCH$\phi$N$\phi$-NPhth |
| OHCCH$\phi$SO$_2$—NPhth | BrCH$\phi$CH$\phi$SO$_2$—NPhth | ClCOCH$\phi$SO$_2$—NPhth | where Phth is phthalimide and $\phi$ is a letter (functional group), a tethered letter or H; and provide that in those compounds having a single $\phi$, then $\phi$ is a letter or a tethered letter; and in those compounds having multiple $\phi$s, then at least one $\phi$ is a letter or a tethered letter and the remaining are either H, a further letter or tethered letter. Other preferred representative extenders are of the formula:

where:

Phth and $\phi$ are as defined above;

$R_X$ is HCO, ketone, halide, CO-halide; and $R_Y$ is N$_3$, NO$_2$, NPphth, ONPhth, N$\phi$NPhth and SO$_2$NPhth.

Halides in this instances are Br, Cl and I.

Modified extenders allows the addition of letters through the monomer approach. A further group of preferred extenders, some of which include modification such as side chains and the like, include compounds of the structure:

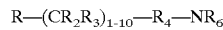

where:

R is OHC— (aldehydes), OR$_1$C— (ketones) halogen, HO$_2$C—, and halogen-CO— (acid halide);

R$_2$ and R$_3$ are H, alkyl, substituted alkyl, aryl, substituted aryl, aralkyl, substituted aralkyl, heterocycle, moiety as found in α-position of amino acids, halogen, amine, substituted amines, hydroxy, alkoxyls, substituted alkoxyls, SH, and substituted thioalkoxyls;

R$_4$ is O, CH$_2$, CR$_2$R$_3$, NH, NR$_5$ and SO$_2$,

R$_5$ is alkyl, substituted alkyl, aryl and substituted aryl;

R6 is phthaloyl, H$_2$, N$_2$, O$_2$, H Acetyl, diAcetyl, methyleneamino, or an amino protecting group; and CR$_2$R$_3$ are a chain of 3 atoms or more containing C, N, O, S and their various oxidation states.

The reaction with the extender provides a reactive secondary nitrogen ready for combinatorialization. The sequential set of reaction are repeated again. This is continued until the desired length is obtained (for the number of combinatorial sites, for the length of molecule, for the desired molecular weight, etc.). As illustrated in the examples, compound 117 (having four sites for combinatorialization) is extended one additional time to provide five site for combinatorialization. Then position 1 is liberated with acid conditions. The resulting primary amine is treated separately with each of the four letters. In this case, reduction of the intermediate imino (—CH=N—) moiety is not performed until the final step to allow a cleaner reactions when position 5 is subsequently fixed with each specific letter. The final set of reactions for the preparation of this particular library provides a fixed letter at position 5. In this case position 5 is not combinatorialized—it is not a mixture of the four letters. Each set of the library has a known letter at position 5. Thus four subsets of libraries, (mixtures of compounds) are obtained. This approach employed a split solution process utilizing SURF deconvolution (iterative screening).

Extension (elongation) of the chain provides another secondary nitrogen for combinatorialization via submonomer chemistry. The purpose of repeating these sequential sets of reactions is to liberate/provide a reactive secondary amine (the next position to be combinatorialized) in the growing chain in the absence of other reactive centers and to extend, via an extender, the molecular length (and thus the number of combinatorial positions) in the polyamine/oxyamine chain. In addition to extending the length of the oligomeric compound, the extender could also carry a letter substituted in the molecule between the reactive group, e.g. aldehyde, and the protected amine, oxyamine or other nitrogen species. The extenders can be utilized with various chemistries including the Schiff's base reductive alkylation (with aldehydes and ketones) of Example 10, alkylation (with alkyl halides) of Example 14 and with acylation (acid halides) following reduction of the amide bond of Example 15. Various types and mixtures of extenders can be used in the elongation reaction.

EXAMPLE 1

Reductive Coupling

I. Solution phase Synthesis of an Oligomeric Molecule Linked Via Hydrazino Linkages (FIG. 1)

A. Synthesis of a 'First Unit', 1-O-(t-butyldiphenylsilyl)-butyraldehyde-1-ol, 3 (R$_Z$=t-butyldiphenylsilyl (TBDPS), r=1)

A mixture of 4-penten-1-ol (10 mmol), t-butyldiphenylsilylchloride (12 mmol), imidazole (25 mmol) and dry DMF (50 ml) is stirred at room temperature for 16 h under argon. The reaction mixture is poured into ice-water (200 ml) and the solution extracted with CH$_2$Cl$_2$ (2×200 ml). The organic layer is washed with water (2×200 ml) and dried (MgSO$_4$). The CH$_2$Cl$_2$ layer is concentrated to furnish a gummy residue, which on purification by silica gel chromatography gives silylated 4-penten-1-ol. The silylated compound is oxidized with OsO$_4$ (1 mmol) and N-methylmorpholine oxide (20 mmol) in diethyl ether (40 ml) and water (20 ml) at room temperature for 18 h. NaIO$_4$ (30 mmol) solution in water (2 ml) is added to the above solution and stirring is continued for 12 h. The aqueous layer is extracted with diethyl ether (2×200 ml) and evaporation of combined organic layers gives crude aldehyde 3.

B. Synthesis of a 'Bifunctional Units', 4-Penten-1-hydrazine hydrochloride, 8, and Imidazolidine Derivative, 5

Treatment of 4-Penten-1-ol with tosylchloride in pyridine will furnish tosylated 6, which on treatment with benzylcarbazate in dimethylacetamide as described in Example 1 of Ser. No. 08/039,979, filed Mar. 30, 1993, provides the carbazyl derivative 7. Hydrogenation with Pd/C in MeOH/HCl provides the title compound 8 as hydrochloride salt.

The aldehyde group of 3 is protected as N,N'-diphenylimidazolidine derivative utilizing the procedure of Giannis, et. al., Tetrahedron 1988, 44, 7177, to furnish 4. Subsequently, 4 is treated with Bu$_4$NF/THF to deblock the silyl protecting group. The hydroxyl group of the latter compound is transformed into a hydrazino group via the two step procedure described above to yield title compound 5.

C. Synthesis of a 'Terminal Unit', 3-O-(t-butyldiphenylsilyl)-1-(hydrazine)-propanol hydrochloride (11, R$_Z$=TBDPS, r=1).

The title compound is prepared from propane-1,3-diol, via selective silylation with t-butyl-diphenylsilylchloride, followed by treatment with benzylcarbazate and hydrogenation as described above in Example 1(I)(B).

D. Solution Phase Coupling of a 'First Unit' and a 'Bifunctional Unit'

Aldehyde 3 and hydrazino derivative 8 are coupled in dry CH$_2$Cl$_2$/MeOH/AcOH as described in Example 3 of Ser. No. 08/039,979, filed Mar. 30, 1993, to furnish an intermediate hydrazone 9 (L$_S$=CHO). The latter product is reduced with NaBH$_3$CN/AcOH to furnish a hydrazino linked molecule 10 (L$_S$=N,N'-diphenylimidazolidino). Subsequently, is bis-alkylated with N1-methylformylthymine to yield 12 (R$_Z$=H, L$_S$=CH$_2$OH, R$_Y$=N1-ethylthymine).

The reactive aldehyde moiety of 12 can be regenerated by acid treatment to deblock the N,N-diphenyl imidazolidine. If compound 5 is used in place of compound 8, the aldehyde moiety can be regenerated by OsO$_4$ oxidation/NaIO$_4$ cleavage of the terminal vinyl moiety (i.e., L$_S$=CH=CH$_2$). Thus, another round of coupling is carried out followed by reduction and alkylation with tether or tether plus a new ligand. In this manner, one can place a variety of ligands on a single molecule, separated by an appropriate linear chain, an important feature for recognition of macromolecules.

The coupling may be terminated at any point by utilizing a terminal unit, such as molecule 11. This compound provides a hydrazino end to couple with an aldehyde but bears a protected hydroxyl group, which will be deblocked to provide an hydroxyl moiety.

In addition, one may choose to attach a phosphate or phosphonate group via terminal hydroxyl group in order to provide higher solubility to oligomeric unit.

II. Automated Solid Support Synthesis of an Oligomeric Molecule Linked Via Hydrazino Linkages (FIG. 1)

A. Synthesis of a 4-Penten-1-ol Attached to Solid Support

4-Penten-1-ol is attached via a succinyl linker onto CPG following standard protocol (e.g., R. T. Pon in Protocols For Oligonucleotides And Analogs, Chapter 24, Agrawal, S., ed., Humana Press, Totowa, N.J., 1993.). The CPG bound 4-penten-1-ol 2 (R$_Z$=CPG, r=1) is oxidized with OsO$_4$, and the product treated with NaIO$_4$ to yield 3 with a free aldehydo group. Next, a reductive coupling with bifunctional unit such as 5 furnishes 10 bound on CPG. Subsequent alkylation with a tether such as chloroethane furnishes 12. In a similar manner, the deblocking of imidazolide with acid and repeated coupling with another bifunctional unit allows the linear growth of the hydrazino linked oligomer, until a desired length of the molecule is obtained.

The foregoing solid support synthesis can be transferred to a robotic or automated synthesis technology as, for example, in the generation and rapid screening of libraries of molecules (see, e.g., Zuckermann, et. al., *J. Am. Chem. Soc.* 1992, 116, 10646).

EXAMPLE 2

Figure 2:
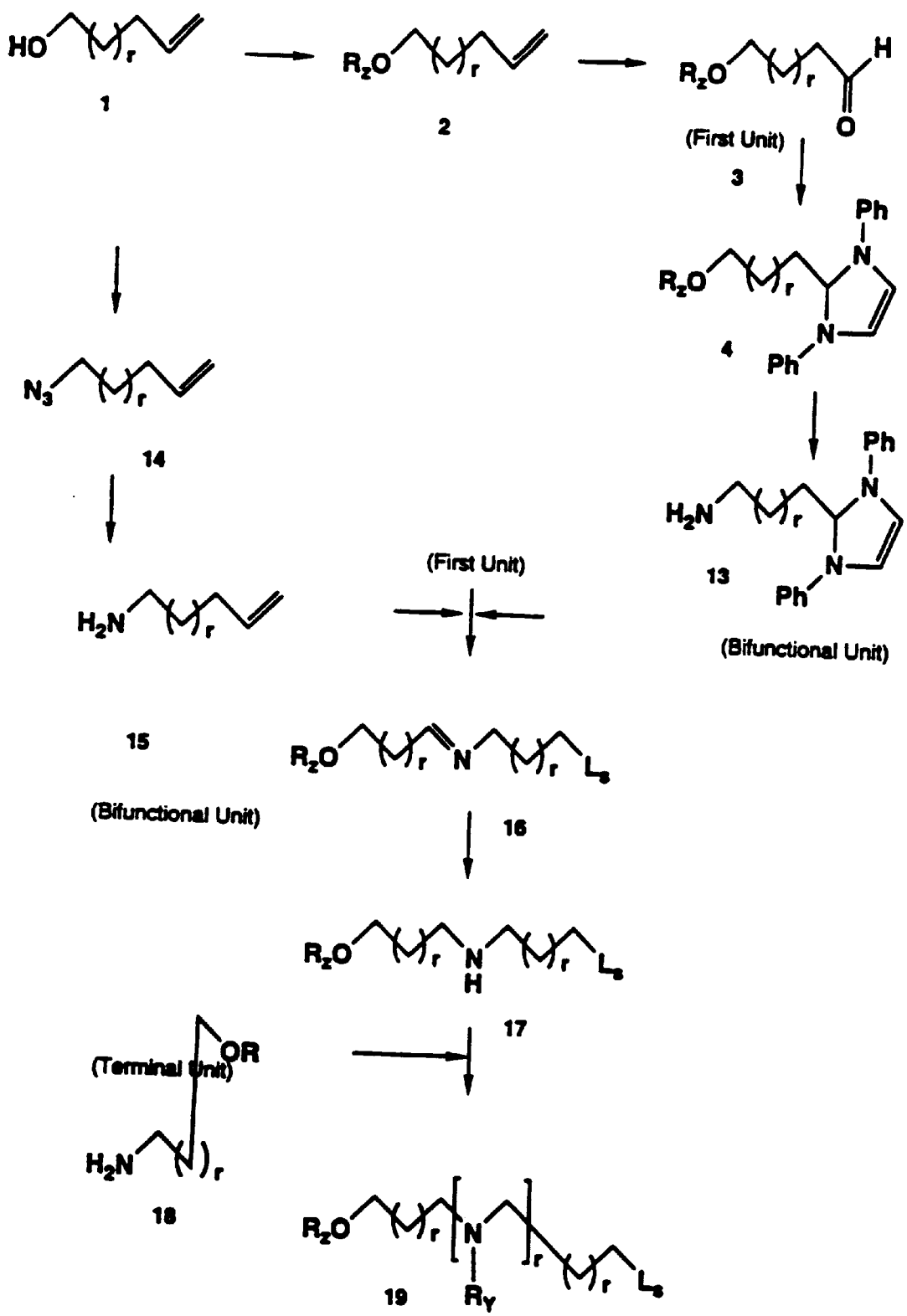
FIG. 2 shows solid phase and solution phase processes for synthesis of amino-linked compounds according to the invention.

Reductive Coupling
Solution Phase Synthesis of Oligomeric Molecule Linked Via Amino Linkages (FIG. 2)

The 'first unit' for this synthesis is the same as used in Example 1, above.

A. Synthesis of Bifunctional Units, 4-Pentenyl-1-amine, 15, and 3-(N,N$^1$-diphenyl imidazolidine)-butyl-1-amine, 13.

Treatment of 4-penten-1-ol 1 (r=1) with methlysulfonyl chloride in pyridine at 0° C. affords the sulfonate, which on treatment with lithium azide in DMF gives azido derivative 14. Reduction of 14 with tributyltin hydride in dimethyl acetamide furnishes title compound 15.

Yet another bifunctional unit 13 is prepared in five steps, starting from 1. The hydroxyl group initially is protected with t-butyldiphenyl silyl group and the product, on oxidative cleavage using $OsO_4/NaIO_4$, gives aldehyde 3 ($R_Z$=TBDPS). The latter compound is further transformed to the imidazolidine derivative 4, which on desilylation followed by conversion of the hydroxyl group to an amino group via an azide, furnishes 13 (see, e.g., Lin, et. al., *J. Med. Chem.* 1978, 21, 109).

B. Coupling of First and Bifunctional Units

To a stirred solution of aldehyde 3, amine 13 and acetic acid in $CH_2Cl_2$ is added $NaBH(OAc)_3$ under argon. Alternatively, amine 15 is used in place of amine 13. The suspension is stirred for 3 h and the reaction mixture, on work up as described in Example 17 of Ser. No. 08/039,979, filed Mar. 30, 1993, gives the dimeric 17 ($L_S$=CHO or CH=CH$_2$). Reductive amination is performed thereon generally in accordance with *Tet. Lett.*, 1990, 31, 5595. Subsequently, the amino functionality is reductively alkylated with N1-methylformylthymine to provide 19 ($R_Z$=H, $L_S$=CH$_2$OH, $R_Y$=N1-ethylthymine). Coupling can be repeated to obtain compounds of formula 19 with varying length (e.g. r=1–20).

EXAMPLE 3

Figure 3:
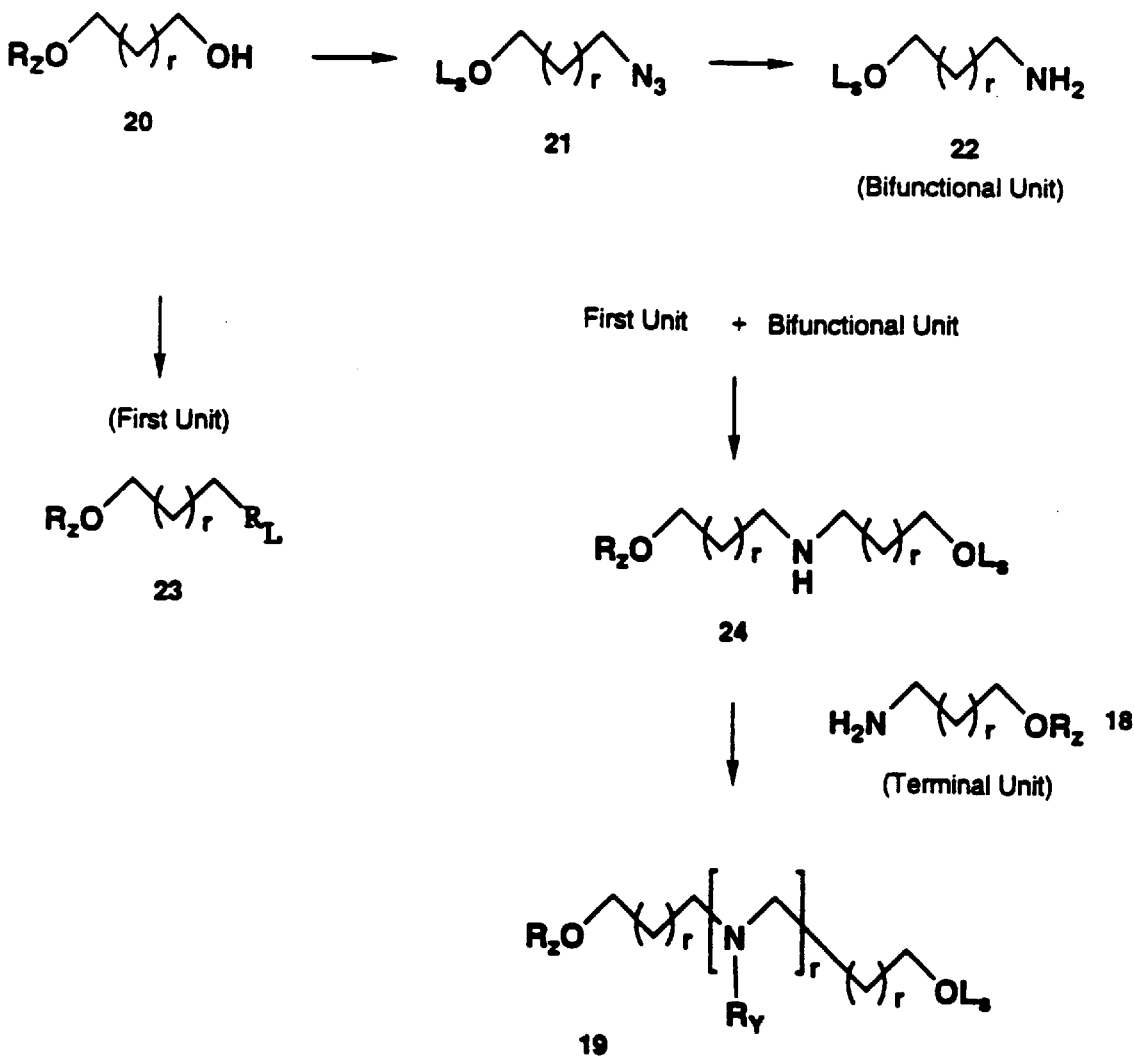
FIG. 3 shows further solid phase and solution phase processes for synthesis of amino-linked compounds according to the invention.

Nucleophilic Coupling
Oligomeric Molecules Linked Via Amino Linkages (FIG. 3)

FIG. 3 describes a general method for assembly of amino linked linear molecules. Further methods are described by Niitsu, et. al., *Chem. Pharm. Bull.* 1986, 31, 1032.

A. Synthesis of First Unit, 23

The title compound is prepared from commercial 1,3-propanediol, which on monosilylation with t-butyldiphenylsilylchloride gives protected 20 ($R_Z$=TBDPS, r=1). The free hydroxyl group of 20 is then converted into a tosyl leaving group as described by J. March in Advanced Organic Chemistry, Reactions, Mechanisms, and Structure, page 352, John Wiley & Sons, New York, 1992 to furnish 23 ($R_L$=O-tosyl). Other suitable leaving groups include brosylates, nosylates, mesylates or halides.

B. Synthesis of Bifunctional Unit, 22

Treatment of 3-bromo-1-propanol with lithium azide in DMF furnishes 3-azido-1-propanol, which on silylation provides 21 ($L_S$=TBDPS, r=1). The azido group of 21 is reduced to provide the bifunctional unit 22. The nitrogen nucleophile at the reactive end of compound 22 is blocked with a 9-fluorenylmethoxycarbonyl (FMOC) group, and the hydroxyl group at the dormant end is deblocked and transformed into a reactive ester as in Example 3(A), above to provide 23 ($L_S$=tosyl).

C. Coupling of First Unit and Bifunctional Unit

Compounds 22 and 23 are reacted in presence of an appropriate base to furnish a secondary amine 24 as the product. Subsequently, amino group of 24 is reductively alkylated with N1-methylformylthymine to yield compound 19 ($R_Z$=H, $L_S$=H, $R_Y$=N1-ethylthymine). In order to continue with coupling, the blocking group from hydroxyl moiety is removed and the resulting hydroxyl group connected to an active ester moiety. Another round of coupling takes place, followed by alkylation/deblocking/esterification steps until a molecule of desired length is obtained.

EXAMPLE 4

Reductive Coupling
Solution Phase Synthesis of an Oligomeric Molecule Linked Via Hydroxylamine Linkages (FIG. 4)

A. Synthesis of a 'First Unit', Amino-O-benzylalcohol, 27

Title compound 27 is prepared in two steps starting from commercial benzyl alcohol 25 ($L_S$=phenyl). In the first step, Mitsunobu reaction of 25 with N-hydroxyphthalimide/triphenylphosphine/diethylazodicarboxylate gives an o-phthalimido derivative 26. Treatment of 26 with methylhydrazine gives 27.

B. Synthesis of a 'Bifunctional Unit', 3

Title compound 3 is prepared in a manner described in Example 1, above.

C. Coupling of a 'First Unit' and a 'Bifunctional Unit'

A mixture of 27, 3, and acetic acid is stirred in $CH_2Cl_2$ for 1 h at room temperature. The solvent is evaporated to furnish the crude oxime 28, which on reduction with $NaBH_3CN$/AcOH (as described in Example 11 of Ser. No. 08/039,979, filed Mar. 30, 1993) furnishes 29. The amino group of 29 is further reductively alkylated with N1-methylformylthymine to yield 30 ($R_Z$=H, $L_S$=phenyl, $R_Y$=N1-ethylthymine).

Alternatively, the terminal phthalimido group of 28 is deblocked with 3% methylhydrazine in $CH_2Cl_2$ and the o-amino group is coupled with another bifunctional unit under acidic conditions. This cycle of treatment can be repeated with methylhydrazine and coupling until an oligomer of desired length is formed. All oxime linkages can be reduced in one step using $NaBH_3CN$/AcOH treatment, as described above. A common tether or a tether and ligand then can be attached in a single alkylation step to yield 30. However, this methodology provides a means to obtain an oligomeric unit with similar tether or tether and ligand placed onto amino group.

In another method, the oxime linkage is reduced immediately after coupling and attachment of the tether or tether and ligand is effected. This modification in the procedure allows placement a tether or tether and ligand of choice at a preselected position within an oligomer.

EXAMPLE 5

Radical Coupling
I. Solution Phase Radical Coupling Methodology for Linear Hydroxylamino Linked Oligomers (FIG. 5)

A. Synthesis of a 'First Unit', O-Benzylformaldoxime, 31 ($L_S$=phenyl)

The title compound is prepared from benzyl alcohol following a procedure generally in accordance with Hart, et. al., *J. Am. Chem. Soc.* 1988, 110, 1631.

B. Synthesis of Bifunctional Unit, 2-Iodo-1-O-phthalimidoethanol, 33

Ethyleneglycol is selectively protected with t-butyldiphenylsilyl group generally in accordance with Nair, et. al., *Org. Prep. Procedures Int.* 1990, 22, 57. A Mitsunobu reaction of the monosilylated ethyleneglycol with N-hydroxyphthalimide in a manner described by Debart, et. al., *Tet. Lett.* 1992, 33, 2645, furnishes 2-O-tert-butyldiphenylsilyl-1-O-phthalimidoethanol. Deblocking of the silyl group of this compound with $Bu_4NF/THF$, followed by iodination provides the desired bifunctional molecule 33.

C. Coupling of a 'First Unit' and a 'Bifunctional Unit'

Bis(trimethyltstannyl)benzopinacolate mediated intermolecular free-radical carbon-carbon bond-forming reaction is carried out in benzene generally in accordance with Example 85 of Ser. No. 08/039,979, filed Mar. 30, 1993, with 31 as a radical acceptor and 33 as a radical precursor to yield a linear hydroxylamine 29 ($R_Z$=Phth.).

The amino group of hydroxylamine 29 is reductively alkylated with N1-methylformylthymine to yield 30 ($R_Z$Phth., $R_Y$=N1-ethylthymine). Treatment of 30 with 3% methylhydrazine/$CH_2Cl_2$ provides a terminal O-amino group, which on formylation with 1 mol equivalent of HCHO/MeOH provides an oxime functionality at the reactive end of 30 ($R_Z$=N=$CH_2$) for the next round of coupling. Thus, the chain length is extended by reacting 30 with 33 in a similar manner, followed by alkylation, hydrazinolysis and formylation to obtain the desired length of the oligomer. The final, terminal unit 32 is employed when no more chain elongation is required. Deblocking with $Bu_4NF$ will furnish a terminal hydroxyl group in oligomeric 30.

II. Solid Support Synthesis

As described in Example 1(II)(A), above, oligomeric molecules are prepared by attaching 31 ($L_S$=$CH_2OH$) to a solid support such as CPG or polystyrene via an appropriate linker. Once the oligomer of desired length is obtained, the product is cleaved from the support to furnish fully deblocked product, 30.

EXAMPLE 6

Reductive Coupling

Figure 6:
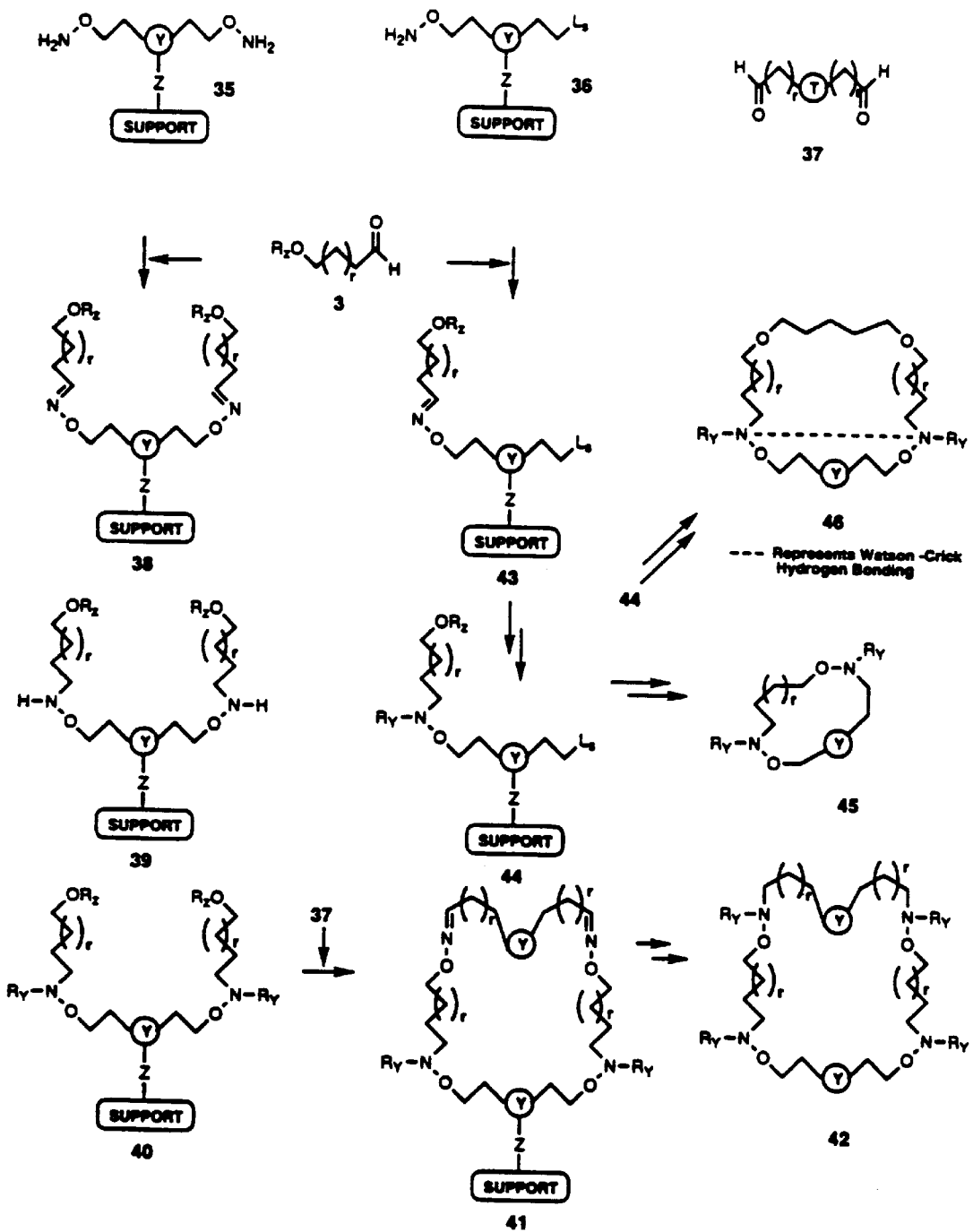
FIG. 6 shows solid phase processes for synthesis of duplex, hairpin, stem-loop, and cyclic hydroxylamino-linked compounds according to the invention.

Solid Support Synthesis of Covalently Linked Duplex Structures as Hairpins/Stem-Loops and Cyclic Oligomeric Structures Via Hydroxylamino Linkages (FIG. 6)

A. Cyclic Oligomers

An appropriate solid support, such as 35 (Y=phenyl) is prepared from trisubstituted benzene following a double Mitsunobu reaction described in *Tet. Lett.* 1992, 33, 2645 and loading of the product via succinyl linker (Z) onto a CPG support (see, e.g., R. T. Pon in Protocols For Oligonucleotides And Analogs, Chapter 24, Agrawal, S., ed., Humana Press, Totowa, N.J., 1993.). The CPG bound material is packed into a 1 µM column and attached to an ABI DNA synthesizer 380 B model. Bis-phthalimido groups are deblocked with 3% N-methyl hydrazine/$CH_2Cl_2$ solution to liberate desired bis-O-amino moiety, 35. Then, bifunctional reagent 3 ($R_Z$=TBDPS) is employed with 5% $AcOH/CH_2Cl_2$ to give bis-oxime 38 (r=1). Deblocking with N-methyl hydrazine and coupling with 3 is repeated until an oligomeric bis-oxime of desired length is obtained. The CPG loaded 40 is removed from the synthesizer and treated with $ACOH/NaCNBH_3$ to yield reduced hydroxyl amine 39. Subsequently, all amines are reductively alkylated with N1-methylformylthymine to provide 40 ($R_Y$=N1-ethylthymine). The terminal bis-phthalimido groups of 40 are deblocked with N-methyl hydrazine and final conjugation with bis-aldehyde 37 provides circularized 41, which can be further reduced, alkylated and removed from CPG to yield appropriate circular oligomers, such as 42.

B. Circular/Dumbbelled Oligomers

The method set forth in Example 6(I)(A), above, can be further modified to produce molecules that are constructed as linear strands but that on partial self-hybridization assume defined secondary structures.

Heterobifunctional solid support 36 (Y=phenyl, Z=succinyl, $L_S$=N,N'-diphenyl imidazolidino) is prepared from trisubstituted benzene according to the procedures of Examples 1(I)(A) and 6(I)A). The support bears a protected aldehydo group on one end, a succinyl linker attached to the CPG support on a second end, and an O-amino functionality on a third end. Coupling of 3 with 36 provides oxime 43. The product 43 is reduced with $NaCNBH_3$/EtOH solution, followed by alkylation with N1-methylformylthymine to provide a ligand 40 ($R_Y$=N1-ethylthymine) with hydrogen bonding capacity. Similarly, deblocking with N-methyl hydrazine, followed by coupling with 3, and reductive alkylation provides a linear sequence bearing nucleic acid bases (A,C,G,T) in a defined order. Elongation of this oligomer is terminated when an appropriate length is achieved. The oligomer is detached from the CPG and purified by HPLC. The pure oligomer is able to self-hybridize to provide either circular or dumbbell structures of any length.

C. Hairpin/Stem-Loop Duplexes

In order to prepare partially or fully self-complementary molecules, synthesis is commenced with a molecule bearing two functionalities. One of these functionalities is the reactive end of the molecule and the other remains dormant/protected. Therefore, a heterobifunctional molecule is attached to the CPG to give protected 36, which is deblocked with N-methyl hydrazine to yield 36 with a free O-amino group. As in Example 6(I)(B), above, coupling with 3 in presence of acetic acid provides oxime 43. In two steps, the oxime is reduced and alkylated with an appropriate nucleic acid base (such as A,C,G,T) via a tether to furnish 44. The chain is elongated utilizing a three step process (deblocking, then coupling, then reductive alkylation) until an oligomer of desired length is obtained. Finally, the linear molecule is deblocked from CPG and dissolved in salt-buffer to provide a self complementary secondary structure as per the preorganized nucleic acid bases.

The protected end of the molecule is deblocked and utilized for a site-specific cross-linking on the complementary strand. Such cross-linked molecules are expected to provide additional conformational and structural stability to maintain a duplex hairpin or stem-loop or dumbbelled shape.

EXAMPLE 7

Figure 7:
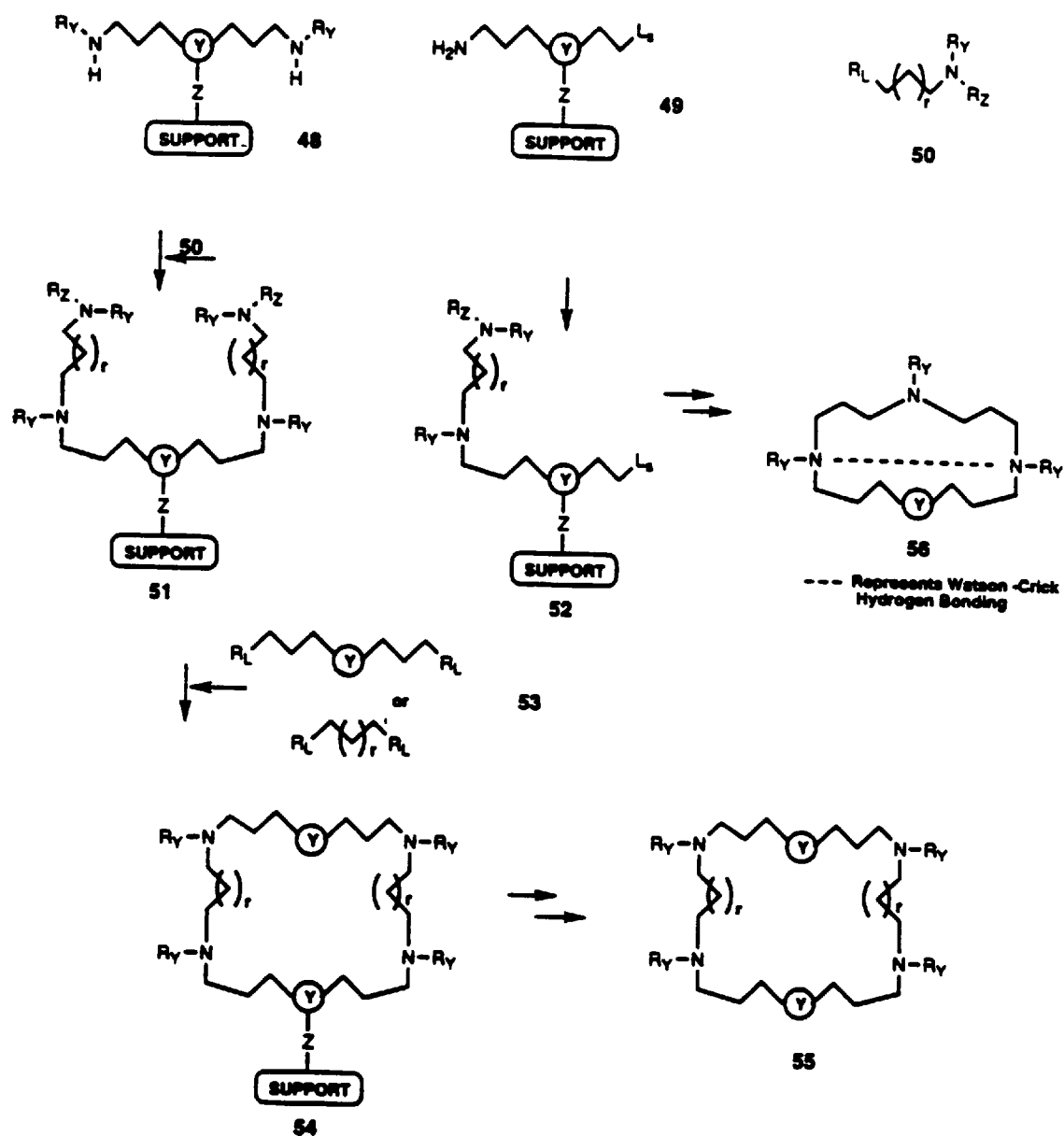
FIG. 7 shows solid phase processes for synthesis of duplex, hairpin, stem-loop, and cyclic amino-linked compounds according to the invention.

Solid Support Synthesis of Covalently Linked Duplex/Hairpins/Stem-Loops and Cyclic Oligomers Via Amino Linkage FIG. 7 describes one method for assembly of amino linked duplexes or circular oligomers. Tuladhar, et. al., *Tet. Lett.* 1992, 33, 2203, describes a synthetic route for the preparation of poly-N-$N^1$-dimethylethylenediamines, which method can be adapted for preparation of the title oligomers.

A. Circular Polyamine, 55

A bis-N-alkylated phenyl amine bearing a tether, T, and a ligand, L, is conjugated to CPG via standard procedures (see, e.g., R. T. Pon in Protocols For Oligonucleotides And Analogs, Chapter 24, Agrawal, S., ed., Humana Press, Totowa, N.J., 1993.) to provide 48 (Y=phenyl, Z=succinyl, $R_Y$=N1-alkylated pyrimidine bases or N9-alkylated purine bases). A complete set of appropriately alkylated amine building blocks 50 ($R_L$=O-tosyl, $R_Y$=N1-ethylthymine, $R_Z$=FMOC) next are prepared with a leaving group and protected secondary amine at opposite ends. Nucleophilic displacement of the leaving group of 50 by bis-N-alkylated 48 in presence of an appropriate base, such as $K_2CO_3$ or triethylamine results in formation of branched 51. The protecting group of the bis-amino function is removed and yet another round of base catalyzed coupling furnishes a longer oligomer. Thus, repetition of deblocking and coupling provides a molecule of desired length. To close the loop or tie the two amino branched, compound 53 having bis-leaving groups ($R_L$) are employed to provide a circularized oligomer 54. The oligomer is then deblocked from the support in the standard manner as is utilized in solid phase oligonucleotide synthesis (see, e.g., Oligonucleotide Synthesis, Gait, M. J., ed., IRL Press, Oxford, 1984.)

Alternatively, 51 is deblocked after a desired length is achieved to provide a linear oligomer. This oligomer is circularized by template-directed coupling, wherein a short complementary oligomer is employed to hybridize the loose ends and then carry out the coupling with 53 to provide compound 55. Kool, et. al., *J. Chem. Soc. Chem. Commun.* 1991, 1161, have reported similar ligation of reactive ends (utilizing a template) to yield circularized products.

B. Hairpin and Stem-Loops Linked Via Polyamines

As described in Example 6(I)(C), above, self-complementary hairpin and stem-loop structures are prepared in accordance with FIG. 7. Synthesis is accomplished by alkylation of N-alkyl amine 50 ($R_L$=I) with monoamine 49 ($L_S$=N,N'-diphenyl imidazolidino) to furnish 52. Use of an iodo leaving group in 50 is preferred, due to high coupling efficiency. Also preferred is use of a bifunctional reagent 50 which already bears a functional group residue attached via a tether. Thus, it is possible to incorporate appropriate ligands, e.g. heterocyclic bases or substituted aryl groups, one at a time to introduce the desired recognition element into the growing oligomer. Once an oligomer of expected length is obtained, it is removed from the support by standard methods.

The oligomer is allowed to anneal under appropriate salt concentrations to provide a hairpin or stem-loop structure. The development of these methods for cationic polyamine synthesis are attractive because their unique interaction with anionic biological target molecules and presence of an active uptake system in a variety of cell types.

EXAMPLE 8

General Procedure for Linear Tertiary Nitrogen Combinatorial Libraries and SURF Deconvolution Description of general process This example describes the general procedure for creation and deconvolution of a library of tertiary nitrogen based oligomeric compounds. Specific synthetic details corresponding to solution phase and solid support phase synthesis utilizing the procedure of this general description, alternate extenders and extender synthesis are set forth in companion Examples 9 to 18 below.

In reference to FIGS. 8 to 13 and to the companion examples, illustrated is the synthesis of a 1,4,9,14,19-pentaaza-8,12,18-trioxanonadecane with nitrogens 1,4,9,14,19 combinatorialized with four benzyl moieties as letters. A total of 1024 compounds are prepared in four sets of 256 compounds each. The procedures describe the preparation of the four sets of linear polyamine/oxyamines compounds 122a–d (round 1, FIG. 9). Each set has positions 1 through 5 (positions 1 and 5 are primary nitrogens where as positions 2, 3 and 4 are secondary oxyamine nitrogens) substituted in a combinatorial manner, i.e. combinatorialized, with equal amounts of the letters. For illustrative purposes, benzyl, m-methylbenzyl, m-nitrobenzyl, and m-methoxybenzyl moieties are the selected letters. The precursors compounds for the letters all are commercially available compounds purchased from Aldrich Chemicals, Milwaukee, Wis. At the completion of synthesis of the library, each set has position 5 (a primary oxyamine nitrogen) substituted exclusively with a known one of the four letters. In the initial approach, the letter selected to be fixed is placed in the molecule last. For illustrative purposes position 5 was selected as the fixed position in the first round synthesis of the libraries (FIG. 9). The iterative deconvolution process (SURF) requires four subsequent rounds of synthesis (FIGS. 10–13) to be performed to identify the most active molecules. Each round of synthesis is performed to allow the position selected to be fixed as the last fixed position. Other position selection approaches can be taken, e.g. the first selected position is fixed. To fix a position last in rounds 3–6, the acid labile sulfenyl triphenyl methyl moiety is utilized to protect the designated nitrogen atom until combinatorialization of other positions and fixing of known positions is completed.

The linear polyamine/oxyamines are prepared by two sets of sequential reactions: submonomer addition of a letter to a secondary nitrogen and extension (elongation) of the chain to provide another secondary nitrogen for combinatorialization via submonomer chemistry (first step). The purpose of repeating these sequential sets of reactions is to liberate/provide a reactive secondary amine (the next position to be combinatorialized) in the growing chain in the absence of other reactive centers and to extend the molecular length (and thus the number of combinatorial positions) in the polyamine/oxyamine chain.

Figure 8:
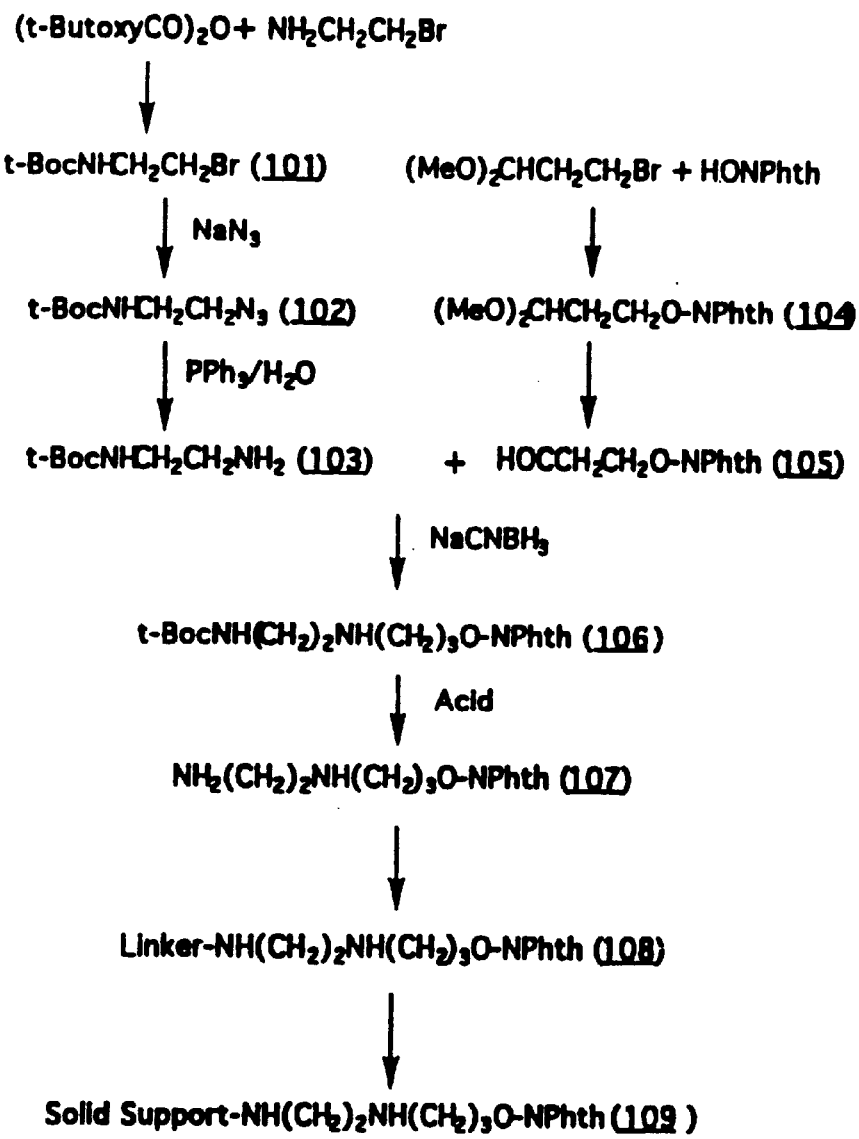
FIG. 8 shows solid phase and solution processes for synthesis of certain intermediate compounds for the preparation of libraries of compounds according to the invention.
Figure 11:
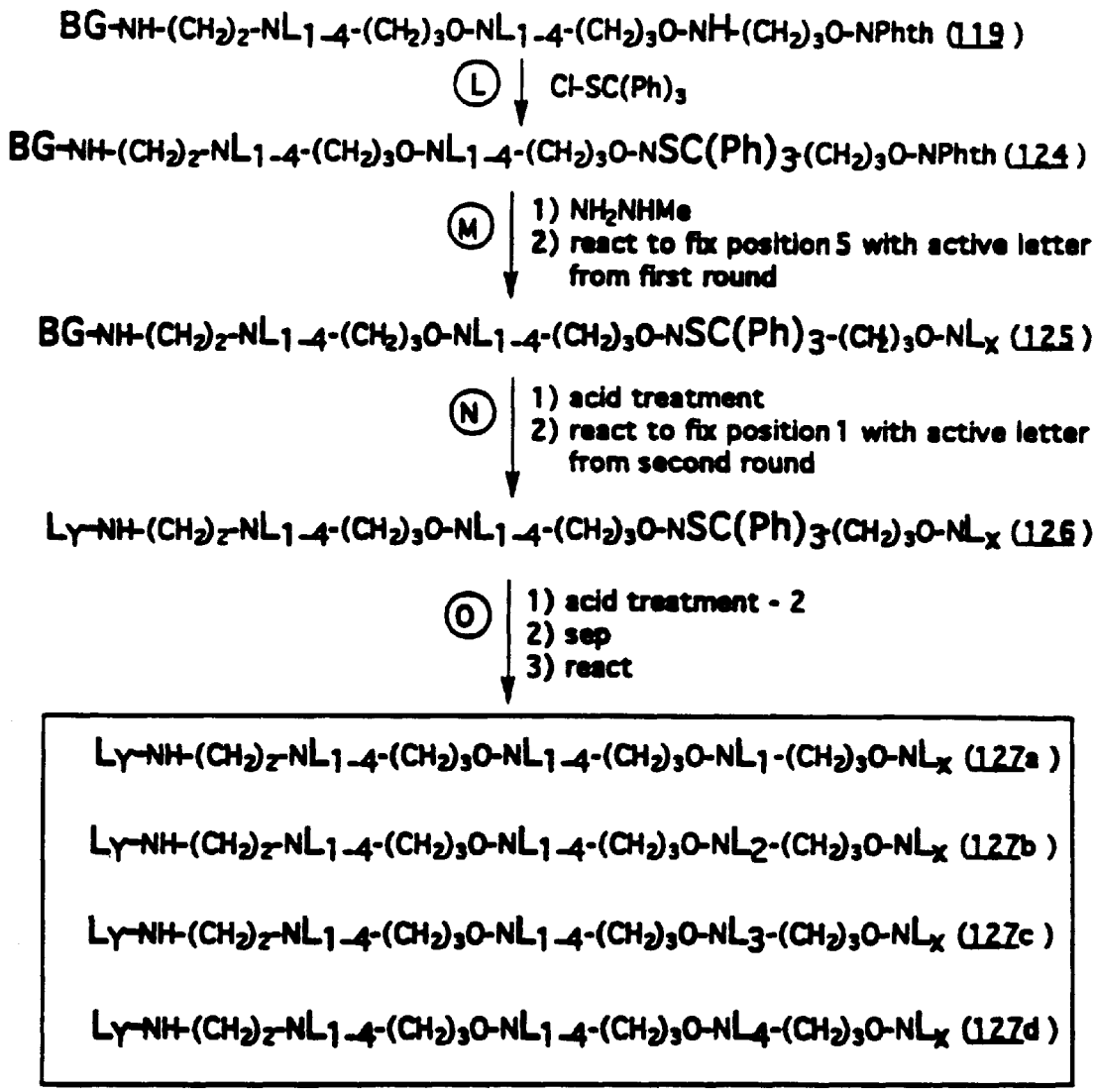
FIG. 11 shows solid phase and solution processes for a third round of synthesis for preparing libraries of compounds according to the invention.
Figure 12:
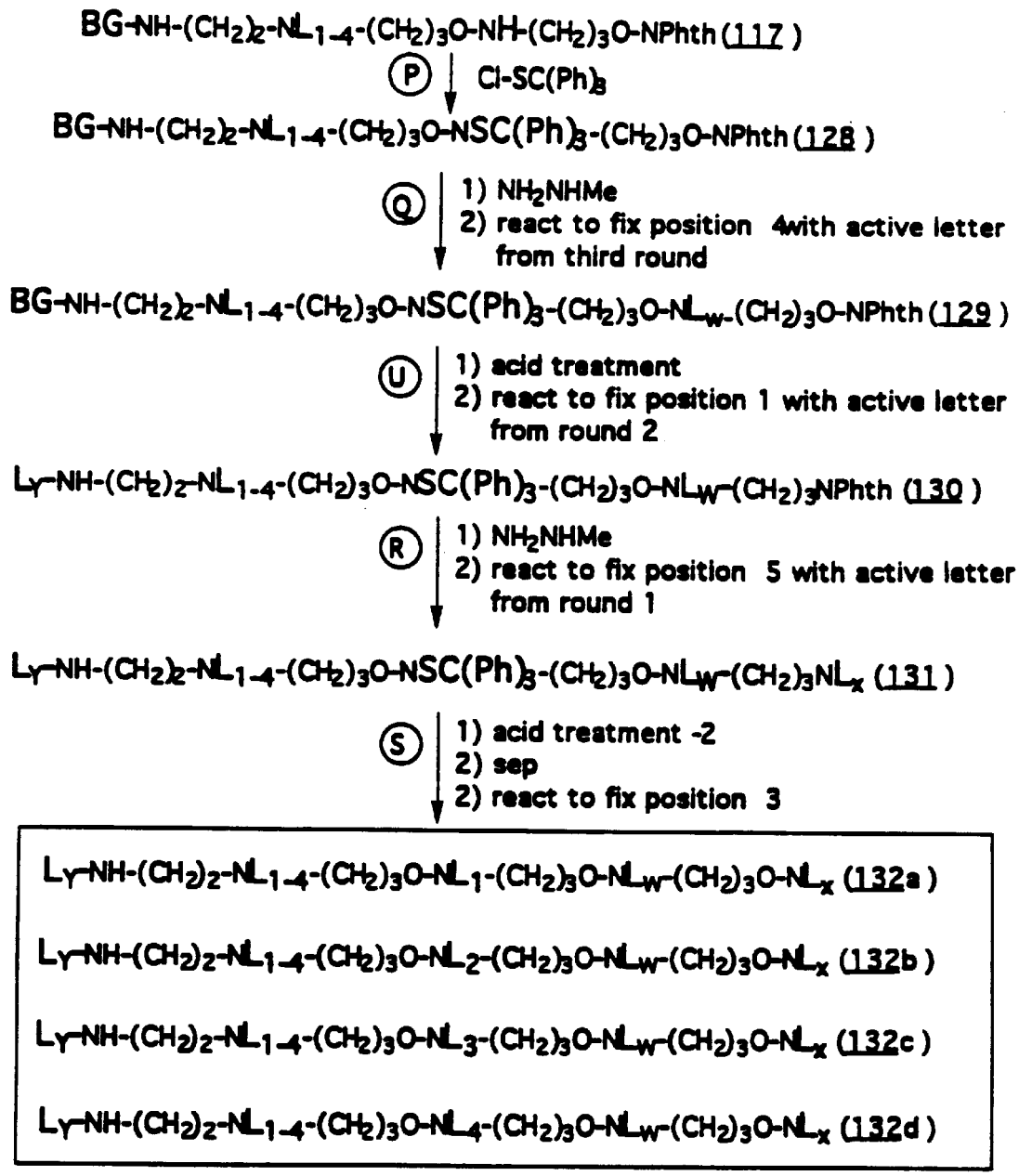
FIG. 12 shows solid phase and solution processes for a fourth round of synthesis for preparing libraries of compounds according to the invention.

The key starting material for this particular combinatorial chemistry library is 1-(tert-butoxycarbonyl)-9-phthaloyl-1,4,9-triaza-8-oxa-decane [t-Boc-NH—$(CH_2)_2$—NH—$(CH_2)_3$—O—N-phthaloyl, 106, where BG=t-Boc in the figures. This synthesis is depicted in FIG. 8. Solid phase synthesis of combinatorial libraries is effected in the same manner as depicted in FIG. 8 using compounds set forth in Examples 11 and 12. In this instance the same key intermediate starting compounds are used for effecting the combinatorial synthesis on a solid support where BG=solid support, e.g. 1-(BG)-9-phthaloyl-1,4,9-triaza-8-oxa-decane [BG-NH—$(CH_2)_2$—NH—$(CH_2)_3$—O—N-phthaloyl, 109].

For the solution phase synthesis, the compound 106 is protected at one end (position 1) with the acid labile tert-butoxycarbonyl group (t-Boc) and the terminal oxyamine (position 3) is protected by a base labile phthaloyl group (acid dephtholyation can also be used if desired). The internal secondary oxyamine (position 2) is unprotected and available for submonomer chemistry as shown in compound 106. In addition, compound 106 with its internal secondary amine protected with a sulfenyltriphenyl, compound 133, is employed in preparations of latter rounds of deconvolution.

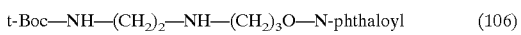
t-Boc—NH—$(CH_2)_2$—NH—$(CH_2)_3$O—N-phthaloyl    (106)

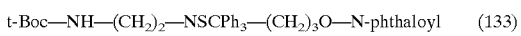
t-Boc—NH—$(CH_2)_2$—NSCPh$_3$—$(CH_2)_3$O—N-phthaloyl    (133)

In preparing libraries of compounds, advantage is taken of having three different tertiary nitrogens (a primary amine and a primary oxyamine and a secondary oxyamine) and using protecting groups to alternately protect or expose these nitrogen atoms such that they can be functionalized with various letters. The selected protecting groups are tert-butoxycarbonyl (t-Boc) and the sulfenyltriphenyl [$(S(Ph)_3$] moieties that are remove by various differential acid conditions and the phthaloyl moiety that is typically removed with hydrazines (basic conditions) and with certain acid conditions. For addition of letters, the monomer and the submonomer approaches are utilized. The submonomer approach requires the addition of a letter intermediate to one of the tertiary nitrogens. This is accomplished by several chemistries including "Schiff's base reductive alkylation," alkylation, e.g., with alkyl halides, and amide bond formation with acid, acid halides, esters, etc. The Schiff's base reductive alkylation is described in Examples 9 and 10. Other chemistries is described in Examples 14 and 15. Moieties required for submonomer letter addition are aldehydes, ketones, primary and secondary alkyl halides, sulfonates, triflates, diazonium salts, acids, acid halides, esters, etc. These same reactive moieties are employed to extend the chain when attached to an alkyloxyphalimide or a substituted alkyloxyphalimide (both in monomer and submonomer approaches). Starting materials for these reaction are commercial chemical reagents available from various commercial chemical supply houses. They are used as purchased without further modification.

First Set of Reactions

Submonomer chemistry combinatorilizes position 2 with four aromatic aldehydes, letters $L_{1-4}$. For this example they are selected as benzaldehyde, $L_1$; m-tolualdehyde, $L_2$; m-anisaldehyde, $L_3$; and 3-nitrobenzaldehyde, $L_4$, by a split solution procedure. This provides the aldehydes as benzyl derivatives after reduction of the iminium intermediates with $NaCNHB_3$ (via reductive alkylation). Each letter is reacted separately with 106. After purification, if needed, an equal molar amount of each pure "benzylated" 106 is mixed together to provide a mixture of four compounds, 114a–d, with position 2 combinatorialized with four letters to give compounds 115.

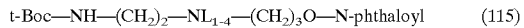

t-Boc—NH—(CH$_2$)$_2$—NL$_{1-4}$—(CH$_2$)$_3$O—N-phthaloyl    (115)

Second Set of Reactions

Position 3 is deprotected (dephthaloylation with methylhydrazine), followed by reductive alkylation (Schiff's base formation and reduction of imino intermediate with NaCNBH$_3$) with a selected extender. In this case, the selected extender is N-(3-hydroxypropionaldehyde) phthalimide, 105.

OHC(CH$_2$)$_2$O-NPhth    (105)

A variety of other extenders can be employed including aldehydes, ketones, halides, acid halides and the like.

The reaction with the extender provides a reactive secondary nitrogen ready for combinatorialization.

t-Boc—NH—(CH$_2$)$_2$—NL$_{1-4}$—(CH$_2$)$_3$O—NH—(CH$_2$)$_3$—NPh(thl7)

The sequential set of reaction are repeated again. This is continued until the desired length is obtained, i.e. the number of combinatorial sites, the length of molecule, the molecular weight, etc.). In the present example, compound 117 (having four sites for combinatorialization) is extended one additional time to provide five site for combinatorialization. Then position 1 is liberated with acid conditions. The resulting primary amine is treated separately with each of the four aromatic aldehydes. In this case, reduction of the intermediate imino (—CH=N—) moiety is not performed until the final step to allow a cleaner reactions when position 5 is subsequently fixed with each specific letter. These set of reactions provide polyamine/oxyamine compounds 121.

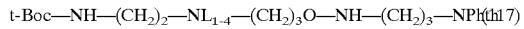

L$_{1-4}$CH=N—(CH$_2$)$_2$—NL$_{1-4}$—(CH$_2$)$_3$O—NL$_{1-4}$—(CH$_2$)$_3$O—
    NL$_{1-4}$—(CH$_2$)$_3$O-NPhth    (121)

The final set of reactions for the preparation of this particular library provides a fixed letter at position 5. In this case position 5 is not combinatorialized—it is not a mixture of the four letters. Each set of the library has a known letter at position 5. The final reduction with NaCNBH$_3$ converts both positions 1 and 5 into benzyl moieties. Thus four subsets of libraries, compounds 122a–d, (mixtures of compounds) are obtained.

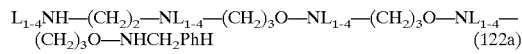

L$_{1-4}$NH—(CH$_2$)$_2$—NL$_{1-4}$—(CH$_2$)$_3$O—NL$_{1-4}$—(CH$_2$)$_3$O—NL$_{1-4}$—
    (CH$_2$)$_3$O—NHCH$_2$PhH    (122a)

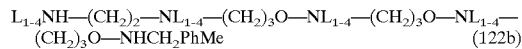

L$_{1-4}$NH—(CH$_2$)$_2$—NL$_{1-4}$—(CH$_2$)$_3$O—NL$_{1-4}$—(CH$_2$)$_3$O—NL$_{1-4}$—
    (CH$_2$)$_3$O—NHCH$_2$PhMe    (122b)

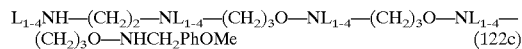

L$_{1-4}$NH—(CH$_2$)$_2$—NL$_{1-4}$—(CH$_2$)$_3$O—NL$_{1-4}$—(CH$_2$)$_3$O—NL$_{1-4}$—
    (CH$_2$)$_3$O—NHCH$_2$PhOMe    (122c)

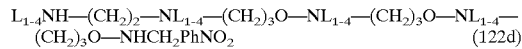

L$_{1-4}$NH—(CH$_2$)$_2$—NL$_{1-4}$—(CH$_2$)$_3$O—NL$_{1-4}$—(CH$_2$)$_3$O—NL$_{1-4}$—
    (CH$_2$)$_3$O—NHCH$_2$PhNO$_2$    (122d)

This approach employed a split solution process utilizing SURF deconvolution (iterative screening). Purification by simple flash silica gel column chromatography is performed at any stage as needed.

EXAMPLE 9

Synthesis of Intermediates for Solution and Solid Phase Combinatorial Synthesis tert-Butyl N-(2-bromoethyl) Carbamate (101)

Triethyl amine (11 mL, 77 mmole) and di-tert-butyl dicarbamate (15.2 mL, 66.5 mmole) were added to 2-bromoethyl-amine hydrobromide (14.3 g, 70 mmole) in CH$_3$CN (250 mL). The reaction mixture was stirred at room temperature for 12 hours under an argon atmosphere. 200 mL of saturated NaHCO$_3$ (aq) was added and the stirring was continued for 15 minutes. The mixture was extracted several times with ether, the combined ether layers were dried over Na$_2$SO$_4$, the Na$_2$SO$_4$ was filtered and the filtrate was evaporated to give 15.28 g (97.4%) of the title compound: TLC (Rf: 0.7; 10% MeOH/CH$_2$Cl$_2$), $^1$H NMR (CDCl$_3$) δ 1.5 (s, 9 H, tert-butyl CH3), 3.5 (m, 4 H, CH2), 5.1 (s, 1H, NH). $^{13}$C NMR (CDCl$_3$): δ 28.3 (CH3), 32.7 (CH2), 42.3 (CH2), 79.7 (C(CH3)3), 155.5 (CO).

tert-Butyl N-(2-azidoethyl) Carbamate (102)

Sodium azide (5.0 g, 75 mmole) was added to compound 101 (15.28 g, 68.2 mmole) in DMF (200 mL). The reaction mixture was stirred at about 80° C. for 12 hours under an argon atmosphere. The reaction mixture was cooled and diluted with 400 mL of ether. The ether layer was washed five times with saturated NaCl and dried over Na$_2$SO$_4$. The Na$_2$SO$_4$ was filtered and the filtrate was evaporated to give 9.8 g (77.1%) of the title compound: TLC (Rf: 0.4; 20% EtOAc/Hexane), $^1$H NMR (CDCl$_3$) δ 1.4 (s, 9 H, tert-butyl CH3), 3.2 (t, 2H, CH2), 3.3 (m, 2 H, CH2), 4.9 (s, 1 H, NH). $^{13}$C NMR (CDCl$_3$): δ 28.2 (CH3), 40 (CH2), 51.1 (CH2), 79.7 (C(CH3)3), 155.7 (CO).

tert-Butyl N-(2-aminoethyl) Carbamate (103)

Triphenyl phosphine (15 g, 58 mmole) was added to compound 102 (9.8 g, 52.6 mmole) in THF (200 mL) and H$_2$O (0.8 mL). The reaction mixture was stirred at about 80° C. for 12 hours under an argon atmosphere. The reaction mixture was evaporated to obtain a white solid residue. 200 mL of 0.5 M NaH$_2$PO$_4$ was added, the mixture was stirred and extracted with EtOAc. The aqueous layer was added to 3 N NaOH and extracted with ether. The ether layer was dried over Na$_2$SO$_4$. The Na$_2$SO$_4$ was then filtered and the filtrate was evaporated to give 8.1 g (96.5%) of the title compound: TLC (Rf: 0.2; 20% MeOH/CH$_2$Cl$_2$), $^1$H NMR (CDCl$_3$) δ 1.3 (s, 2 H, NH2), 1.4 (s, 9 H, tert-butyl CH3), 2.8 (t, 2 H, CH2), 3.2 (m, 2 H, CH2), 4.8 (s, 1 H, NH). $^{13}$C NMR (CDCl$_3$): δ 28.4 (CH3), 41.9 (CH2), 43.5 (CH2), 79.2 (C(CH3)3), 156.2 (CO).

N-(3-Hydroxypropionaldehyde Dimethylacetal)phthalimide (104)

A mixture of 3-bromopropionaldehyde dimethyl acetal (Aldrich Chemical), N-hydroxyphthalimide (Aldrich Chemical), triethylamine, and DMF is heated at 60° C. for five hours and evaporated to dryness under reduced pressure. The residue is distributed between water and ethyl acetate. The organic layer is removed, dried (MgSO$_4$), and evaporated to dryness under reduced pressure. The residue is purified by flash, silica gel chromatography to provide 104.

N-(3-Hydroxypropionaldehyde)phthalimide (105)

A mixture of N-(3-hydroxypropionaldehyde dimethylacetal)phthalimide (104) in HCl/KCl buffer (pH 1, 10/30) is stirred at 20–60° C. for 5–24 hours and then evaporated to dryness under reduced pressure. The residue is purified by flash, silica gel chromatography to provide 105.

1-(tert-Butoxycarbonyl)-9-phthaloyl-1,4,9-triaza-8-oxa-nonane (t-butoxycarbonyl—NH—(CH$_2$)$_2$—NH—(CH$_2$)$_3$—O—N-phthaloyl) (106)

A mixture 103 (1.1 equivalent) and 105 (1 equivalent) in acetonitrile/toluene (1:1) containing several drops of glacial acetic acid is heated at 20–80° C. for 5–24 hours and then treated with NaCNBH$_3$ (1.1 equivalents). The reduction is allowed to proceed for 1–5 hours. The mixture is washed with aqueous NaHCO$_3$. The organic layer is separated and evaporated to dryness under reduced pressure. The residue is purified by flash, silica gel chromatography to provide 106.

1,4,9-triaza-8-oxa-nonane-9-phthaloyl (NH$_2$—(CH$_2$)$_2$—NH—(CH$_2$)$_3$—O—N-phthaloyl) (107)

A mixture of 106 and 50% aqueous trifluoactic acid/methylene chloride (1:1) is heated at 20–50° C. for 1–24 hours and treated with saturated NaHCO$_3$. The mixture is evaporated to dryness under reduced pressure and the residue purified by flash silical gel chromatography to provide 107.

1-(p-Toluenesulfonyl)-3-chloro-propanol (103a)

To 3-chloro-1-propanol (5.02 mL, 60 mmole) in CH$_3$CN (200 mL) was added, p-toluenesufonyl chloride (17 g, 90 mmole) and pyridine (7.3 mL, 90 mmole). The reaction mixture was stirred at room temperature for 12 hours under an argon atmosphere. 200 mL of saturated NaHCO$_3$ (aq) was added and the stirring was continued for 15 minutes. The mixture was extracted several times with CH$_2$Cl$_2$. The combine CH$_2$Cl$_2$ layers were dried over Na$_2$SO$_4$, the Na$_2$SO$_4$ was filtered and the filtrate was evaporated to give 12.35 g (83.8%) of the title compound: TLC (Rf: 0.5; 20% EtOAc/Hexane), $^1$H NMR (CDCl$_3$) δ 2.1 (m, 2 H, CH2), 2.5 (s, 3 H, CH3), 3.6 (t, 2 H, CH2), 4.2 (t, 2 H, CH2), 7.6 (d & d, 4 H, Ar). $^{13}$C NMR (CDCl$_3$): δ 21.4 (CH3), 31.5 (CH2), 40.2 (CH2), 66.7 (CH2), 127.8 (Ar), 129.8 (Ar), 132.5 (Ar), 144.9 (Ar).

1-(Methanesulfonyl)-3-chloro-propanol (103b)

To 3-chloro-1-propanol (5.02 mL, 60 mmole) in CH$_3$CN (200 mL) was added methanesulfonyl chloride (10.4 g, 90 mmole) and triethyl amine (13 mL, 90 mmole). The reaction mixture was stirred at room temperature for 12 hours under an argon atmosphere. 200 mL of saturated NaHCO$_3$ (aq) was added and the stirring was continued for 15 minutes. The mixture was extracted several times with ether. The combined ether layers were dried over Na$_2$SO$_4$, the Na$_2$SO$_4$ was filtered and the filtrate was evaporated to give 10 g (96.6%) of the title compound: TLC (Rf: 0.3; 20% EtOAc/Hexane), $^1$H NMR (CDCl$_3$) δ 2.2 (m, 2 H, CH2), 3.0 (s, 3 H, CH3), 3.6 (t, 2 H, CH2), 4.4 (t, 2 H, CH2). $^{13}$C NMR (CDCl$_3$): δ 31.5 (CH2), 37.0 (CH3), 40.2 (CH2), 66.3 (CH2).

tert-Butyl N$^1$-(2-aminoethyl)-N$^2$-(3-chloropropyl) carbamate (110)

To compound 103b (4.4 g, 25 mmole) in THF (40 mL) was added to the compound 103 (9.8 g, 52.6 mmole). The reaction mixture was added to sodium hydride (0.23 g, 5.7 mmole) in an ice bath. The reaction mixture, under an argon atmosphere, was allowed to warm up to room temperature and stirring continued for 12 hours. 100 mL of 0.5 M NaH$_2$PO$_4$ (aq) was added and the aqueous layer was extracted with toluene. The aqueous layer was added to 3 N NaOH and extracted with ether. The ether layer was dried over Na$_2$SO$_4$. The Na$_2$SO$_4$ was filtered and the filtrate was evaporated to give an oily residue. The residue was purified by flash chromatography over silica gel using MeOH/CH$_2$Cl$_2$ as the eluent. The pure fractions were pooled together and evaporated to dryness to give 0.45 g (49.5%) of the title compound: TLC (Rf: 0.5; 20% MeOH/CH$_2$Cl$_2$), $^1$H NMR (CDCl$_3$) δ 1.4 (s, 9 H, tert-butyl CH3), 1.9 (m, 2 H, CH2), 2.7 (q, 4 H, CH2), 3.2 (m, 2 H, CH2), 3.6 (t, 2 H, CH2), 4.9 (s, 1 H, NH). $^{13}$C NMR (CDCl3): δ 28.4 (CH3), 32.7 (CH2), 40.3 (CH2), 42.9 (CH2), 46.4 (CH2), 49.1 (CH2), 79.3 (C(CH3)3), 156.2 (CO).

tert-Butyl N$^1$-(2-aminoethyl)-N$^2$-tritylsulfenyl-N$^2$-(3-chloropropyl) carbamate, [1-(t-butoxycarbonyl)-NH—(CH$_2$)$_2$—NS(Ph)$_3$—(CH$_2$)$_3$—Cl] (111)

Pyridine (0.7 mL, 8.5 mmole) and triphenyl methanesulfenyl chloride (0.42 g, 1.36 mmole) were added to compound 110 (420 mg, 1.7 mmole) in CH$_2$Cl$_2$ (30 mL). The reaction mixture was stirred for 12 hours under an argon atmosphere. 20 mL of 0.5 M NaH$_2$PO$_4$ (aq) was added and the aqueous layer was extracted several times with CH$_2$Cl$_2$. The CH$_2$Cl$_2$ layer was dried over Na$_2$SO$_4$, the Na$_2$SO$_4$ was filtered and the filtrate was evporated to give an oily residue. The residue was purified by flash chromatography over silica gel using EtOAc/Hexane as the eluent. The pure fractions were pooled together and evaporated to dryness to give 150 mg (17.3%) of the title compound: TLC (Rf: 0.5; 20% EtOAc/Hexane), $^1$H NMR (CDCl$_3$) δ 1.4 (s, 9 H, tert-butyl CH3), 1.9 (m, 2 H, CH2), 2.9 (m, 4 H, CH2), 3.2 (m, 2 H, CH2), 3.4 (t, 2 H, CH2), 4.6 (s, 1 H, NH). $^{13}$C NMR (CDCl$_3$): δ 28.4 (CH3), 29.7 (CH2), 37.9 (CH2), 42.2 (CH2), 53.4 (CH2), 56.5 (CH2), 79.3 (C(CH3)3), 127.2 (Ar), 127.9 (Ar), 130.1 (Ar), 143.0 (Ar), 156.2 (CO).

tert-Butyl N$^1$-(2-aminoethyl)-N$^2$-(3-aminooxypropanyl) Carbamate (1,4.9-triaza-8-oxa-1-(t-Boc)-nonane] (112)

Sodium carbonate (80 mg, 7.5 mmole) and N-hydroxyphthalimide (0.12 g, 0.75 mmole) were added to compound 110 (420 mg, 1.7 mmole) in DMF (5 mL). The reaction mixture was stirred at 80° C. for 6 hours followed by stirring at room temperature for 12 hours under an argon atmosphere. The reaction mixture was filtered, 20 mL of H$_2$O was added and the aqueous layer was extracted several times with ether. The ether layer was dried over Na$_2$SO$_4$, the Na$_2$SO$_4$ was filtered and the filtrate was evporated to give the title compound: TLC (Rf: 0.4; 20% MeOH/Hexane), $^1$H NMR (CDCl$_3$) δ 0.9 (m, 1 H, NH), 1.4 (s, 9 H, tert-butyl CH3), 1.8 (s, 2 H, NH2), 2.1 (m, 2 H, CH2), 2.5 (t, 2 H, CH2), 3.1 (m, 2 H, CH2), 3.2 (t, 4 H, CH2), 4.9 (s, 1 H, NH). $^{13}$C NMR (CDCl$_3$): δ 28.4 (CH3), 29.7 (CH2), 38.4 (CH2), 55.2 (CH2), 58.8 (CH2), 75.9 (CH2), 79.3 (C(CH3)3), 156.2 (CO).

1-(tert-Butoxycarbonyl)-9-phthaloyl-4-(triphenylsulfenyl)-1,4,9-triaza-8-oxa-nonane (t-Boc—NH—(CH$_2$)$_2$—N[S(C$_6$H$_5$)$_3$]—(CH$_2$)$_3$—O-Nphthaloyl) (113)

A mixture of chloride compound 111 (100 mmol), dry dimethylformamide (DMF), N-hydroxyphthimide (110 mmol), NaI (10 mmol), and triethyl amine (110 mmol) is heated at 50° C. for 1–24 hours. The mixture is evaporated to dryness under reducted pressure and the residue is distributed between water and ethyl acetate. The organic layer is dried ($MgSO_4$) and evaporated to dryness to provide protected polyamine 113. The material is purified by flash silica gel chromatography to give 113.

EXAMPLE 10

Synthesis of First Round Library from Protected Polyamine 109

(BG=t-Boc) and Four Letters (benzaldehyde, [$L_1$]; m-tolualdehyde, [$L_2$]; m-anisaldehyde, [$L_3$]; and 3-nitrobenzaldehyde, [$L_4$].

Step A t-Boc polyamine 109 (BG=t-Boc) (42.1 g, 125 mmol) is divided into four equal parts and each is reacted separately with benzaldehyde ($L_1$) (Aldrich, catalog #B133-4), m-tolualdehyde ($L_2$) (Aldrich, catalog #T3,550-5), m-anisaldehyde ($L_3$) (Aldrich, catalog #12,965-8), or 3-nitrobenzaldehyde ($L_4$) (Aldrich, catalog #N1,084-5). The reactants are dissolved in an organic solvent selected from methylene chloride, dichloroethane, ethyl acetate, toluene, or methanol, suitable for the individual reactants. For each reaction, 1.5–3 equivalents of the aldehyde is employed with glacial acetic (1–3%) acid added as a catalyst. The reactions are allowed to proceed from 5–24 hours then treated directly with $NaCNBH_3$ (2–3 equivalents). The reduction reaction mixtures are stirred at room temperature for 1–10 hours, filtered and evaporated to dryness under reduced pressure. The residue is suspended between ethyl acetate and aqueous $NaHCO_3$. The organic layer is separated, dried ($MgSO_4$), and concentrated to dryness under reduced pressure. The individual residues may be purified by column chromatography if needed. The procedure provides a polyamine/oxyamine 115 with position 2 combinatorialized with the four selected aromatic aldehydes (reductive alkylation to provide benzyl moieties).

Steps B & C

Equal moles of each pure reaction residue (114a–b, ≈11.0 g, ≈25 mmol each) are dissolved in methanol and mixed together. The solution is treated with methylhydrazine (250 mmol), heated under reflux for one hour, and evaporated under reduce pressure. The residual mixture is triturated with chloroform and filtered. The filtrate is evaporated to dryness under reduced pressure and the residue purified by silica gel, flash column chromatography if needed to provide ≈100 mmol (≈31 g) of oxyamine 116.

Step D

Oxyamine mixture 116 (≈31 g, ≈100 mmol) dissolved in ethyl acetate containing glacial acetic acid (1–3%) is treated with N-(3-hydroxypropionaldehyde)phthalimide (105, 110 mmol). The solution is stirred at room temperature for 1–24 hours followed by treating with $NaCNBH_3$ (150 mmol) and stirring at room temperature for 1–10 hours. The reaction mixture is poured into $H_2O$ and the layers separated. The organic phase is washed with saturated $NaHCO_3$ solution, dried ($MgSO_4$), and evaporated under reduced pressure. The residual 117 is purified by flash silica gel column chromatography if needed to yield approximately 100 mmol (≈50 g) of 117.

Step E (Repeat Step A & B), Combinatorilization of Position 3 to Provide Polyamine/Oxyamine 118

The t-Boc protected polyamine 117 (50.6 g, 100 mmol) is divided into four equal parts and each is reacted separately with benzaldehyde ($L_1$), m-tolualdehyde ($L_2$), m-anisaldehyde ($L_3$), or 3-nitrobenzaldehyde ($L_4$). The reactants are dissolved in an organic solvent selected from methylene chloride, dichloroethane, ethyl acetate, toluene, or methanol, suitable for the individual reactant. For each reaction, 1.5 to 3 equivalents of the aldehyde is used with glacial acetic acid (1–5%) employeed as a catalyst. The reactions are allowed to proceed from 5–24 hours then treated directly with $NaCNBH_3$ (2–3 equivalents). The reaction mixtures are stirred at room temperature for 1–10 hours, filtered and evaporated to dryness under reduced pressure. The residue is suspended between ethyl acetate and aqueous $NaHCO_3$. The organic layers are separated, dried ($MgSO_4$), and concentrated under reduced pressure. The four individual reactions may be purified by column chromatography if needed. Equal mole equivalents of each pure reaction residue is dissolved in methanol and mixed together to provide 118 (≈60 g)

Steps F & G, (repeat of Steps C, D & E), Combinatorilization of Position 4 to Provide Polyamine/Oxyamine 120

Step F

A solution of 118 (60.7 g, 100 mmol) in methanol is treated with methylhydrazine (250 mmol), heated under reflux for one hour, and evaporated under reduce pressure. The residual mixture is triturated with chloroform and filtered. The filtrate is evaporated to dryness under reduced pressure and the residue purified by silica gel, flash column chromatography if needed to provide ≈100 mmol (≈75 g) of position 5 oxyamine, 119. The oxyamine compound is dissolved in ethyl acetate containing glacial acetic acid (1–3%) and treated with N-(3-hydroxypropionaldehyde) phthalimide (105, 110 mmol). The solution is stirred at room temperature for 1–24 hours followed by treating with $NaCNBH_3$ (150 mmol) and stirring at room temperature for 1–10 hours. The reaction mixture is mixed with water and the layers separated. The organic phase is washed with saturated $NaHCO_3$ solution, dried ($MgSO_4$), and concentrated under reduced pressure. The residual 119 is purified by flash silica gel column chromatography if needed to yield approximately 100 mmol (≈75 g) of 119.

Step G

The t-Boc polyamine 119 (≈75 g, ≈100 mmol) is divided into four equal parts and each is reacted separately with benzaldehyde ($L_1$), m-tolualdehyde ($L_2$), m-anisaldehyde ($L_3$), and 3-nitrobenzaldehyde ($L_4$) as described in Step E above. The resulting four individual reactions are purified by column chromatography as needed. Equal mole equivalents of each pure reaction residue is dissolved in methanol and mixed together to provide 120 (≈89 g).

Step H Combinatorilization of Position 1 to Provide Polyamine/Oxyamine 121

Residue 120 (90 g, 100 mmol) dissolved in a mixture of 1:1 volume of 50% aqueous trifluoroacetic acid and dichloromethane is reacted at 20–50° C. for 1–24 hours and treated with $NaHCO_3$ solution. The organic layer is separated, dried ($MgSO_4$) and evaporated to dryness under reduced pressure. The residue may be purified by chromatography as needed. The residue (≈100 mmol) is dissolved in methanol and divided into four equal parts and each evaporated under reduced pressure to dryness. Each residue is reacted separately with benzaldehyde ($L_1$), m-tolualdehyde ($L_2$), m-anisaldehyde ($L_3$), or 3-nitrobenzaldehyde ($L_4$) as described above. The reactions are not treated with $NaCNBH_3$ in order to allow isolation of the imino derivative of each aromatic aldehyde. The four individual reactions are purified by column chromatography as needed. Equal mole equivalents of each pure reaction residue is dissolved in methanol and mixed together to provide 121 (≈86 g).

Step I Combinatorilization of Position 5 to Provide Polyamine/Oxyamine 122a–d as Four Sets of First Round Libraries with Position 5 Fixed Mixture 121 (≈86 g, ≈100 mmol) in methanol is treated with methylhydrazine (150 mmol) at 20–50° C. for 1–24 hours and then evaporated under reduce pressure. The residual mixture is triturated with chloroform and filtered. The filtrate is evaporated to dryness under reduced pressure and the residue purified by silica gel flash column chromatography as needed to provide ≈100 mmol of position 5 oxyamine 121. The oxyamine 121 is dissolved in ethyl acetate and separated into four equal parts. Each solution is reacted separately with benzaldehyde ($L_1$), m-tolualdehyde ($L_2$), m-anisaldehyde ($L_3$), or 3-nitrobenzaldehyde ($L_4$) as described above. The reactions are allowed to proceed from 5–24 hours, then treated directly with $NaCNBH_3$ (2–3 equivalents). The reaction mixtures are stirred at room temperature for 1–10 hours, filtered and evaporated to dryness under reduced pressure. The residues are suspended between ethyl acetate and aqueous $NaHCO_3$. The organic layers are separated, dried ($MgSO_4$), and concentrated to dryness under reduced pressure. The four individual reactions are purified by column chromatography as needed to give a library of four sets of polyamine/oxyamines combinatorialized at positions 1–4 with four benzyl moieties and fixed at position 5 with a single, known benzyl moiety.

EXAMPLE 11

Formation of Activated Derivative for Attachment to CPG Solid Phase Support

I. General Procedure Amino Compounds

I-a Ethyl Linker—O-Succinyl Ethyl N-phthalimide

Succinic anhydride (1.5 g, 15 mmole) and DMAP (1.84 g, 15 mmole) were added to 2-hydroxyl-ethyl N-phthalimide (1.9 g, 10 mmole) dissolved in 40 mL of $CH_2Cl_2$ (40 mL). The reaction mixture was stirred at room temperature for 12 hours under an argon atmosphere. $NaH_2PO_4$ (10% aq, 100 mL) was added and the stirring was continued for 15 minutes. The aqueous layer was extracted several times with $CH_2Cl_2$. The combined $CH_2Cl_2$ was dried over $Na_2SO_4$ and the filtrate concentrated to give a yellow residue. The residue was purified by flash chromatography over silica gel using Hexane/EtOAc as the eluent. The pure fractions were pooled together and evaporated to dryness to give 2.31 g (79.3%) of the title compound: TLC (Rf: 0.5; 80% EtOAc/Hexane), $^1$H NMR (DMSO-d6) δ 2.4 (s, 4 H, succinyl CH2), 3.8 (t, 2 H, CH2), 4.2 (t, 2 H, CH2), 7.8 (d, 4 H, Ar), 12.2 (s, 1 H, COOH).

II. General Procedure Hydroxylamino Compounds

II-a Ethyl Linker—O-Succinyl Ethyl Hydroxy N-phthalimide

Diethylazodicarbonate (3.15 mL, 20 mmole) in THF (8 mL) was added to a THF solution of N-hydroxy phthalimide (3.26 g, 20 mmole), ethylene glycol (1.2 mL, 20 mmole) and triphenyl phosphine (5.25 g, 20 mmole). The reaction mixture was stirred at room temperature for 12 hours under an argon atmosphere. The reaction mixture was evaporated to dryness and triturated with ethyl ether. The mixture was filtered to remove a white ppt and the filtrate was concentrated to a residue. The residue was used for the next step without further purification. TLC (Rf: 0.7; 5% MeOH/$CH_2Cl_2$), $^1$H NMR (DMSO-d6) δ 3.7 (q, 2 H, CH2), 4.2 (t, 2 H, CH2), 7.9 (s, 4 H, Ar). $^{13}$C NMR (DMSO-d6): δ 59.2 (CH2), 79.2 (CH2), 123.4 (Ar), 128.7 (Ar), 134.9 (Ar), 163.7 (CO). The residue was dissolved in $CH_2Cl_2$ (140 mL) and succinic anhydride (2.6 g, 26 mmole) and DMAP (3.2 g, 26.3 mmole) were added. The resulting reaction mixture was stirred at room temperature for 12 hours under an argon atmosphere. $NaH_2PO_4$ (10% aq, 100 mL) was added and the stirring was continued for 15 minutes. The aqueous layer was extracted several times with $CH_2Cl_2$. The combine $CH_2Cl_2$ layers were dried $Na_2SO_4$ and concentrated to give a yellow residue. The residue was purified by flash chromatography over silica gel using MeOH/$CH_2Cl_2$ as the eluent. The pure fractions were pooled together and evaporated to dryness to give 1.3 g (21.7%) of the title compound: TLC (Rf: 0.4; 5% MeOH/$CH_2Cl_2$), $^1$H NMR (DMSO-d6) δ 2.5 (s, 4 H, succinyl CH2), 4.3 (q, 4 H, CH2), 7.9 (s, 4 H, Ar), 12.2 (s, 1 H, COOH).

II-b Propyl Linker—O-Succinyl Propyl Hydroxy N-phthalimide

A 1-hydroxyl N-phthalimido-3-propanol intermediate was prepared by treating N-hydroxy phthalimide (2.4 g, 15 mmole) in DMSO (20 mL) with 3-chloro-1-propanol (0.94 g, 10 mmole) and $Na_2CO_3$ (1.6 g, 15 mmole). The reaction mixture was stirred at 80° C. for 1 hours under an argon atmosphere. $H_2O$ (50 mL) and EtOAc (100 mL) were added and the stirring was continued for 15 minutes. The aqueous layer was extracted several times with EtOAc. The combine EtOAc layers were dried over $Na_2SO_4$ and concentrated to give 2.81 g of the title compound: TLC (Rf: 0.7; 5% MeOH/$CH_2Cl_2$), $^1$H NMR (DMSO-d6) δ 1.8 (m, 2 H, CH2), 3.5 (m, 2 H, CH2), 4.2 (t, 2 H, CH2), 4.5 (t, 1 H, OH), 7.8 (s, 4 H, Ar). $^{13}$C NMR (DMSO-d6): δ 31.3 (CH2), 57.3 (CH2), 75.5 (CH2), 123.5 (Ar), 128.7 (Ar), 135.1 (Ar), 163.7 (CO).

The propyl intermediate is treated as described above for the ethyl compound to give the O-succinyl activated compound for loading on CPG.

III. 1-(O-Succinyl)-1,4,9-triaza-8-oxa-decane-9-phthaloyl (Succinyl—$NH_2$—($CH_2)_2$—NH—($CH_2)_3$—O—N-phthaloyl) (108a)

A mixture of amine 107 (10 mmol), succinyl anhydride (15 mmol) and DMAP (15 mmol) is dissolved in $CH_2Cl_2$ (100 mL). The reaction mixture is stirred at room temperature for 12 hours under argon atmosphere. $NaH_2PO_4$ (10% aq, 100 mL) is added and stirring is continued for 15 minutes. The aqueous layer is extracted several times with $CH_2Cl_2$. The combined $CH_2Cl_2$ layers are dried over $Na_2SO_4$ and concentrated to get a yellow residue. The residue is purified by flash chromatography over silica gel using Hexane/EtOAc as the eluent. The pure fractions are pooled together and concentrated to give the title compound (108a).

EXAMPLE 12

Loading of Succinyl Intermediates on Control Pore Glass (CPG)

I. Formation of CPG-O-succinyl Ethyl N-phthalimide

CPG (5 g), DMAP (0.1 g, 0.75 mmole) and DCC (1.6 g, 7.5 mmole) were added to a solution of O-succinyl ethyl N-phthalimide (from example 11 above) (0.44 g, 1.5 mmole) in $CH_2Cl_2$ (20 mL). The mixture was shaken for 12 hours. The resin was collected by filtration on a sintered glass funnel and washed with $CH_2Cl_2$, MeOH and ethyl ether. The resin was dried and the loading was measured by taking a small sample for a ninhydrin test. The loading test sample was carefully weighed and treated with 5% of methyl hydrazine in MeOH for 3 hours at room temperature. A quantitative ninhydrin test was carried out by using the standard extinction coefficient (ε). The loading of the compound on CPG was determined to be 50 μmole/g. The resin was capped with acetic anhydride for use in the first coupling reaction.

II. Formation of CPG-1-(O-Succinyl)-1,4,9-triaza-8-oxa-decane-9-phthaloyl (CPG-NH$_2$—(CH$_2$)$_2$—NH—(CH$_2$)$_3$—O—N-phthaloyl) (108a)

CPG (5 g), DMAP (0.1 g, 0.75 mmole) and DCC (1.6 g, 7.5 mmole) were added to a solution of compound 108a (0.44 g, 1.5 mmole) in CH$_2$Cl$_2$ (20 mL). The mixture was shaken for 12 hours. The resin was collected by filtration on a sintered glass funnel and washed with CH$_2$Cl$_2$, MeOH and ethyl ether. The resin was dried and the loading measured by taking a small sample for the ninhydrin test. The loading test sample was carefully weighed and treated with 5% of methyl hydrazine in MeOH for 3 hours at room temperature. A quantitative ninhydrin test was carried out by using the standard extinction coefficient ($\epsilon$). The loading of the compound on CPG determined to be 50 $\mu$mole/g. The resin was capped with acetic anhydride for use in the first coupling reaction.

EXAMPLE 13

Loading of Intermediate on p-alkoxybenzyl Alcohol Resin

I. Preparation of Resin p-Alkoxy benzyl alcohol resin (3.5 g, 2.45 mmole) was added to a mixture of 4-nitrophenyl chloroformate (6.4 g, 30.8 mmole) and TEA (4.8 mL, 33.9 mmole) CH$_2$Cl$_2$ (15 mL). The mixture was shaken for 12 hours. The resin was collected by filtration on sintered glass funnel and washed with CH$_2$Cl$_2$.

II. Submonomer Amine

II-a: Phthalimidoacetaldehyde

Phthalimidoacetaldehyde diethylacetate (5.3 g, 20 mmole) was dissolved in chloroform (100 mL) and a trifluoroacetic acid solution (50% aqueous, 80 mL) was added. The reaction mixture was stirred at room temperature for 12 hours. The chloroform layer was collected and dried over sodium sulfate. The filtrate was concentrated to give 3.75 g of the title compound (99% yield): TLC (Rf: 0.4; 40% EtOAc/Hexane), $^1$H NMR (DMSO-d6) $\delta$ 4.6 (s, 2 H, CH2), 7.8 (m, 4 H, Ar), 9.6 (s, 1 H, CHO). $^{13}$C NMR (DMSO-d6): $\delta$ 47.4 (CH2), 123.4 (Ar), 131.5 (Ar), 134.8 (Ar), 167.3 (CO), 196.8 (CHO).

II-b: Coupling Reaction of Phthalimidoacetaldehyde and Resin via Reductive Amination To the phthalimidoacetaldehyde from step II-a (0.12 g, 38.5 $\mu$mole), resin (0.076 g, 0.4 mmole), 5 N HCl (12 p, 60 $\mu$mole) and sodium cyanoborohydride (0.001 g, 15.9 $\mu$mole) were added. The mixture was shaken for 12 hours and a small sample was taken for the standard ninhydrin test. The coupling yield was 46.6%. The coupling step was repeated and the loading was redetermined by the standard ninhydrin test. The final overall coupling yield was 75.9%. The resin was capped with acetic anhydride for use in submonomer coupling reactions.

II-c: Attachment of Submonomer

Attachment of ethylene diamine to above derivatized p-alkoxybenzyl alcohol resin was effected by adding ethylene diamine (2.5 mL, 37.4 mmole), TEA (6.3 mL, 45 mmole) and acetonitrile (15 mL) to the resin. The mixture was shaken for 12 hours. The resin was collected by filtration on a sintered glass funnel and washed with CH$_2$Cl$_2$ and DMF. The resin was dried and the loading was measured by taking a small sample for a ninhydrin test. Quantitative ninhydrin test was carried out by using the standard extinction coefficient ($\epsilon$). The loading of ethylene diamine on p-alkoxy benzyl alcohol resin was 440 $\mu$mole/g (63% coupling yield). The resin was ready to be used for the first coupling reaction.

III. Polyamine

Polyamine 107 (37.4 mmole), TEA (6.3 mL, 45 mmole) and 15 mL of acetonitrile (15 mL) were added to the resin of step II-c. The mixture was shaken for 12 hours. The resin was collected by filtaration on a sintered glass funnel and washed with CH$_2$Cl$_2$ and DMF. The resin was dried and the loading was measured by taking a small sample for a ninhydrin test. The quantitative ninhydrin test was carried out by using the standard extinction coefficient ($\epsilon$). The loading of polyamine 107 on p-alkoxy benzyl alcohol resin was 440 $\mu$mole/g (63% coupling yield). The resin was ready to be used for the first coupling reaction.

EXAMPLE 14

Preparation of Library Subsets 114a–d via Alkylation Using Benzyl Halides

Library subsets 114a–d are prepared as per the general teachings of Example 10 except that these subsets are synthesized via an alkylation reaction in place of the Schiff's base reduction. Aralkyl halides, corresponding to the aldehydes of employed Example 10, are use for these alkylation reactions. In this approach, direct alkylation provides the combinatorialized positions directly. Reduction procedures are eliminated. The halides used for introduction of the letters are benzyl halides [benzyl bromide (L$_1$) (Aldrich catalog #B1,790-5), 3-methylbenzyl bromide (L$_2$) (Aldrich catalog #B8,350-9), 3-methoxybenzyl chloride (L$_3$) (Aldrich catalog #20,938-4, and 3-nitro-benzyl bromide (L$_4$) (Aldrich catalog #22,251-80)].

Step A t-Boc polyamine 109 (42.1 g, 125 mmol) is divided into four equal parts and each is reacted separately with benzyl bromide (L$_1$), 3-methylbenzyl bromide (L$_2$), 3-methoxybenzyl bromide (L$_3$), or 3-nitrobenzyl bromide (L$_4$). The reactants can be dissolved in an organic solvent selected from methylene chloride, dichloroethane, ethyl acetate, toluene, or methanol suitable for the individual reactant. For each reaction 1.5–10 equivalents of the benzyl bromide is employed. A equivalent amount of base is utilized to neutralize the liberated acid generated by alkylation. Bases such as triethyl amine, DBU, pyridines, DMAP, carbonates, bicarbonates, and sodium hydride may be effectively employed in these alkylation reactions. Reactions are allowed to proceed from 1–24 hours and then evaporated to dryness under reduced pressure. The residues are suspended between ethyl acetate and water. The organic layers are separated, dried (MgSO$_4$), and reduced to dryness under reduced pressure. The individual residues may be purified by column chromatography as needed. This procedure provides a polyamine/oxyamine 115 with position 2 combinatorialized with the four selected aromatic benzyl bromides and corresponds to the compounds 115 prepared by reductive alkylation of Example 10.

Step B & C

Equal moles of each pure reaction residue (114a–b, $\approx$11.0 g, $\approx$25 mmol each) is dissolved in methanol and mixed together. The solution is treated with methylhydrazine (250 mmol), heated under reflux for one hour, and evaporated under reduce pressure. The residual mixture is triturated with chloroform and filtered. The filtrate is evaporated to dryness under reduced pressure and the residue purified by silica gel, flash column chromatography if needed. This will provide $\approx$100 mmol ($\approx$31 g) of oxyamine 116.

Step D

Mixture 116 ($\approx$31 g, $\approx$100 mmol) is dissolved in ethyl acetate containing 1–3% glacial acetic acid and treated with N-(3-hydroxypropionaldehyde)phthalimide (105, 110 mmol). The solution is stirred at room temperature for 1 to 24 hours before treating with NaCNBH$_3$ (150 mmol) and stirring at room temperature for 1 to 10 hours. The mixture is mixed with water and separated. The organic phase is washed with saturated NaHCO$_3$ solution, dried (MgSO$_4$), and evaporated under reduced pressure. The residual 117 is purified by flash silica gel column chromatography as needed. Approximately 100 mmol (≈50 g) of 17 is obtained.

Step E—(repeat Step A & B), Combinatorilization of Position 3, Provides Polyamine/Oxyamine 118 t-Boc polyamine 117 (50.6 g, 100 mmol) is divided into four equal parts and each is reacted separately with benzyl bromide (L$_1$), 3-methylbenzyl bromide (L$_2$), 3-methoxybenzyl bromide (L$_3$), or 3-nitrobenzyl bromide (L$_4$) as described above. Reactions are evaporated to dryness under reduced pressure. The residues are suspended between ethyl acetate and water. The organic layers are separated, dried (MgSO$_4$), and reduced to dryness under reduced pressure. The individual residues may be purified by column chromatography as needed. Equal amounts of each residue are mixed to provide polyamine/oxyamine 118 with position 2 combinatorialized with the four selected aromatic benzyl bromides (and corresponds to 118 prepared by reductive alkylation) to provide the benzyl moieties.

Combinatorialization is continued as described in Example 10 except alkylation reactions with benzyl bromides are used in place of Schiff's base reductive alkylations. The alkylation procedures provide libraries comparable to the libraries synthesized by reductive couplings.

EXAMPLE 15

Preparation of Library Subsets 114a–d Using Benzoic Acids and Benzoic Acid Halides Library subsets 114a–d are prepared by utilizing substituted benzoic acid halides to acylate the primary amine and secondary and primary oxyamines followed by reduction of the resultant amide bond to afford a benzyl moiety combinatorialized at each selected site in the polyamine/oxyamine. Benzoyl acid chloride (L$_1$), 3-methylbenzoyl chloride (L$_2$), 3-methoxybenzoyl chloride (L$_3$), and 3-nitrobenzoyl chloride (L$_4$)] corresponding to the benzyl bromides and benzaldehydes employed in the synthesis of Examples 10 and 14 are employed.

Library subsets 114a–d are prepared as per the general teachings of Example 10 except that these subsets are synthesized via an acylation reaction in place of the Schiff's base reduction. Aryl acid halides are used for these alkylation reactions corresponding to benzyl aldehydes employed in the synthesis of Example 10. In this approach, direct acylation provides the combinatorialized positions directly. As in Example 14, reduction procedures are eliminated. The acid halides used for introduction of the letters are benzoyl chloride (L$_1$), 3-methylbenzoyl chloride (L$_2$), 3-methoxybenzoyl chloride (L$_3$), and 3-nitrobenzoyl chloride (L$_4$).

Step A t-Boc polyamine 109 (42.1 g, 125 mmol) is divided into four equal parts and each is reacted separately with benzoyl chloride (L$_1$), 3-methylbenzoyl chloride (L$_2$), 3-methoxybenzoyl chloride (L$_3$), and 3-nitrobenzoyl chloride (L$_4$). The reactants are dissolved in an organic solvent selected from methylene chloride, dichloroethane, ethyl acetate, toluene, or methanol appropriate for the individual reactant. For each reaction, 1.5–10 equivalents of an acid halide is employed. A equivalent amount of base is utilized to neutralize the liberated acid generated by acylation. Bases such as triethyl amine, DBU, DMAP, pyridines, carbonates, bicarbonates, and sodium hydride may be effectively employed in these alkylation reactions. The reactions are allowed to proceed from 1 to 24 hours and then evaporated to dryness under reduced pressure. The residues are suspended between ethyl acetate and water. The organic layers are separated, dried (MgSO$_4$), and concentrated to dryness under reduced pressure. The individual residues are reduced with NaCNBH$_3$ or other reagents known to effective convert amide bonds to the corresponding methylenes. The individual residues may be purified by column chromatography as needed. This procedure provides a polyamine/oxyamine 115 with position 2 combinatorialized with the four selected aromatic acid chlorides and corresponds to 115 prepared by reductive alkylation of Example 10 to provide benzenzyl moieties.

Step B & C

Equal moles of each pure reaction residue (114a–b, ≈11.0 g, ≈25 mmol each) is dissolved in methanol and mixed together. The solution is treated with methylhydrazine (250 mmol), heated under reflux for one hour, and concentrated under reduce pressure. The residual mixture is triturated with chloroform and filtered. The filtrate is concentrated and the residue purified by silica gel, flash column chromatography as needed. This provides ≈100 mmol (≈31 g) of oxyamine 116.

Step D

Mixture 116 (≈31 g, ≈100 mmol) is dissolved in ethyl acetate containing glacial acetic acid (1–3%) and treated with N-(3-hydroxypropionaldehyde)phthalimide (105, 110 mmol). The solution is stirred at room temperature for 1–24 hours before treating with NaCNBH$_3$ (150 mmol) and stirring at room temperature for 1–10 hours. The mixture is mixed with water and separated. The organic phase is washed with saturated NaHCO$_3$ solution, dried (MgSO$_4$), and concentrated under reduced pressure. The residual 117 is purified by flash silica gel column chromatography if needed. Approximately 100 mmol (≈50 g) of 117 is obtained.

Step E (repeat Step A & B), Combinatorilization of Position 3, to Provides Polyamine/Oxyamine 118 t-Boc polyamine 117 (50.6 g, 100 mmol) is divided into four equal parts and each is reacted separately with benzoyl chloride (L$_1$), 3-methylbenzoyl chloride (L$_2$), 3-methoxybenzoyl chloride (L$_3$), and 3-nitrobenzoyl chloride (L$_4$) as described above. Reactions are evaporated to dryness under reduced pressure. The residues are suspended between ethyl acetate and water. The organic layers are separated, dried (MgSO$_4$), and reduced to dryness under reduced pressure. The individual residues are purified by column chromatography as needed. Equal amounts of each residue are mixed to provide polyamine/oxyamine 118 with position 2 combinatorialized with the four selected aromatic acid chlorides and corresponds to 118 prepared by either reductive alkylation or alkylation as described in Examples 10 and 14.

Combinatorialization is continued as described in Example 10 except acylation reactions with acyl acid chlorides are used in place of Schiff's base reductive alkylations. Acylation procedures provide libraries comparable to libraries synthesized by reductive or alkylations. The benzoyl halides used to introduce the letters are readily available from various commercial chemical suppliers.

EXAMPLE 16

Backbone Extenders Alternate Methods of Preparation 1-(tert-Butoxycarbonyl)-9-phthaloyl-1,4,9-triaza-8-oxa-nonane (t-butoxycarbonyl-NH—$(CH_2)_2$—NH—$(CH_2)_3$—O—N-phthaloyl) (106)

I. Via Alkylation

Step 1—Preparation of N-[(3-bromopropyl)oxy]phthalimide (Br$(CH_2)_3$—O—N-phthalimide))

A mixture of N-hydroxyphthalimide (100 mmol) and 1,3-dibromopropane (100 mmol) in dry DMF and triethyl amine (110 mmol) is stirred at 20–75° C. for 1–10 hours. After filtration, the mixture is evaporated to dryness under reduced pressure. The residue is purified by silica gel chromatography to give N-[(3-bromopropyl)oxy]phthalimide.

Step 2

A mixture of tert-butyl-N-(2-aminoethyl) carbamate (103) (100 mmol) and N-[(3-bromopropyl)oxy]phthalimide (100 mmol) in dry DMF and triethylamine (110 mmol) is stirred at 20 to 75° C. for 1 to 25 hours. After filtration, the mixture is evaporated to dryness under reduced pressure. The residue is distributed between water and ethyl acetate. The organic layer is dried ($MgSO_4$) and evaporated to dryness to yield polyamine 106. Purification of 106 is achieved by silica gel chromatography.

II. Extension by Acylation

Step 1—Preparation of N-[(3-propionyl chloride)oxy]-phthalimide (ClCO$(CH_2)_3$—O—N-phthalimide).

A mixture of N-hydroxyphthalimide (100 mmol) and 3-bromopropinoic acid (100 mmol) in dry DMF and triethyl amine (210 mmol) is stirred at 20 to 75° C. for 1 to 10 hours. After filtration, the mixture is evaporated to dryness under reduced pressure and distributed between water and ethyl acetate. The water layer is treated with dilute HCl and extracted with ethyl acetate. The organic layer is treated with thionyl chloride (112 mmol), refluxed for 1 hour, and evaporated to dryness under reduced pressure to give N-[(3-propionyl chloride)oxy]-phthalimide.

Step 2

A mixture of tert-butyl-N-(2-aminoethyl) carbamate (103) (100 mmol) and N-[(3-propionyl chloride)oxy]phthalimide (100 mmol) in dry DMF and triethyl amine (110 mmol) is stirred at 20 to 75° C. for 1 to 25 hours. After filtration, the mixture is evaporated to dryness under reduced pressure. The residue is distributed between water and ethyl acetate. The organic layer is dried ($MgSO_4$) and evaporated to dryness. The residue is dissolved in methanol and treated with $NaCNBH_3$. The mixture is stirred at room temperature for 1 to 5 hours. The mixture is filtered and the filtrate is evaporated to dryness under reduced pressure to yield polyamine 106. Purification of 106 is achieved by silica gel chromatography.

EXAMPLE 17

Backbone Extenders—Amino Acid Type

Conversion of amino acids into N-(acetaldehydo)-phthalimide (OHCCHRN-phthalimide where R is an amino acid side chain) is effected by protection of the amino acids with the phthalimido group by treatment with phthalic anhydride and subsequently reduced to provide aldehydo amino acid type extenders.

EXAMPLE 18

Backbone Extenders—Oxyamino Acid Type

Oxyamino acid type extenders are prepared by conversion of alkane acids and R-substituted alkane acids into N-[(alkyl-R-aldehydo)oxy]phthalimide, i.e. OHC-alkyl-R—O—N-phthalimide. Substituted acids are bromonated in the alpha position and subsequently reacted with N-hydroxyphthalimide to provide N—($HO_2$C-alkyl-R)O-phthalimide. Reduction of the acid to an aldehyde function provides N—(aldehydoalkyl-substituted)—O—N-phthalimide type extenders.

EVALUATION

PROCEDURE 1—Nuclease Resistance

A. Evaluation of the Resistance of Oligomeric Compounds to Serum and Cytoplasmic Nucleases.

Compounds of the invention can be assessed for their resistance to serum nucleases by incubation of the compounds in media containing various concentrations of fetal calf serum or adult human serum. Labelled compounds are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligomeric compounds it is possible to determine the effect on nuclease degradation by the particular modification. For the cytoplasmic nucleases, an HL 60 cell line can be used. A post-mitochondrial supernatant is prepared by differential centrifugation and the labelled compounds are incubated in this supernatant for various times. Following the incubation, compounds are assessed for degradation as outlined above for serum nucleolytic degradation. Autoradiography results are quantitated and are indictive of resistances of the compounds to serum and cytoplasmic nucleases.

B. Evaluation of the Resistance of Oligomeric Compounds to Specific endo- and exo-nucleases.

Evaluation of the resistance of the compounds of the invention to specific nucleases (i.e., endonucleases, 3',5'-exo-, and 5',3'-exonucleases) can be done to determine the exact effect of the linkages on degradation. The compounds are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the compound's linkage are determined for specific nucleases and compared with the results obtained from the serum and cytoplasmic systems. As with the serum and cytoplasmic nucleases, it is expected that the compounds of the invention will be completely resistant to endo- and exo-nucleases.

PROCEDURE 2

Use of Combinatorial Library for $PLA_2$ Inhibitors

A preferred target molecule for utilizing such combinatorial techniques is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (see, Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (see, e.g., Dennis, ibid.; Glaser, et al., *TiPs Reviews* 1992, 14, 92; and Pruzanski, et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, et al., *Inflammation* 1988, 12, 549) or into the articular space of rabbits (Bomalaski, et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g., pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott, et al., *Science* 1990, 250, 1541). Recently, the crystal structure of $PLA_2$ from human synovial fluid has been solved (Wery, et al., *Nature* 1991, 352, 79). The structures clarify the role of calcium and amino acid residues in catalysis. The calcium acts as a Lewis acid to activate the scissile ester carbonyl of 1,2-diacylglycerophospholipids and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site. (see, e.g., Achari, et al., *Cold Spring Harbor Symp. Quant. Biol.* 1987, 52, 441; Cho, et al., *J. Biol. Chem.* 1988, 263, 11237; Yang, et al., *Biochem. J.* 1989, 262, 855; and Noel, et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger, et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e., phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (see, e.g., Yuan, et al., *J. Am. Chem. Soc.* 1987, 109, 8071; Lombardo, et al., *J. Biol. Chem.* 1985, 260, 7234; Washburn, et al., *J. Biol. Chem.* 1991, 266, 5042; Campbell, et al., *J. Chem. Soc., Chem. Commun.* 1988, 1560; and Davidson, et al., *Biochem. Biophys. Res. Commun.* 1986, 137, 587), reports describing in vivo activity are limited (see, e.g., Miyake, et al., *J. Pharmacol. Exp. Ther.* 1992, 263, 1302).

In one preferred embodiment, functional groups appended to the repeating units of the invention are selected for their potential to interact with, and preferably inhibit, the enzyme $PLA_2$. Thus, the compounds of the invention can be used for topical and/or systematic treatment of inflammatory diseases including atopic dermatitis and inflammatory bowel disease. In selecting the functional groups, advantage can be taken of $PLA_2$'s preference for anionic vesicles over zwitter-ionic vesicles.

Certain compounds of the invention include aromatic functional groups to facilitate binding td the cleft of the $PLA_2$ enzyme. (see, Oinuma, et al., *J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The $PLA_2$ assay can be effected using a combinatorial screening strategy such as the SURF strategy. For this assay, the oligomer libraries are screened for inhibition of human type II $PLA_2$ enzymatic activity. Typically, these libraries contain hundreds or thousands of different compounds. Successive iterations of the SURF technique is effected to select unique oligomers from the library. The libraries additionally can be screened in other in vitro assays to determine further mechanisms of inhibition.

To maximize the identification of a tight binding oligomeric inhibitor of $PLA_2$ via a combinatorial approach, an array of functional groups typically are included in a randomized library. The oligomers are assembled as described above.

STEP 1 $PLA_2$ Assay

The oligomer libraries are screened for inhibition of $PLA_2$ in an assay using *E. coli* labeled with $^3$H-oleic acid (see, Franson, et al., *J. Lipid Res.* 1974, 15, 380; and Davidson, et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each the oligomeric pools is done in water: 10 μl of each oligomer is incubated for 5 minutes at room temperature with a mixture of 10 μl $PLA_2$, 20 μl 5×$PLA_2$ Buffer (500 mM Tris 7.0–7.5, 5 mM $CaCl_2$), and 50 μl water. Each of the oligomer samples is run in duplicate. At this point, 10 μl of $^3$H *E. coli* cells is added. This mixture is incubated at 37° C. for 15 minutes. The enzymatic reaction is stopped with the addition of 50 μl 2M HCL and 50 μl fatty-acid-free BSA (20 mg/ml PBS), vortexed for 5 seconds, and centrifuged at high speed for 5 minutes. 165 μl of each supernate is then put into a scintillation vial containing 6 ml of scintillant (ScintiVerse) and cpms are measured in a Beckman Liquid Scintillation Counter. As a control, a reaction without oligomer is run alongside the other reactions as well as a baseline reaction containing no oligo as well as no $PLA_2$ enzyme. CPMs are corrected for by subtracting the baseline from each reaction data point.

STEP 2 Verification of Assay

The $PLA_2$ test system was verified using phosphorothioate oligonucleotides with one or more strings of guanosine nucleotides (at least 3 per string). Libraries of these oligonucleotides were deconvoluted using the SURFs screening strategy and were shown to have an inhibitory effect on the $PLA_2$ enzyme. Knowing that phosphorothioate oligonucleotides inhibit $PLA_2$ with some sequence specificity, an eight nucleotide phosphorothioate library consisting of the four natural bases was used to test the assay system for suitability as a SURF screen. This library had been synthesized for use in another system and all subsets were not still available (indicated by dashes in Table III, below). Using the SURF method, it was confirmed that a stretch of guanosines were necessary for inhibition of $PLA_2$ activity by the phosphorothioate oligonucleotide (Table III, below).

The assay was sensitive and accurate enough to discriminate between subsets of oligomers so that an inhibitory sequence could be selected. In each of the first three rounds of selection, the most active subset was readily determined. After 5 rounds, there was little difference in the activity of the subsets with at least 5 G's in a row, suggesting that the terminal positions are not critical for the inhibitory activity. The $IC_{50}$ of the "winner" improves (enzyme activity decreases) as more of the positions are fixed. As a test of the reproducibility of the assay, an eight nucleotide phosphorothioate oligonucleotide of a single sequence (TTGGGGTT) was assayed with each round of testing. This oligonucleotide acted as an internal control of the accuracy of the assay; the $IC_{50}$ was 8 μM in each assay.

TABLE

Inhibition of $PLA_2$ Activity by Library

| Subsets | Subsets $IC_{50}$ (mM) | | | |
|---|---|---|---|---|
| | X = A | X = G | X = C | X = T |
| Round 2 | | | | |
| NNGNXNNN | >50 | 25 | >50 | >50 |
| Round 3 | | | | |
| NNGXGNNN | — | 10 | >50 | — |
| Round 4 | | | | |
| NNGGGXNN | 9 | 4 | 6 | 18 |
| Round 5 | | | | |
| NAGGGGXN | 4 | 2 | 4 | 4 |
| NGGGGGXN | 2.5 | 2 | 3 | 3 |
| NCGGGGXN | 5 | 4 | 5 | 5 |
| NTGGGGXN | 19 | 5 | 17 | 15 |

STEP 3 Assay of Library of Oligomeric Compounds Against $PLA_2$

The set of compounds 122a–d constituting a library as prepared by general procedure Example 8 above, is tested in the $PLA_2$ assay for identification of inhibitors of type II $PLA_2$. Confirmation of the "winners" is made to confirm that the oligomers binds to enzyme rather than substrate and that the inhibition of any oligomer selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and oligomer. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

PROCEDURE 3

Probe for the Detection of Specific mRNA in Biological Sample

For the reliable, rapid, simultaneous quantification of multiple varieties of mRNA in a biological sample without the need to purify the mRNA from other cellular components, a mRNA of interest from a suitable biological sample, i.e., mRNA of a blood borne virus, a bacterial pathogen product in stool, urine and other like biological samples, is identified using standard microbiological techniques. An oligomeric compound of the invention having "nucleobase" functional groups (adenine, guanine, thymine and cytosine as the letters) complementary to the nucleic acid sequence of this mRNA is prepared as per the above examples. The oligomeric compound is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the oligomer thereon for a time sufficient to hybridize the mRNA to oligomer and thus to link the mRNA via the oligomer to the solid support. This immobilizes mRNA present in the sample to the CPG support. Other non-immobilized materials and components are then washed off the CPG with a wash media suitable for use with the biological sample. The mRNA on the support is labelled with ethidium bromide, biotin or a commercial radionucleotide and the amount of label immobilized on the CPG support is measured to indicate the amount of mRNA present in the biological sample.

PROCEDURE 4

Leukotriene $B_4$ Assay

Leukotriene $D_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by lothawing the concentrate, adding 35 mL of ligand diluent and swirling gently in order to resuspend the receptor homogenously. Reagents are kept on ice during the course of the experiment, and the remaining portions are stored at −20° C.

Library subsets 122a–d prepared as per general procedure of Example 8 above are diluted to 5 $\mu$M, 50 $\mu$M and 500 $\mu$M in phosphate buffer (1×PBS, 0.1% azide and 0.1% BSA, pH 7.2), yielding final test concentrations of 0.5 $\mu$M, 5 $\mu$M and 50 $\mu$M, respectively. Samples are assayed in duplicate. [$^3$H] $LTB_4$ (25 $\mu$L) is added to 25 $\mu$L of either appropriately diluted standard (unlabeled $LTB_4$) or library subset. The receptor suspension (0.2 mL) is added to each tube. Samples are incubated at 4° C. for 2 hours. Controls include [$^3$H] $LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total count vials to determine the net cpm for each sample. The degree of inhibition of binding for each library subset is determined relative to the standard (sample of ligand and receptor without library molecules).

For the purpose of illustration, consider benzyl (Bn), m-methylbenzyl (MBn), m-nitrobenzyl (NBn), and m-methoxybenzyl (MoBn) as the monomer units in position X to be used in the synthesis and selection of an oligomer with the best activity in the $LTB_4$ assay. The oligomer to be combinatorialized is shown below:

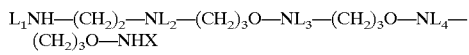

Initially, four subsets of oligomer libraries are synthesized, wherein X is one of the listed monomer units.

Each subset has a fixed monomer unit at the X position which is distinct from the monomer unit present at that position in each of the other subsets, and the other sites of combinatorialization, i.e. $L_1$, $L_2$, $L_3$, and $L_4$, represent an equimolar mixture of the listed monomer units (122a–d).

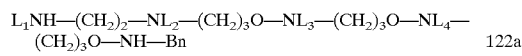 122a

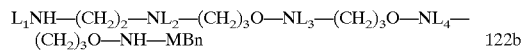 122b

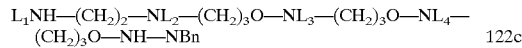 122c

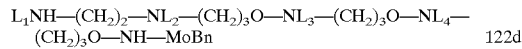 122d

Identification of the oligomer subset with the best activity leads to the determination of the ideal monomer unit at position X in the oligomer, e.g. oligomer subset 122b. The oligomer subset 122b is then chosen for further combinatorialization.

In the second round of deconvolution, four oligomer subsets are synthesized wherein each subset has a different monomer unit at the $L_1$ position in the oligomer, and the other combinatorial sites represent an equimolar mixture of the four monomer units. These subsets are assayed for activity, and the best oligomer subset (as shown below) is chosen for the next round of deconvolution.

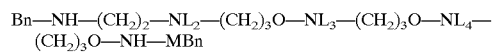

By performing subsequent rounds in this manner, the ideal monomer unit, i.e. the monomer unit that imparts greatest activity to the oligomer, is determined for each of the remaining sites of combinatorialization, namely $L_2$, $L_3$ and $L_4$. At the end of the final round of decovolution, a unique oligomer with the best activity in the $LTB_4$ assay is identified.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the structure:

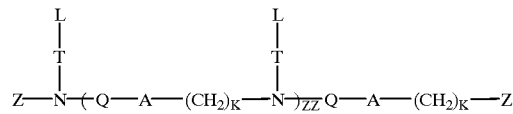

wherein:
each Z is, independently, H, a nitrogen protecting group, —T—L, N(—T—L)$_2$, a reporter molecule, or an RNA cleaving group;

zz is from 1 to about 90;

each k is, independently, 0 or 1;

at least one Q is O, and each remaining Q is independently O or (CH$_2$)$_m$;

each A is, independently, N—T—L, C(O), a single bond, or (CH$_2$)$_m$;

each m is, independently, from 1 to 5;

each T is, independently, a single bond or a group having structure II:

—[CR¹R²]ₙ—B—[CR¹R²]ₒ—[D]ₚ—[N(R³)]_q—   II where:
D is C(O), C(S), C(R¹)(NR³R⁴), CR¹R², or NR³;
B is a single bond, CH=CH, C≡C, O, S or NR⁴;
each R¹ and R² is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy- or alkylthio-substituted alkenyl having 1 to about 12 carbon atoms, hydroxy, alkoxy, alkylthio, arnino and halogen;
each R³ and R⁴ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or
R³ and R⁴, together, are cycloalkyl having 3 to about 10 carbon atoms or cycloalkenyl having 4 to about 10 carbon atoms;
n and o are, independently, 0 to 5;
q and p are, independently 0 or 1;
each L is, independently, H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, arnidine (C(=NH)NR³R⁴), guanidine (NHC(=NH)NR³R⁴), glutamyl CH(NR³R⁴)(C(=O)OR³), nitrate (ONO₂), nitro (NO₂), nitrile, trifluoromethyl (—CF₃), trifluoromethoxy (—OCF₃), O-alkyl, S-alkyl, NH-alkyl, N-dialkyl, O-aralkyl, S-aralkyl, NH-aralkyl, amino, azido (N₃), hydrazino (NHNH₂), hydroxylamino (ONH₂), sulfoxide (SO), sulfone (SO₂), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl.

2. The compound of claim 1 wherein:
B is a single bond;
o, p and q are zero; and
L is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, $C_7$–$C_{14}$ aralkyl or substituted aralkyl, and where the substituent groups are selected from hydroxyl, alkoxy, alcohol, benzyl, phenyl, nitro, thiol, thioalkoxy, halogen, alkyl, aryl, alkenyl, or alkynyl groups; halogen; hydroxyl (OH); thiol (SH); keto (C=O); carboxyl (COOH); amide (CONR); amidine (C(=NH)NR³R⁴); guanidine (NHC(=NH)NR³R⁴); glutamyl CH(NR³R⁴)(C(=O)OR³); O-alkyl; S-alkyl; NH-alkyl; N-dialkyl; O-aralkyl; S-aralkyl; NH-aralkyl; amino (NH₂); a nucleosidic base; or an amino acid side chain.

3. The compound of claim 1 wherein said zz is from 10 to about 20.

4. The compound of claim 1 wherein said zz is from 2 to about 15.

5. A composition comprising at least three compounds, each of said compounds having the formula:

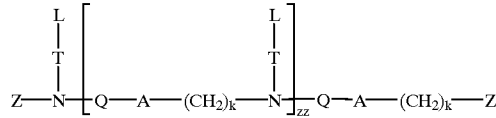

wherein:
each Z is, independently, H, a nitrogen protecting group, —T—L, N(—T—L)₂, a reporter molecule, or an RNA cleaving group;
zz is from 1 to about 90;
each k is, independently, 0 or 1;
at least one Q is N—T—L or O, and each remaining Q is independently N—T—L, O, or (CH₂)ₘ;
each A is, independently, N—T—L, C(O), a single bond, or (CH₂)ₘ;
each m is, independently, from 1 to 5;
each T is, independently, a single bond or a group having structure II:

—[CR¹R²]ₙ—B—[CR¹R²]ₒ—[D]ₚ—[N(R³)]_q—   II where:
D is C(O), C(S), C(R¹)(NR³R⁴), CR¹R², or NR³;
B is a single bond, CH=CH, C≡C, O, S or NR⁴;
each R¹ and R² is, independently, selected from the group consisting of hydrogen, alkyl having 1 to about 12 carbon atoms, alkenyl having 1 to about 12 carbon atoms, hydroxy-, alkoxy- or alkylthio-substituted alkyl or alkenyl having 1 to about 12 carbon atoms, hydroxy, alkoxy, alkylthio, amino and halogen;
each R³ and R⁴ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or
R³ and R⁴, together, are cycloalkyl having 3 to about 10 carbon atoms or cycloalkenyl having 4 to about 10 carbon atoms;
n and o are, independently, 0 to 5;
q and p are, independently 0 or 1;
each L is, independently, H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, amidine (C(=NH) NR³R⁴), guanidine (NHC(=NH)NR³R⁴), glutamyl CH(NR³R⁴)(C(=O)OR³), nitrate (ONO$_2$), nitro (NO$_2$), nitrile, trifluoromethyl (—CF$_3$), trifluoromethoxy (—OCF$_3$), O-alkyl, S-alkyl, NH-alkyl, N-dialkyl, O-aralkyl, S-aralkyl, NH-aralkyl, amino, azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl.

6. The composition of claim 5 wherein each of said zz is from 10 to about 40.

7. The composition of claim 5 wherein each of said zz is from 10 to about 20.

8. The composition of claim 5 wherein each of said zz is from 2 to about 15.

9. A compound having the structure:

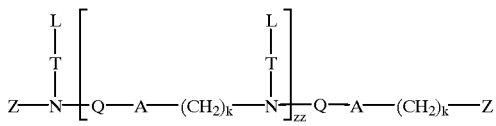

wherein:

each Z is, independently, H, a nitrogen protecting group, —T—L, N(—T—L)$_2$, a reporter molecule, or an RNA cleaving group;

zz is from 1 to about 90;

each k is, independently, 0 or 1;

at least one Q is N—T—L or O, and each remaining Q is independently N—T—L, O, or (CH$_2$)$_m$;

each A is, independently, N—T—L, C(O), a single bond, or (CH$_2$)$_m$;

each m is, independently, from 1 to 5;

each T is, independently, a single bond or a group having structure II:

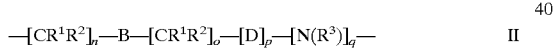

where:

D is C(O), C(S), C(R$^1$)(NR$^3$R$^4$), CR$^1$R$^2$, or NR$^3$;

B is a single bond, CH=CH, C≡C, O, S or NR$^4$;

each R$^1$ and R$^2$ is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy-, or alkylthio-substituted alkenyl having 1 to about 12 carbon atoms, hydroxy, alkoxy, alkylthio, amino and halogen;

each R$^3$ and R$^4$ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or R$^3$ and R$^4$, together, are cycloalkyl having 3 to about 10 carbon atoms or cycloalkenyl having 4 to about 10 carbon atoms;

n and o are, independently, 0 to 5;

q and p are, independently 0 or 1;

each L is, independently, H, substituted or unsubstituted C$_2$–C$_{10}$ alkyl, substituted or unsubstituted C$_2$–C$_{10}$ alkenyl, substituted or unsubstituted C$_2$–C$_{10}$ alkynyl, substituted or unsubstituted C$_4$–C$_7$ carbocylo alkyl, substituted or unsubstituted C$_4$–C$_7$ carbocylo alkenyl, substituted or unsubstituted C$_7$–C$_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, amidine (C(=NH)NR$^3$R$^4$), guanidine (NHC(=NH)NR$^3$R$^4$), glutamyl CH(NR$^3$R$^4$)(C(=O)OR$^3$), nitrate (ONO$_2$), nitro (NO$_2$), nitrile, trifluoromethyl (—CF$_3$), trifluoromethoxy (—OCF$_3$), O-alkyl, S-alkyl, NH-alkyl, N-dialkyl, O-aralkyl, S-aralkyl, NH-aralkyl, amino, azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl; and wherein T—L is C$_2$C$_{10}$ alkyl or substituted alkyl, C$_2$–C$_{10}$ alkenyl or substituted alkenyl, C$_2$–C$_{10}$ alkynyl or substituted alkynyl, C$_4$–C$_7$ carbocylo alkyl or alkenyl, or C$_7$–C$_{14}$ aralkyl or substituted aralkyl.

10. A compound having the structure:

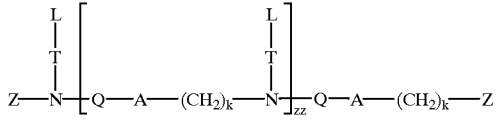

wherein:

each Z is, independently, H, a nitrogen protecting group, —T—L, N(—T—L)$_2$, a reporter molecule, or an RNA cleaving group;

zz is from 1 to about 90;

each k is, independently, 0 or 1;

at least one Q is N—T—L or O, and each remaining Q is independently N—T—L, O, or (CH$_2$)$_m$;

each A is, independently, (CH$_2$)$_m$;

each m is, independently, from 1 to 5;

each T is, independently, a single bond or a group having structure II:

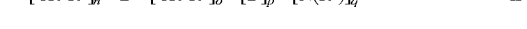

where:

D is C(O), C(S), C(R$^1$)(NR$^3$R$^4$), CR$^1$R$^2$, or NR$^3$;

B is a single bond, CH=CH, C≡C, O, S or NR$^4$;

each R$^1$ and R$^2$ is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy-, or alkylthio-substituted alkenyl having 1 to about 12 carbon atoms, hydroxy, alkoxy, alkylthio, amino and halogen;

each R$^3$ and R$^4$ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or $R^3$ and $R^4$, together, are cycloalkyl having 3 to about 10 carbon atoms or cycloalkenyl having 4 to about 10 carbon atoms;

n and o are, independently, 0 to 5;

q and p are, independently 0 or 1;

each L is, independently, H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, apolyalkyl glycol, a metal coordination group, a conjugate group, halogen, hydroxyl, thiol, keto, carboxyl, amide, ethers, thioethers, amidine (C(=NH)NR$^3$R$^4$), guanidine (NHC(=NH)NR$^3$R$^4$), glutamyl CH(N$^3$R$^4$)(C(=O)OR$^3$), nitrate (ONO$_2$), nitro (NO$_2$), nitrile, trifluoromethyl (—CF$_3$), trifluoromethoxy (—OCF$_3$), O-alkyl, S-alkyl, NH-alkyl, N-dialkyl, O-aralkyl, S-aralkyl, NH-aralkyl, amino, azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl.

11. A compound having the structure:

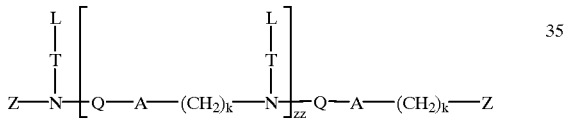

wherein:
each Z is, independently, H, a nitrogen protecting group, —T—L, N(—T—L)$_2$, a reporter molecule, or an RNA cleaving group;

zz is from 1 to about 90;

each k is, independently, 0 or 1;

at least one Q is N—T—L or O, and each remaining Q is independently N—T—L, O, or (CH$_2$)$_m$;

at least one Q is N—T—L or O, and each remaining Q is independently N—T—L, O, or (CH$_2$)$_m$;

each A is, independently, N—T—L, C(O), a single bond, or (CH$_2$)$_m$;

each m is, independently, from 1 to 5;

each T is, independently, a single bond or a group having structure II:

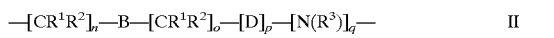

where:
D is C(O), C(S), C(R$^1$)(NR$^3$R$^4$), CR$^1$R$^2$, or NR$^3$;

B is a single bond, CH=CH, C≡C, O, S or NR$^4$;

each R$^1$ and R$^2$ is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy-, or alkylthio-substituted alkenyl having 1 to about 12 carbon atoms, hydroxy, alkoxy, alkylthio, amino and halogen;

each R$^3$ and R$^4$ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or $R^3$ and $R^4$, together, are cycloalkyl having 3 to about 10 carbon atoms or cycloalkenyl having 4 to about 10 carbon atoms;

n and o are, independently, 0 to 5;

q and p are, independently 0 or 1;

each L is, independently, H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, amidine (C(=NH)NR$^3$R$^4$), guanidine (NHC(=NH)NR$^3$R$^4$), glutamyl CH(NR$^3$R$^4$)(C(=O)OR$^3$), nitrate (ONO$_2$), nitro (NO$_2$), nitrile, trifluoromethyl (—CF$_3$), trifluoromethoxy (—OCF$_3$), O-alkyl, S-alkyl, NH-alkyl, N-dialkyl, O-aralkyl, S-aralkyl, NH-aralkyl, amino, azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl; and wherein —T—L is a tert-butoxycarbonyl, sulfenyltriphenyl or phthaloyl nitrogen protecting group.

12. A compound having the structure:

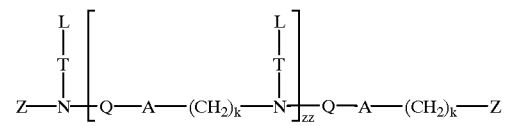

wherein:
each Z is, independently, H, a nitrogen protecting group, —T—L, N(—T—L)$_2$, a reporter molecule, or an RNA cleaving group;

zz is from 1 to about 90;

each k is, independently, 0 or 1;

at least one Q is N—T—L or O, and each remaining Q is independently N—T—L, O, or (CH$_2$)$_m$;

each A is, independently, N—T—L, C(O), (CH$_2$)$_m$;

each m is, independently, from 1 to 5;

each T is, independently, a single bond or a group having structure II:

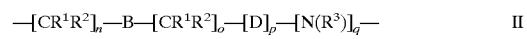

where:

D is C(O), C(S), C(R¹)(NR³R⁴), CR¹R², or NR³;
B is a single bond, CH=CH, C≡C, O, S or NR⁴;
each R¹ and R² is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy-, or alkylthio-substituted alkenyl having 1 to about 12 carbon atoms, hydroxy, alkoxy, alkylthio, amino and halogen;
each R³ and R⁴ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or
R³ and R⁴, together, are cycloalkyl having 3 to about 10 carbon atoms or cycloalkenyl having 4 to about 10 carbon atoms;
n and o are, independently, 0 to 5;
q and p are, independently 0 or 1;
each L is, independently, H, substituted or unsubstituted $C_2$–$C_{10}$ alkyl, substituted or unsubstituted $C_2$–$C_{10}$ alkenyl, substituted orunsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, amidine (C(=NH)NR³R⁴), guanidine (NHC(=NH)NR³R⁴), glutamyl CH(NR³R⁴)(C(=O)OR³), nitrate (ONO₂), nitro (NO₂), nitrile, trifluoromethyl (—CF₃), trifluoromethoxy (—OCF₃), O-alkyl, S-alkyl, NH-alkyl, N-dialkyl, O-aralkyl, S-aralkyl, NH-aralkyl, amino, azido (N₃), hydrazino (NHNH₂), hydroxylamino (ONH₂), sulfoxide (SO), sulfone (SO₂), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl; and
wherein at least one of said Q is O.

13. A compound having the structure:

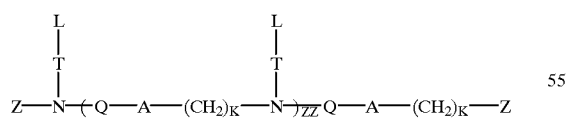

wherein:
each Z is, independently, H, a nitrogen protecting group, —T—L, N(—T—L)₂, a reporter molecule, or an RNA cleaving group;
zz is from 1 to about 90;
each k is, independently, 0 or 1;

at least one Q is O, and each remaining Q is independently O or (CH₂)$_m$;
each A is, independently, N—T—L, C(O), a single bond, or (CH₂)$_m$;
each m is, independently, from 1 to 5;
each T is, independently, a single bond or a group having structure II:

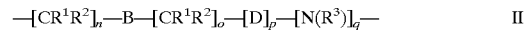

where:
D is C(O), C(S), C(R¹)(NR³R⁴), CR¹R², or NR³;
B is a single bond, CH=CH, C≡C, O, S or NR⁴;
each R¹ and R² is, independently, selected from the group consisting of hydrogen, alkyl having 1 to about 12 carbon atoms, alkenyl having 1 to about 12 carbon atoms, hydroxy-, alkoxy- or alkylthio-substituted alkyl having 1 to about 12 carbon atoms, hydroxy-, alkoxy- or alkylthio-substituted alkenyl having 1 to about 12 carbon atoms, hydroxy, alkoxy, alkylthio, arnino and halogen;
each R³ and R⁴ are, independently, H, alkyl having 1 to about 10 carbon atoms, alkenyl having 2 to about 10 carbon atoms, alkynyl having 2 to about 10 carbon atoms, aryl having 7 to about 14 carbon atoms, heterocyclic; or
R³ and R⁴, together, are cycloalkyl having 3 to about 10 carbon atoms or cycloalkenyl having 4 to about 10 carbon atoms;
n and o are, independently, 0 to 5;
q and p are, independently 0 or 1;
each L is, independently, H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocylo alkyl, substituted or unsubstituted $C_4$–$C_7$ carbocylo alkenyl, substituted or unsubstituted $C_7$–$C_{14}$ aralkyl, a heterocyclic moiety having heteroatoms selected from nitrogen, oxygen and sulfur, where said substitutions are selected from alkyl, alkenyl, alkynyl, alkoxy, thiol, thioalkoxy, hydroxyl, aryl, benzyl, phenyl, nitro, and halogen, an ether having 2 to 10 carbon atoms and 1 to 4 oxygen or sulfur atoms, a polyalkyl glycol, a metal coordination group, a conjugate group, halogen, hydroxyl, thiol, keto, carboxyl, amide, ethers, thioethers, arnidine (C(=NH)NR³R⁴), guanidine (NHC(=NH)NR³R⁴), glutamyl CH(NR³R⁴)(C(=O)OR³), nitrate (ONO₂), nitro (NO₂), nitrile, trifluoromethyl (—CF₃), trifluoromethoxy (—OCF₃), O-alkyl, S-alkyl, NH-alkyl, N-dialkyl, O-aralkyl, S-aralkyl, NH-aralkyl, amino, azido (N₃), hydrazino (NHNH₂), hydroxylamino (ONH₂), sulfoxide (SO), sulfone (SO₂), sulfide (S—), disulfide (S—S), silyl, a nucleosidic base, an amino acid side chain, a nitrogen protecting group, a carbohydrate, a drug, or a group capable of hydrogen bonding, provided that when each T is a single bond at least one L is not H or alkyl; and
wherein at least one of said A is other than C(O).

* * * * *

UNITED STATES PATENT AND TRADEMARK OFFICE
CERTIFICATE OF CORRECTION

PATENT NO. : 6,121,433
DATED : September 19, 2000
INVENTOR(S) : Cook et al.

It is certified that error appears in the above-identified patent and that said Letters Patent is hereby corrected as shown below:

Title page,
OTHER PUBLICATIONS, (under Miller et al.), please delete "$G^Mp(Et)G^mp(Et)U$," and insert therefor -- $G^mp(Et)G^mp(Et)U$, --;

Column 29,
Line 48, please delete "NPh(thl7)" and insert therefor -- Nphth(117) --;

Column 47,
Line 11, please delete "$D_4$" and insert therefor -- $B_4$ --;

Column 49,
Line 13, please delete "arnino" and insert -- amino --;

Column 53,
Line 7, please delete "orunsubstituted" and insert therefor -- unsubstituted --;
Line 17, please delete "apolyalkyl" and insert therefor -- a polyalkyl --;

Column 54,
Line 16, please delete "orunsubstituted" insert therefor -- unsubstituted --;

Column 55,
Line 23, please delete "orunsubstituted" insert therefor -- unsubstituted --;

Signed and Sealed this

Twenty-first Day of May, 2002

*Attest:*

JAMES E. ROGAN
*Attesting Officer*     Director of the United States Patent and Trademark Office